US008188263B2

(12) United States Patent
MacLachlan et al.

(10) Patent No.: US 8,188,263 B2
(45) Date of Patent: *May 29, 2012

(54) MODIFIED SIRNA MOLECULES AND USES THEREOF

(75) Inventors: Ian MacLachlan, Mission (CA); Adam Judge, Vancouver (CA); Amy C. H. Lee, Surrey (CA); Vandana Sood, Vancouver (CA)

(73) Assignee: Protiva Biotherapeutics, Inc., Burnaby, BC (CA)

( * ) Notice: Subject to any disclaimer, the term of this patent is extended or adjusted under 35 U.S.C. 154(b) by 419 days.

This patent is subject to a terminal disclaimer.

(21) Appl. No.: 12/359,119

(22) Filed: Jan. 23, 2009

(65) Prior Publication Data

US 2009/0270481 A1    Oct. 29, 2009

Related U.S. Application Data

(63) Continuation of application No. 11/592,756, filed on Nov. 2, 2006, now Pat. No. 8,101,741.

(60) Provisional application No. 60/817,933, filed on Jun. 30, 2006, provisional application No. 60/732,964, filed on Nov. 2, 2005.

(51) Int. Cl.
C07H 21/04    (2006.01)
(52) U.S. Cl. ..................................... 536/24.5
(58) Field of Classification Search .................. 536/24.5
See application file for complete search history.

(56) References Cited

U.S. PATENT DOCUMENTS

| | | | |
|---|---|---|---|
| 4,394,448 A | 7/1983 | Szoka, Jr. et al. |
| 4,438,052 A | 3/1984 | Weder et al. |
| 4,515,736 A | 5/1985 | Deamer |
| 4,598,051 A | 7/1986 | Papahadjopoulos et al. |
| 4,897,355 A | 1/1990 | Eppstein et al. |
| 5,013,556 A | 5/1991 | Woodle et al. |
| 5,171,678 A | 12/1992 | Behr et al. |
| 5,208,036 A | 5/1993 | Eppstein et al. |
| 5,225,212 A | 7/1993 | Martin et al. |
| 5,264,618 A | 11/1993 | Felgner et al. |
| 5,279,833 A | 1/1994 | Rose |
| 5,283,185 A | 2/1994 | Epand et al. |
| 5,320,906 A | 6/1994 | Eley et al. |
| 5,545,412 A | 8/1996 | Eppstein et al. |
| 5,578,475 A | 11/1996 | Jessee et al. |
| 5,641,662 A | 6/1997 | Debs et al. |
| 5,656,743 A | 8/1997 | Busch et al. |
| 5,703,055 A | 12/1997 | Felgner et al. |
| 5,705,385 A | 1/1998 | Bally et al. |
| 5,820,873 A | 10/1998 | Choi et al. |
| 5,976,567 A | 11/1999 | Wheeler et al. |
| 5,981,501 A | 11/1999 | Wheeler et al. |
| 6,417,326 B1 | 7/2002 | Cullis et al. |
| 6,534,484 B1 | 3/2003 | Wheeler et al. |
| 6,586,410 B1 | 7/2003 | Wheeler et al. |
| 6,680,068 B2 | 1/2004 | Campbell et al. |
| 6,815,432 B2 | 11/2004 | Wheeler et al. |
| 6,858,224 B2 | 2/2005 | Wheeler et al. |
| 7,341,738 B2 | 3/2008 | Semple et al. |
| 7,807,815 B2 | 10/2010 | MacLachlan et al. |
| 7,838,658 B2 * | 11/2010 | MacLachlan et al. ....... 536/24.5 |
| 7,982,027 B2 * | 7/2011 | MacLachlan et al. ....... 536/24.5 |
| 2001/0044416 A1 | 11/2001 | McCluskie et al. |
| 2003/0036516 A1 | 2/2003 | Agrawal |
| 2003/0073640 A1 | 4/2003 | Beigelman et al. |
| 2003/0077829 A1 | 4/2003 | MacLachlan |
| 2003/0104044 A1 | 6/2003 | Semple et al. |
| 2003/0125263 A1 | 7/2003 | Gold et al. |
| 2003/0143732 A1 | 7/2003 | Fosnaugh et al. |
| 2003/0166001 A1 | 9/2003 | Lipford |
| 2003/0175950 A1 | 9/2003 | McSwiggen |
| 2004/0009949 A1 | 1/2004 | Krieg |
| 2004/0019001 A1 | 1/2004 | McSwiggen |
| 2004/0142892 A1 | 7/2004 | Finn et al. |
| 2004/0171033 A1 | 9/2004 | Baker et al. |
| 2004/0192626 A1 | 9/2004 | McSwiggen et al. |
| 2004/0198640 A1 | 10/2004 | Leake et al. |
| 2004/0253723 A1 | 12/2004 | Tachas et al. |
| 2004/0259247 A1 | 12/2004 | Tuschl et al. |
| 2005/0020525 A1 | 1/2005 | McSwiggen et al. |
| 2005/0064595 A1 | 3/2005 | MacLachlan et al. |

(Continued)

FOREIGN PATENT DOCUMENTS

CA    2359180 A1    8/2000
(Continued)

OTHER PUBLICATIONS

Prakash et al. MEDI-175 Genral Oral Session, Division of Medicinal Chemistry, The 227th ACS National Meeting, 2004, 1 page.*
Alexopoulou, L., et al., "Recognition of double-stranded RNA and activation of NF-kappaB by Toll-like receptor 3," Nature, 2001, vol. 413, No. 6857, pp. 732-738.
Allerson, C. R., et al., "Chemically-modified siRNA motifs with enhanced in vitro activity and stability—MEDI 174," General Oral Session, Division of Medicinal Chemistry, The 227th ACS National Meeting, 2004, 1 page.

(Continued)

Primary Examiner — Brian Whiteman
(74) Attorney, Agent, or Firm — Kilpatrick Townsend & Stockton LLP

(57)    ABSTRACT

The present invention provides chemically modified siRNA molecules and methods of using such siRNA molecules to silence target gene expression. Advantageously, the modified siRNA of the present invention is less immunostimulatory than its corresponding unmodified siRNA sequence and retains RNAi activity against the target sequence. The present invention also provides nucleic acid-lipid particles comprising a modified siRNA, a cationic lipid, and a non-cationic lipid, which can further comprise a conjugated lipid that inhibits aggregation of particles. The present invention further provides methods of silencing gene expression by administering a modified siRNA to a mammalian subject. Methods for identifying and/or modifying an siRNA having immunostimulatory properties are also provided.

28 Claims, 27 Drawing Sheets

U.S. PATENT DOCUMENTS

| | | | |
|---|---|---|---|
| 2005/0100983 A1 | 5/2005 | Bauer et al. |
| 2005/0107325 A1 | 5/2005 | Manoharan et al. |
| 2005/0119214 A1 | 6/2005 | Manoharan et al. |
| 2005/0119273 A1 | 6/2005 | Lipford et al. |
| 2005/0130911 A1 | 6/2005 | Uhlmann et al. |
| 2005/0175682 A1 | 8/2005 | Heyes et al. |
| 2005/0239733 A1 | 10/2005 | Jurk et al. |
| 2005/0256073 A1 | 11/2005 | Lipford et al. |
| 2005/0282188 A1 | 12/2005 | Haeberli et al. |
| 2006/0008910 A1 | 1/2006 | MacLachlan et al. |
| 2006/0009409 A1 | 1/2006 | Woolf |
| 2006/0019916 A1 | 1/2006 | Krieg et al. |
| 2006/0051405 A1 | 3/2006 | MacLachlan et al. |
| 2006/0083780 A1 | 4/2006 | Heyes et al. |
| 2006/0105976 A1 | 5/2006 | Soutschek et al. |
| 2006/0134189 A1 | 6/2006 | MacLachlan et al. |
| 2006/0142230 A1 | 6/2006 | Quay |
| 2006/0211642 A1 | 9/2006 | McSwiggen et al. |
| 2006/0217330 A1 | 9/2006 | Hartmann et al. |
| 2006/0240554 A1 | 10/2006 | Chen et al. |
| 2007/0031844 A1 | 2/2007 | Khvorova et al. |
| 2007/0042983 A1 | 2/2007 | Haeberli et al. |
| 2007/0135370 A1 | 6/2007 | MacLachlan et al. |
| 2007/0135372 A1 | 6/2007 | MacLachlan et al. |
| 2007/0218122 A1 | 9/2007 | MacLachlan et al. |
| 2008/0171716 A1 | 7/2008 | MacLachlan et al. |
| 2008/0249046 A1 | 10/2008 | MacLachlan et al. |
| 2008/0249294 A1 | 10/2008 | Haeberli et al. |
| 2009/0012021 A1* | 1/2009 | Sood et al. ............ 514/44 |
| 2009/0137500 A1 | 5/2009 | McSwiggen et al. |
| 2009/0270481 A1 | 10/2009 | MacLachlan et al. |
| 2009/0286852 A1 | 11/2009 | Kariko et al. |
| 2010/0130588 A1 | 5/2010 | Yaworski et al. |
| 2011/0071208 A1 | 3/2011 | MacLachlan et al. |
| 2011/0076335 A1 | 3/2011 | Yaworski et al. |
| 2011/0195127 A1 | 8/2011 | Lee et al. |
| 2011/0262527 A1 | 10/2011 | Heyes et al. |

FOREIGN PATENT DOCUMENTS

| | | |
|---|---|---|
| EP | 1 764 108 A1 | 3/2007 |
| GB | 2 397 818 B | 3/2005 |
| WO | WO 91/16024 A1 | 10/1991 |
| WO | WO 93/05162 A1 | 3/1993 |
| WO | WO 93/12240 A1 | 6/1993 |
| WO | WO 93/12756 A2 | 7/1993 |
| WO | WO 93/24640 A2 | 12/1993 |
| WO | WO 93/25673 A1 | 12/1993 |
| WO | WO 95/02698 A1 | 1/1995 |
| WO | WO 95/18863 A1 | 7/1995 |
| WO | WO 95/35301 A1 | 12/1995 |
| WO | WO 96/02655 A1 | 2/1996 |
| WO | WO 96/10390 A1 | 4/1996 |
| WO | WO 96/41873 A1 | 12/1996 |
| WO | WO 98/51278 A2 | 11/1998 |
| WO | WO 00/44895 A1 | 8/2000 |
| WO | WO 01/05374 A1 | 1/2001 |
| WO | WO 02/34236 | 2/2002 |
| WO | WO 02/34236 A2 | 5/2002 |
| WO | WO 02/44321 A2 | 6/2002 |
| WO | WO 02/072068 A2 | 9/2002 |
| WO | WO 02/087541 A1 | 11/2002 |
| WO | WO 03/029453 A2 | 4/2003 |
| WO | WO 03/070918 A2 | 8/2003 |
| WO | WO 03/086280 A2 | 10/2003 |
| WO | WO 03/097805 A2 | 11/2003 |
| WO | WO 2004/029212 A | 4/2004 |
| WO | WO 2004/046324 A | 6/2004 |
| WO | WO 2004/065546 A2 | 8/2004 |
| WO | WO 2004/073685 A1 | 9/2004 |
| WO | WO 2004/091515 A2 | 10/2004 |
| WO | WO 2004/110499 A1 | 12/2004 |
| WO | WO 2005/007196 A2 | 1/2005 |
| WO | WO 2005/019453 A3 | 3/2005 |
| WO | WO 2005/021044 | 3/2005 |
| WO | WO 2005/026372 A1 | 3/2005 |
| WO | WO 2005/044981 A3 | 5/2005 |
| WO | WO 2005/078094 A2 | 8/2005 |
| WO | WO 2005/120152 A2 | 12/2005 |
| WO | WO 2005/121348 A1 | 12/2005 |
| WO | WO 2006/063252 A2 | 6/2006 |
| WO | WO 2006/074546 A1 | 7/2006 |
| WO | WO 2007/048046 A2 | 4/2007 |
| WO | WO 2007/051303 A1 | 5/2007 |
| WO | WO 2007/133800 A2 | 11/2007 |
| WO | WO 2008/019486 A1 | 2/2008 |

OTHER PUBLICATIONS

Allerson, C. R., et al., "Fully 2'-Modified Oligonucleotide Duplexes with Improved in Vitro Potency and Stability Compared to Unmodified Small Interfering RNA," J. Med. Chem., 2005, vol. 48, No. 4, pp. 901-904.

Aoki, H., et al., "Inhibition of motility and invasiveness of renal cell carcinoma induced by short interfering RNA transfection of β1, 4GalNAc transferase," FEBS Letters. Available online, 2004, vol. 567, pp. 203-208.

Arpicco, S., et al., "Preparation and Characterization of Novel Cationic Lipids Developed for Gene Transfection," Proceed. Int'l Symp. Control. Rel. Bioact. Mater. (Controlled Release Society, Inc.), 1999, vol. 26, pp. 759-760.

Arpicco, S., et al., "Synthesis, characterization and transfection activity of new saturated and unsaturated cationic lipids," IL Farmaco, 2004, vol. 59, pp. 869-878.

Ballas, N. et al., "Liposomes bearing a quarternary ammonium detergent as an efficient vehicle for functional transfer of TMV-RNA into plant protoplasts," Biochim. Biophys. Acta, 1998, pp. 8-18, vol. 939.

Barinaga, M., "Step Taken Toward Improved Vectors for Gene Transfer," Science, 1994, p. 1326, vol. 266.

Barrat et al., "Nucleic acids of mammalian origin can act as endogenous ligands for Toll-like receptors and may promote systemic lupus erythematosus," Journal of Experimental Medicine, 2005, vol. 202, No. 8, pp. 1131-1139.

Beale, G., et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, 2003, vol. 11, No. 7, pp. 449-456.

Behr, J-P., "Synthetic Gene-Transfer Vectors," Acc. Chem. Res. 1993, pp. 274-278, vol. 26.

Bosscher et al., "The Interplay between the Glucocorticoid Receptor and Nuclear Factor-kB or Activator Protein-1:Molecular Mechanisms for Gene Repression," Endocrine Reviews 24:488-522, 2003.

Braasch, D. A., et al., "RNA Interference in Mammalian Cells by Chemically-Modified RNA," Biochemistry, 2003, vol. 42, No. 26, pp. 7967-7975.

Bridge, A.J., et al., "Induction of an interferon response by RNAi vectors in mammalian cells," Nat. Genet., 2003, vol. 34, No. 3, pp. 263-264.

Brigham, K. et al., "Rapid Communication: In vivo Transfection of Murine Lungs with a Functioning Prokaryotic Gene Using a Liposome Vehicle," Am. J. Med. Sci., 1989, pp. 278-281, vol. 298.

Brummelkamp et al., (2002) Science 296:550-553.

Budker et al., Mechanism of plasmid delivery by hydrodynamic tail vein injection. II. Morphological studies, 2006, The journal of Gene Medicine, vol. 8, pp. 874-888.

Cevc, G., "How Membrane Chain-Melting Phase-Transition Temperature is Affected by the Lipid Chain Asymmetry and Degree of Unsaturation: An Effective Chain-Length Model," Biochemistry, 1991, vol. 30, pp. 7186-7193.

Chiu, Y., et al., "siRNA function in RNAi: A chemical modification analysis," RNA, 2003, vol. 9, No. 9, pp. 1034-1048.

Christensen et al., Toll-like Receptor 7 and TLR9 dictate autoantibody specificity and have opposing inflammatory and regulatory roles in a murine model of lupus, Sep. 2006, Immunity, vol. 25, pp. 417-428.

Cortesi, R., et al., "Effect of cationic liposome composition on in vitro cytotoxicity and protective effect on carried DNA," International Journal of Pharmaceutics, 1996, pp. 69-78, vol. 139.

Crystal, R., "Transfer of Genes to Humans: Early Lessons and Obstacles to Success," Science, 1995, pp. 404-410, vol. 270.

Culver K.,, "The First Human Gene Therapy Experiment," Gene Therapy: A Handbook for Physicians, 1994, pp. 33-40.

Czauderna, F., et al., "Structural variations and stabilizing modifications of synthetic siRNAs in mammalian cells," Nucleic Acids Research, 2003, vol. 31, No. 11, pp. 2705-2716.

Dalby, B. et al., "Advanced transfection with Lipofectamine 2000 reagent: primary neurons, siRNA, and high-throughput applications." Methods (2004), 33(2):95-103.

Dandona et al., "Effect of dexamethasone on reactive oxygen species generation by leukocytes and plasma interleukin-10 concentrations: A pharmacodynamic study," Clin Pharmacol Ther. 1999, 66(1): 58-65.

Diebold, S.S., et al., "Innate antiviral responses by means of TLR7-mediated recognition of single-stranded RNA," Science, 2004, vol. 303, No. 5663, pp. 1529-1531.

Duzgunes, N., "Membrane Fusion," Subcellular Biochemistry, 1985, pp. 195-286, vol. 11.

Dwarki, V.J., et al., "Cationic Liposime-Mediated RNA Transfection," Methods in Enzymology, 1993, pp. 644-654, vol. 217.

Elbashir, S. M., et al., "Functional anatomy of siRNAs for mediating efficient RNAi in *Drosophila melanogaster* embryo lysate," The EMBO Journal, 2001, vol. 20, No. 23, pp. 6877-6888.

Enoch, H. et al., "Formation and properties of 1000-Å-diameter, single-bilayer phospholipid vesicles," Proc. Natl. Acad. Sci. USA, 1979, pp. 145-149, vol. 76, No. 1.

Felgner, J., et al., "Cationic Lipid-Mediated Transfection in Mammalian Cells: "Lipofection"," J. Tiss. Cult. Meth., 1993, pp. 63-68, vol. 15.

Felgner, J.H., et al., "Enhanced Gene Delivery and Mechanism Studies with a Novel Series of Cationic Lipid Formulations," The Journal of Biological Chemistry, Jan. 1994, pp. 2550-2561, vol. 269, No. 4.

Felgner, P. et al., "Lipofection: A highly efficient, lipid-mediated DNA-transfection procedure," Proc. Natl. Acad. Sci. USA, 1987, pp. 7413-7417, vol. 84.

Flynn, M.A., et al., "Efficient delivery of small interfering RNA for inhibition of IL-12p40 expression in vivo," Journal of Inflammation, 2004, vol. 1, No. 4, pp. 1-12.

Gao, X. et al., "A Novel Cationic Liposome Reagent for Efficient Transfection of Mammalian Cells," Biochem. Biophys. Res. Comm., 1991, pp. 280-285, vol. 179.

GenBank accession No. BD134629 from JP 2002051786 patent application (Komori Hisafumi) Feb. 19, 2002.

Gershon, H. et al., "Mode of Formation and Structural Feature of DNA-Cationic Liposome Complexes Used for Transfection," Biochemistry, 1993, pp. 7413-7151, vol. 32.

Gruneich, J.A., et al., "Cationic corticosteroid for nonviral gene delivery," Gene Ther., 2004, vol. 11, pp. 668-674.

Guy-Caffey, J., et al., "Novel Polyaminolipids Enhance the Cellular Uptake of Oligonucleotides," The Journal of Biological Chemistry, Dec. 1995, pp. 31391-31396, vol. 270, No. 52.

Hafez et al., "On the mechanism whereby cationic lipids promote intracellular delivery of polynucleic acids," Gene Therapy, 2001, vol. 8, pp. 1188-1196.

Hamada, Makiko, et al., "Effects on RNA Interference in Gene Expression (RNAi) in Cultured Mammalian Cells of Mismatches and the Introduction of Chemical Modifications at the 3'-Ends of siRNAs," Antisense and Nucleic Acid Drug Development, 2002, vol. 12, pp.

Hawley-Nelson, et al., "LipofectAmine™ Reagent: A New, Higher Efficiency Polycationic Liposome Transfection Reagent," Focus, 1993, p. 73-80, vol. 15, No. 3.

Heil, F., et al., "Species-specific recognition of single-stranded RNA via Toll-like receptor 7 and 8," Science, 2004, vol. 303, pp. 1526-1529.

Henry et al., "Chemically modified Oligonucleotides Exhibit Decreased Immune Stimulation in Mice," JPET 292:468-479, 2000.

Heyes, et al., (2005) J. Controlled Release 107:276-287.

Hornung, V., et al., "Sequence-specific potent induction of IFN-α by short interfering RNA in plasmacytoid dendritic cells through TLR7," Nature Medicine, 2005, vol. 11, No. 3, pp. 263-270.

Hyde, S., et al., "Correction of the ion transport defect in cystic fibrosis transgenic mice by gene therapy," Nature, 1993, pp. 250-256, vol. 362.

Jeffs et al., "A scalable, extrusion-free method for efficient liposomal encapsulation of plasmid DNA," Pharmaceutical Research, 2005, vol. 22 No. 3, pp. 362-372.

Jiang, L., et al., "Comparison of protein precipitation methods for sample preparation prior to proteomic analysis," Journal of Chromatography A, 2004, vol. 1023, pp. 317-320.

Judge, A. D., et al., "Design of Noninflammatory Synthetic siRNA Mediating Potent Gene Silencing in Vivo," Molecular Therapy, 2006, vol. 13, No. 3, pp. 494-505.

Judge, A. D., et al., "Sequence-dependent stimulation of the mammalian innate immune response by synthetic siRNA," Nature Biotechnology, 2005, vol. 23, No. 4, pp. 457-462.

Juliano R., and Stamp, D., "The Effect of Particle Size and Charge on the Clearance Rates of Liposomes and Liposome Encapsulated Drugs," Biochem. Biophys. Res. Commun., 1975, pp. 651-658, vol. 63.

Jurk et al., "Modulating responsiveness of human TLR7 and 8 to small molecule ligands with T-rich phosphorothiate oligodeoxynucleotides," Eur. J. Immunol., 2006, vol. 36, pp. 1815-1826.

Kariko, K., et al., "Small Interfering RNAs Mediate Sequence-Independent Gene Suppression and Induce Immune Activation by Signaling through Toll-Like Receptor 3," Journal of Immunology, 2004, vol. 172, No. 11, pp. 6545-6549.

Kariko et al., Suppression of RNA recognition by Toll-like receptors: the impact of nucleoside modification and the evolutionary origin of RNA. Immunity, Aug. 2005, vol. 23, No. 2, pp. 165-175.

Kim, D.H., et al., "Interferon induction by siRNAs and ssRNAs synthesized by phage polymerase," Nat. Biotechnol., 2004, vol. 22, No. 3, pp. 321-325.

Keough, K., "Influence of chain unsaturation and chain position on thermotropism and intermolecular interactions in membranes," Biochem. Soc. Transactions, 1990, vol. 18, No. 5, pp. 835-837.

Lee et al., siRNA—getting the message out, 2006, European Journal of Pharmaceutical Sciences, vol. 27, pp. 401-410.

Legendre, J.Y. and Szoka, F., "Delivery of Plasmid DNA into Mammalian Cell Lines Using pH-Sensitive Liposomes: Comparison with Cationic Liposomes," Pharm. Res., 1992, pp. 1235-1242, vol. 9, No. 10.

Leventis, R., et al.,, "Interactions of mammalian cells with lipid dispersions containing novel metabolizable cationic amphiphiles," Biochem. Biophys. Acta, 1990, p. 124, vol. 1023.

Lewis et al., Efficient delivery of siRNA for inhibition of gene expression in postnatal mice, 2002, Nature Genetics, vol. 32, pp. 107-108.

Liu, Y., et al., "Strain-based Genetic Differences Regulate the Efficiency of Systemic Gene Delivery as Well as Expression," J. Biol. Chem., 2002, vol. 277, pp. 4966-4972.

Lund, J.M., et al., "Recognition of single-stranded RNA viruses by Toll-like receptor 7," Proc. Natl. Acad. Sci. USA, 2004, vol. 101, No. 15, pp. 5598-5603.

Manoharan, M., "RNA interference and chemically modified small interfering RNAs," Current Opinion in Chemical Biology, 2004, vol. 8, pp. 570-579.

Marshall, E., "Gene Therapy's Growing Pains," Science, 1995, pp. 1050-1055, vol. 269.

Martinez, A., et al., "Small interfering RNA Molecules as Potential Anti-Human Hepatitis C Virus Agents: Identification and Characterization of Two siRNA Molecules Highly Conserved in the Major Genotypes of the Virus," Preclinica, 2003, vol. 1, No. 5, pp. 274-283.

Mena et al., Innate immunity responses induced by CpG oligodeoxyribonucleotide stimulation of ovine blood mononuclear cells, 2003, Immunity, vol. 110, pp. 250-2570.

McCaffrey et al., RNA interference in adult mice, 2002, Nature, vol. 418, pp. 38-39.

Morrissey et al., Activity of stabilized short interfering RNA in a mouse model of hepatitis B virus replication, 2005, Hepatology, vol. 41, pp. 1349-1356.

Morrissey, David, et al., "Potent and Persistent in vivo anti-HBV activity of chemically modified siRNAs," Nature Biotechnology, 2005, vol. 23, No. 8, pp. 1002-1007. XP002452540.

Moss, E.G. et al., "Small-interfering RNAs in the radar of the interferon system," Nature Cell Biology, Sep. 2003, vol. 5, No. 9, pp. 771-772.

Nguyen, et al., "RNAI Therapeutics: An Update on Delivery," Current Opinion in Molecular Therapeutics, 2008, vol. 10(2): 158-67.
Orkin, et al., NIH Report, Report and Recommendations of the Panel to Assess the NIH Investment in Research on Gene Therapy, 1995.
Paul, C., et al., "Effective expression of small interfering RNA in human cells," Nature Biotech., 2002, vol. 20, pp. 505-508.
Pisitkun et al., "Autoreactive B Cell Responses to RNA-Related Antigens Due to TLR7 Gene Duplication," Science, 2006, vol. 312, pp. 1669-1672.
Prakash, T. P., et al., "Positional Effect of Chemical Modifications on Short Interference RNA Activity in Mammalian Cells," J. Med. Chem., 2005, vol. 48, No. 13, pp. 4247-4253.
Przybylska, M., et al., "Partial correction of the α-galactosidase A deficiency and reduction of glycolipid storage in Fabry mice using synthetic vectors," J. Gene Med., 2004, vol. 6, pp. 85-92.
Puyal, C., et al., "A new cationic liposome encapsulating genetic material: A potential delivery system for polynucleotides," Eur. J. Biochem., 1995, pp. 697-703, vol. 228.
Robbins et al., "2'-O-methyl-modified RNAs Act as TLR7 Antagonists," The American Society of Gene Therapy, Molecular Therapy, vol. 15, No. 9, 2007, pp. 1663-1669.
Schmidt, Charlie "Negotiating the RNAi patent thicket," Mar. 2007, Nature Biotechnology, vol. 25, pp. 273-275.
Sioud, M. "Induction of inflammatory Cyokines and Interferon responses by double-stranded and single stranded siRNAs is sequence-dependent and requires endosomal localization," Journal of Molecular Biology, 2005, vol. 348, pp. 1079-1090.
Sioud, M., et al., "Cationic liposome-mediated delivery of siRNAs in adult mice," Biochem. Biophys. Res. Commun., 2003, vol. 312, No. 4, pp. 1220-1225.
Sioud, M., "Single-stranded small interfering RNA are more immunostimulatory than their double-stranded counterparts: a central role for 2'-hydroxy uridines in immune responses," European Journal of Immunology, 2006, vol. 36, pp. 1222-1230.
Sledz, C.A., et al., "Activation of the interferon system by short-interfering RNAs," Nat. Cell Biol., 2003, vol. 5, No. 9, pp. 834-839.
Soutschek, J., et al., "Therapeutic silencing of an endogenous gene by systemic administration of modified siRNAs," Nature, 2004, vol. 432, pp. 173-178.
Spagnou, S., et al., "Lipidic Carriers of siRNA: Differences in the Formulation, Cellular Uptake, and Delivery with Plasmid DNA," Biochemistry, 2004, vol. 43, pp. 13348-13356.
Stamatatos, L., et al., "Interactions of Cationic Lipid Vesicles with Negatively Charged Phospholipid Vesicles and Biological Membranes," Biochemistry, 1988, pp. 3917-3925, vol. 27.
Stunz et al., "Inhibitory oligonucleotides specifically block effects of stimulatory CpG oligonucleotides in B cells." European Journal of Immunology, 2002, vol. 32, No. 5, pp. 1212-1222.
Subramanian et al., "A Tlr7 translocation accelerates systemic autoimmunity in murine lupus," PNAS, 2006, vol. 103, No. 26, pp. 9970-9975.
Sugiyama et al., CpG RNA: Identification of novel single-stranded RNA that stimulates human CD14+CD11c+monocytes, 2005, the Journal of Immunology, vol. 174, pp. 2273-2279.
Sun et al., "TLR7/9 Antagonists as Therapeutics for Immune-Mediated Inflammatory Disorders," Inflammation & Allergy—Drug Targets, 2007, vol. 6, pp. 223-235.
Szoka, F. et al., "Comparative Properties and Methods of Preparation of Lipid Vesicles (Liposomes)," Ann. Rev. Biophys. Bioeng., 1980, pp. 467-508, vol. 9.
Szoka, F. et al., "Procedure for preparation of liposomes with large internal aqueous space and high capture by reverse-phase evaporation," Proc. Natl. Acad. Sci. USA, 1978, pp. 4194-4198, vol. 75, No. 9.
Tan et al., "The Inhibitory Role of CpG Immunostimulatory Motifs in Cationic Lipid Vector-Mediated Transgene Expression in Vivo," Human Gene Therapy, 1999, 10:2153-2161.

Tranchant et al., "Physicochemical optimisation of plasmid delivery by cationic lipids," The Journal of Gene Medicine, 2004, vol. 6, pp. S24-S35.
Usman, N., "Development of siRNA Therapeutics," presented at Nucleic Acids World Symposium, Sep. 16, 2003, Boston, MA; also presented as Zinnan, S., "Moving Towards Therapeutic siRNA," presented at RNA Tools Conference, Oct. 2003, North Carolina, 53 pages.
Van Der Woude, I., et al., "Parameters influencing the introduction of plasmid DNA into cells by the use of synthetic amphiphiles as a carrier system," Biochimica et Biophysica Acta, 1995, pp. 34-40, vol. 1240.
Wilson, R. et al., "Counterion-Induced Condensation of Deoxyribonucleic Acid. A Light-Scattering Study." Biochemistry, 1979, pp. 2192-2196, vol. 18.
Woodle, M.C. et al., "Versatility in lipid compositions showing prolonged circulation with sterically stabilized liposomes," Biochim. Biophys. Acta, 1992, pp. 193-200, vol. 1105.
Zhao et al., "Effect of Different Chemically Modified Oligodeoxynucleotides on Immune Stimulation," Biochemical Pharmacology, 1996, vol. 51, pp. 173-182.
Zhu, N., et al., "Systemic Gene Expression After Intravenous DNA Delivery into Adult Mice," Science, 1993, pp. 209-211, vol. 261.
Zimmermann et al., "RNAi-mediated gene silencing in non-human primates," Nature, 2006, vol. 441, pp. 111-114.
Claims Chart under Exhibit O in the Protest Under 37 CFR § 1.291 filed on Oct. 2, 2009, for U.S. Appl. No. 12/367,439, 6 pages.
Declaration Under 37 CFR § 1.131 of Ian MacLachlan and Adam Judge filed on Jan. 30, 2009, in U.S. Appl. No. 11/592,756, 17 pages.
Declaration Under 37 CFR § 1.132 of Ian MacLachlan and Adam Judge filed on Jan. 30, 2009, in U.S. Appl. No. 11/592,756, 49 pages.
Declaration Under 37 CFR § 1.63 filed on Feb. 28, 2008, in U.S. Appl. No. 11/760,627, 1 page.
Non-Final Office Action mailed on Aug. 17, 2009, in U.S. Appl. No. 11/760,627, 9 pages.
Protest Under 37 CFR § 1.291 filed on Oct. 2, 2009, in U.S. Appl. No. 12/367,439, 17 pages.
Response to Non-Final Office Action filed on Jan. 30, 2009, in U.S. Appl. No. 11/592,756, 27 pages.
Response to Protest Under 37 CFR § 1.291 filed on Dec. 9, 2009, in U.S. Appl. No. 12/367,439, 8 pages.
Response to Restriction Requirement filed on Apr. 23, 2009, in U.S. Appl. No. 11/760,627, 6 pages.
Restriction Requirement mailed on Dec. 23, 2008, in U.S. Appl. No. 11/760,627, 13 pages.
Vigh et al., Does the membrane's physical state control the expression of heat shock and other genes? 1998, Trends in Biochemical Sciences, vol. 23, pp. 369-374.
Mashek et al., Short Communication: Net uptake of nonesterified long chain fatty acids by the perfused caudate lobe of the caprine liver, 2003, Journal of Dairy Science, vol. 86, pp. 1218-1220.
Reynolds et al., Rational siRNA design for RNA interference, 2004, Nature Biotechnology, vol. 22, pp. 326-330.
Madry et al., Efficient lipid-mediated gene transfer to articular chondrocytes, 2000, Gene Therapy, vol. 7, pp. 286-291.
Kiefer et al., Transfection efficiency and cytotoxicity of nonviral gene transfer reagents in human smooth muscle and endothelial cells, Jun. 2004, Pharmaceutical Research, vol. 21, pp. 1009-1017.
Lu et al., In vivo application of RNA interference: From functional genomics to therapeutics, 2005, Advances in Genetics, vol. 54, pp. 117-142.
Sioud, siRNA delivery in vivo, 2005, Methods in Molecular Biology, vol. 309, pp. 237-249.

* cited by examiner

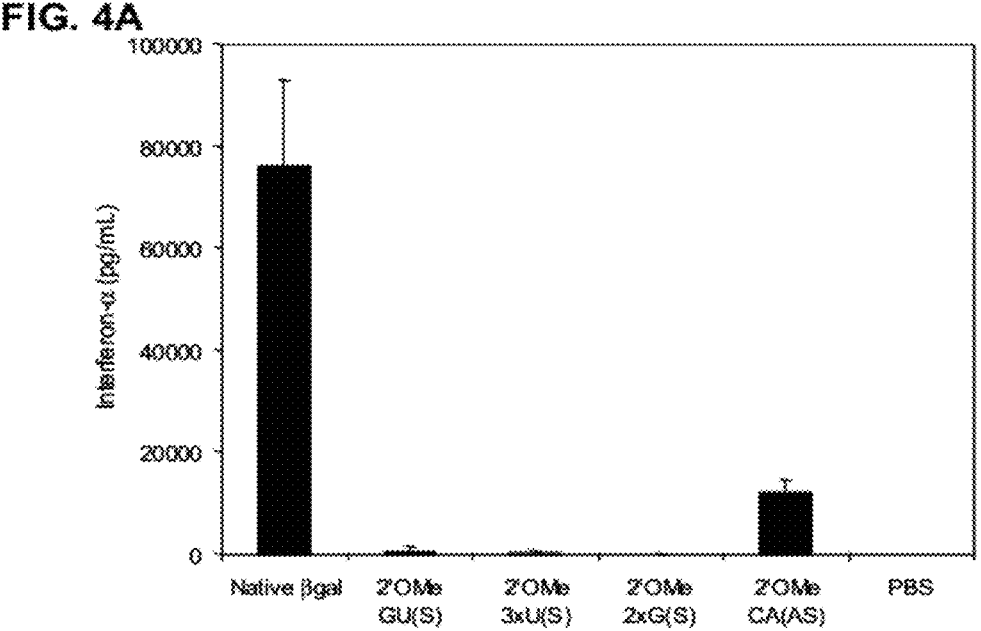
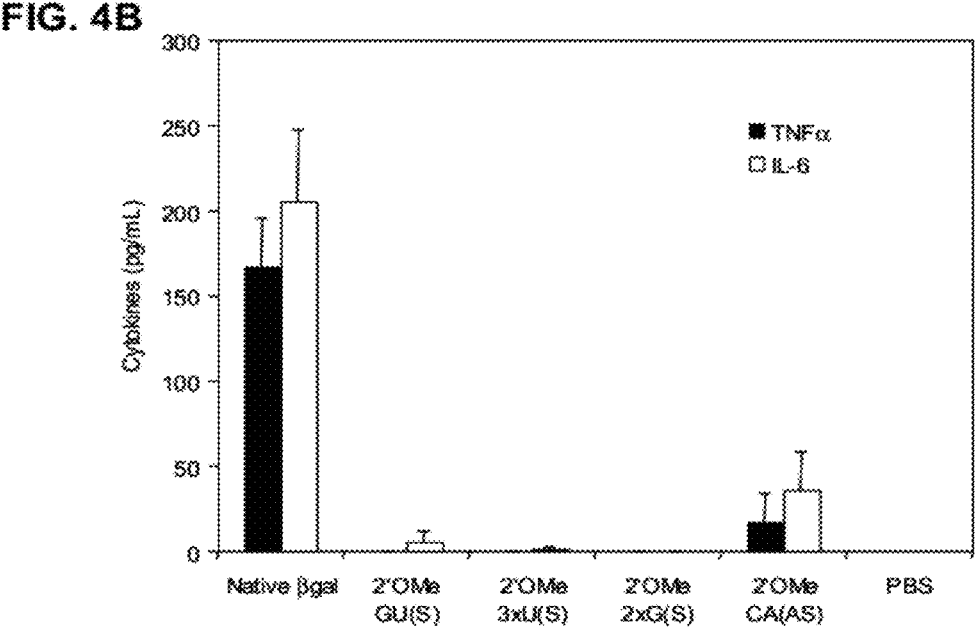

```
                     SEQUENCE LISTING

<160> NUMBER OF SEQ ID NOS: 87

<210> SEQ ID NO 1
<211> LENGTH: 14
<212> TYPE: RNA
<213> ORGANISM: Artificial Sequence
<220> FEATURE:
<223> OTHER INFORMATION: seven 5'-GU-3' motifs from unmodified
      immunostimulatory siRNA
<220> FEATURE:
<221> NAME/KEY: modified_base
<222> LOCATION: (3)...(14)
<223> OTHER INFORMATION: 5'-GU-3' motifs from positions 3 through 14 may
      be present or absent

<400> SEQUENCE: 1
gugugugugu gugu                                                          14

<210> SEQ ID NO 2
<211> LENGTH: 21
<212> TYPE: RNA
<213> ORGANISM: Artificial Sequence
<220> FEATURE:
<223> OTHER INFORMATION: beta-galactosidase (beta-gal) native sense
      strand siRNA

<400> SEQUENCE: 2
uugauguguu uagucgcuau u                                                  21

<210> SEQ ID NO 3
<211> LENGTH: 21
<212> TYPE: RNA
<213> ORGANISM: Artificial Sequence
<220> FEATURE:
<223> OTHER INFORMATION: beta-galactosidase (beta-gal) 2'OMe GU sense
      strand siRNA
<220> FEATURE:
<221> NAME/KEY: modified_base
<222> LOCATION: (5)...(5)
<223> OTHER INFORMATION: n = 2'-O-methyl uridine
<220> FEATURE:
<221> NAME/KEY: modified_base
<222> LOCATION: (6)...(6)
<223> OTHER INFORMATION: n = 2'-O-methyl guanosine
<220> FEATURE:
<221> NAME/KEY: modified_base
<222> LOCATION: (7)...(7)
```

```
<223> OTHER INFORMATION: n = 2'-O-methyl uridine
<220> FEATURE:
<221> NAME/KEY: modified_base
<222> LOCATION: (8)...(8)
<223> OTHER INFORMATION: n = 2'-O-methyl guanosine
<220> FEATURE:
<221> NAME/KEY: modified_base
<222> LOCATION: (9)...(9)
<223> OTHER INFORMATION: n = 2'-O-methyl uridine

<400> SEQUENCE: 3
uugannnnnu uagucgcuau u                                           21

<210> SEQ ID NO 4
<211> LENGTH: 21
<212> TYPE: RNA
<213> ORGANISM: Artificial Sequence
<220> FEATURE:
<223> OTHER INFORMATION: beta-galactosidase (beta-gal) 2'OMe 3xU sense
      strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 4
uugangngnu uagucgcuau u                                           21

<210> SEQ ID NO 5
<211> LENGTH: 21
<212> TYPE: RNA
<213> ORGANISM: Artificial Sequence
<220> FEATURE:
<223> OTHER INFORMATION: beta-galactosidase (beta-gal) 2'OMe 2xG sense
      strand siRNA
<220> FEATURE:
<221> NAME/KEY: modified_base
<222> LOCATION: (1)...(21)
<223> OTHER INFORMATION: n = 2'-O-methyl guanosine

<400> SEQUENCE: 5
uugaununuu uagucgcuau u                                           21

<210> SEQ ID NO 6
<211> LENGTH: 21
<212> TYPE: RNA
<213> ORGANISM: Artificial Sequence
<220> FEATURE:
<223> OTHER INFORMATION: beta-galactosidase (beta-gal) 2'OMe 2xG 3'
      sense strand siRNA
<220> FEATURE:
<221> NAME/KEY: modified_base
<222> LOCATION: (1)...(21)
<223> OTHER INFORMATION: n = 2'-O-methyl guanosine

<400> SEQUENCE: 6
uugauguguu uanucncuau u                                           21

<210> SEQ ID NO 7
<211> LENGTH: 21
<212> TYPE: RNA
<213> ORGANISM: Artificial Sequence
<220> FEATURE:
<223> OTHER INFORMATION: beta-galactosidase (beta-gal) native antisense
      strand  siRNA
<220> FEATURE:
<221> NAME/KEY: modified_base
<222> LOCATION: (1)...(1)
<223> OTHER INFORMATION: n = uridine modified by 5' phosphate

<400> SEQUENCE: 7
```
nagcgacuaa acacaucaau u          21

<210> SEQ ID NO 8
<211> LENGTH: 21
<212> TYPE: RNA
<213> ORGANISM: Artificial Sequence
<220> FEATURE:
<223> OTHER INFORMATION: beta-galactosidase (beta-gal) 2'OMe AC
      antisense strand  siRNA
<220> FEATURE:
<221> NAME/KEY: modified_base
<222> LOCATION: (1)...(1)
<223> OTHER INFORMATION: n = uridine modified by 5'-phosphate
<220> FEATURE:
<221> NAME/KEY: modified_base
<222> LOCATION: (11)...(11)
<223> OTHER INFORMATION: n = 2'-O-methyl adenosine
<220> FEATURE:
<221> NAME/KEY: modified_base
<222> LOCATION: (12)...(12)
<223> OTHER INFORMATION: n = 2'-O-methyl cytosine
<220> FEATURE:
<221> NAME/KEY: modified_base
<222> LOCATION: (13)...(13)
<223> OTHER INFORMATION: n = 2'-O-methyl adenosine
<220> FEATURE:
<221> NAME/KEY: modified_base
<222> LOCATION: (14)...(14)
<223> OTHER INFORMATION: n = 2'-O-methyl cytosine
<220> FEATURE:
<221> NAME/KEY: modified_base
<222> LOCATION: (15)...(15)
<223> OTHER INFORMATION: n = 2'-O-methyl adenosine

<400> SEQUENCE: 8
nagcgacuaa nnnnnucaau u          21

<210> SEQ ID NO 9
<211> LENGTH: 21
<212> TYPE: RNA
<213> ORGANISM: Artificial Sequence
<220> FEATURE:
<223> OTHER INFORMATION: apolipoprotein B (ApoB) native sense strand
      siRNA

<400> SEQUENCE: 9
gucaucacac ugaauaccaa u          21

<210> SEQ ID NO 10
<211> LENGTH: 21
<212> TYPE: RNA
<213> ORGANISM: Artificial Sequence
<220> FEATURE:
<223> OTHER INFORMATION: apolipoprotein B (ApoB) 2'OMe U sense strand
      siRNA
<220> FEATURE:
<221> NAME/KEY: modified_base
<222> LOCATION: (1)...(21)
<223> OTHER INFORMATION: n = 2'-O-methyl uridine

<400> SEQUENCE: 10
gncancacac ngaanaccaa n          21

<210> SEQ ID NO 11
<211> LENGTH: 21
<212> TYPE: RNA
<213> ORGANISM: Artificial Sequence
<220> FEATURE:
<223> OTHER INFORMATION: apolipoprotein B (ApoB) 2'OMe G sense strand
      siRNA
<220> FEATURE:
<221> NAME/KEY: modified_base
<222> LOCATION: (1)...(21)

```
<223> OTHER INFORMATION: n = 2'-O-methyl guanosine

<400> SEQUENCE: 11
nucaucacac unaauaccaa u                                              21

<210> SEQ ID NO 12
<211> LENGTH: 21
<212> TYPE: RNA
<213> ORGANISM: Artificial Sequence
<220> FEATURE:
<223> OTHER INFORMATION: apolipoprotein B (ApoB) 2'OMe C sense strand
      siRNA
<220> FEATURE:
<221> NAME/KEY: modified_base
<222> LOCATION: (1)...(21)
<223> OTHER INFORMATION: n = 2'-O-methyl cytosine

<400> SEQUENCE: 12
gunaunanan ugaauannaa u                                              21

<210> SEQ ID NO 13
<211> LENGTH: 21
<212> TYPE: RNA
<213> ORGANISM: Artificial Sequence
<220> FEATURE:
<223> OTHER INFORMATION: apolipoprotein B (ApoB) 2'OMe A sense strand
      siRNA
<220> FEATURE:
<221> NAME/KEY: modified_base
<222> LOCATION: (1)...(21)
<223> OTHER INFORMATION: n = 2'-O-methyl adenosine

<400> SEQUENCE: 13
gucnucncnc ugnnunccnn u                                              21

<210> SEQ ID NO 14
<211> LENGTH: 23
<212> TYPE: RNA
<213> ORGANISM: Artificial Sequence
<220> FEATURE:
<223> OTHER INFORMATION: apolipoprotein B (ApoB) native antisense strand
      siRNA
<220> FEATURE:
<221> NAME/KEY: modified_base
<222> LOCATION: (1)...(1)
<223> OTHER INFORMATION: n = adenosine modified by 5'-phosphate

<400> SEQUENCE: 14
nuugguauuc agugugauga cac                                            23

<210> SEQ ID NO 15
<211> LENGTH: 23
<212> TYPE: RNA
<213> ORGANISM: Artificial Sequence
<220> FEATURE:
<223> OTHER INFORMATION: apolipoprotein B (ApoB) 2'OMe GU antisense
      strand siRNA
<220> FEATURE:
<221> NAME/KEY: modified_base
<222> LOCATION: (1)...(1)
<223> OTHER INFORMATION: n = adenosine modified by 5'-phosphate
<220> FEATURE:
<221> NAME/KEY: modified_base
<222> LOCATION: (12)...(12)
<223> OTHER INFORMATION: n = 2'-O-methyl guanosine
<220> FEATURE:
<221> NAME/KEY: modified_base
<222> LOCATION: (13)...(13)
<223> OTHER INFORMATION: n = 2'-O-methyl uridine
<220> FEATURE:
<221> NAME/KEY: modified_base
<222> LOCATION: (14)...(14)
```

```
<223> OTHER INFORMATION: n = 2'-O-methyl guanosine
<220> FEATURE:
<221> NAME/KEY: modified_base
<222> LOCATION: (15)...(15)
<223> OTHER INFORMATION: n = 2'-O-methyl uridine
<220> FEATURE:
<221> NAME/KEY: modified_base
<222> LOCATION: (16)...(16)
<223> OTHER INFORMATION: n = 2'-O-methyl guanosine

<400> SEQUENCE: 15
nuugguauuc annnnnauga cac                                              23

<210> SEQ ID NO 16
<211> LENGTH: 23
<212> TYPE: RNA
<213> ORGANISM: Artificial Sequence
<220> FEATURE:
<223> OTHER INFORMATION: apolipoprotein B (ApoB) 2'OMe U antisense
      strand siRNA
<220> FEATURE:
<221> NAME/KEY: modified_base
<222> LOCATION: (1)...(1)
<223> OTHER INFORMATION: n = adenosine modified by 5'-phosphate
<220> FEATURE:
<221> NAME/KEY: modified_base
<222> LOCATION: (2)...(23)
<223> OTHER INFORMATION: n = 2'-O-methyl uridine

<400> SEQUENCE: 16
nnnggnannc agngnganga cac                                              23

<210> SEQ ID NO 17
<211> LENGTH: 23
<212> TYPE: RNA
<213> ORGANISM: Artificial Sequence
<220> FEATURE:
<223> OTHER INFORMATION: apolipoprotein B (ApoB) 2'OMe G antisense
      strand siRNA
<220> FEATURE:
<221> NAME/KEY: modified_base
<222> LOCATION: (1)...(1)
<223> OTHER INFORMATION: n = adenosine modified by 5'-phosphate
<220> FEATURE:
<221> NAME/KEY: modified_base
<222> LOCATION: (2)...(23)
<223> OTHER INFORMATION: n = 2'-O-methyl guanosine

<400> SEQUENCE: 17
nuunnuauuc anununauna cac                                              23

<210> SEQ ID NO 18
<211> LENGTH: 21
<212> TYPE: RNA
<213> ORGANISM: Artificial Sequence
<220> FEATURE:
<223> OTHER INFORMATION: apolipoprotein B mismatch (ApoB mismatch)
      native sense strand siRNA

<400> SEQUENCE: 18
gugaucagac ucaauacgaa u                                                21

<210> SEQ ID NO 19
<211> LENGTH: 21
<212> TYPE: RNA
<213> ORGANISM: Artificial Sequence
<220> FEATURE:
<223> OTHER INFORMATION: apolipoprotein B mismatch (ApoB mismatch) 2'OMe
      U sense strand siRNA
<220> FEATURE:
<221> NAME/KEY: modified_base
<222> LOCATION: (1)...(21)
```

-continued

<223> OTHER INFORMATION: n = 2'-O-methyl uridine

<400> SEQUENCE: 19
gngancagac ncaanacgaa n                                           21

<210> SEQ ID NO 20
<211> LENGTH: 23
<212> TYPE: RNA
<213> ORGANISM: Artificial Sequence
<220> FEATURE:
<223> OTHER INFORMATION: apolipoprotein B mismatch (ApoB mismatch)
      native antisense strand siRNA
<220> FEATURE:
<221> NAME/KEY: modified_base
<222> LOCATION: (1)...(1)
<223> OTHER INFORMATION: n = adenosine modified by 5'-phosphate

<400> SEQUENCE: 20
nuucguauug agucugauca cac                                         23

<210> SEQ ID NO 21
<211> LENGTH: 23
<212> TYPE: RNA
<213> ORGANISM: Artificial Sequence
<220> FEATURE:
<223> OTHER INFORMATION: apolipoprotein B mismatch (ApoB mismatch) 2'OMe
      GU antisense strand siRNA
<220> FEATURE:
<221> NAME/KEY: modified_base
<222> LOCATION: (1)...(1)
<223> OTHER INFORMATION: n = adenosine modified by 5'-phosphate
<220> FEATURE:
<221> NAME/KEY: modified_base
<222> LOCATION: (12)...(12)
<223> OTHER INFORMATION: n = 2'-O-methyl guanosine
<220> FEATURE:
<221> NAME/KEY: modified_base
<222> LOCATION: (13)...(13)
<223> OTHER INFORMATION: n = 2'-O-methyl uridine
<220> FEATURE:
<221> NAME/KEY: modified_base
<222> LOCATION: (14)...(14)
<223> OTHER INFORMATION: n = 2'-O-methyl cytosine
<220> FEATURE:
<221> NAME/KEY: modified_base
<222> LOCATION: (15)...(15)
<223> OTHER INFORMATION: n = 2'-O-methyl uridine
<220> FEATURE:
<221> NAME/KEY: modified_base
<222> LOCATION: (16)...(16)
<223> OTHER INFORMATION: n = 2'-O-methyl guanosine

<400> SEQUENCE: 21
nuucguauug annnnnauca cac                                         23

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:vFLIP
      native sense strand siRNA
<220> FEATURE:
<223> OTHER INFORMATION: vFLIP native sense strand siRNA

<400> SEQUENCE: 22
gugguauugu uccuccuaat t                                           21

<210> SEQ ID NO 23
<211> LENGTH: 21
<212> TYPE: DNA
<213> ORGANISM: Artificial Sequence

```
<220> FEATURE:
<223> OTHER INFORMATION: Description of Combined DNA/RNA Molecule:vFLIP
      2'OMe GU sense strand siRNA
<220> FEATURE:
<223> OTHER INFORMATION: vFLIP 2'OMe GU sense strand siRNA
<220> FEATURE:
<221> NAME/KEY: modified_base
<222> LOCATION: (1)...(1)
<223> OTHER INFORMATION: n = 2'-O-methyl guanosine
<220> FEATURE:
<221> NAME/KEY: modified_base
<222> LOCATION: (2)...(2)
<223> OTHER INFORMATION: n = 2'-O-methyl uridine
<220> FEATURE:
<221> NAME/KEY: modified_base
<222> LOCATION: (3)...(4)
<223> OTHER INFORMATION: n = 2'-O-methyl guanosine
<220> FEATURE:
<221> NAME/KEY: modified_base
<222> LOCATION: (5)...(8)
<223> OTHER INFORMATION: n = 2'-O-methyl uridine
<220> FEATURE:
<221> NAME/KEY: modified_base
<222> LOCATION: (9)...(9)
<223> OTHER INFORMATION: n = 2'-O-methyl guanosine
<220> FEATURE:
<221> NAME/KEY: modified_base
<222> LOCATION: (10)...(11)
<223> OTHER INFORMATION: n = 2'-O-methyl uridine

<400> SEQUENCE: 23
nnnnnannnn nccuccuaat t                                         21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:vFLIP
      2'OMe U sense strand siRNA
<220> FEATURE:
<223> OTHER INFORMATION: vFLIP 2'OMe U sense strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 24
gnggnanngn nccnccnaat t                                         21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:vFLIP
      native antisense strand siRNA
<220> FEATURE:
<223> OTHER INFORMATION: vFLIP native antisense strand siRNA
<220> FEATURE:
<221> NAME/KEY: modified_base
<222> LOCATION: (1)...(1)
<223> OTHER INFORMATION: n = uridine modified by 5'-phosphate

<400> SEQUENCE: 25
nuaggaggaa caauaccact t                                         21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:vFLIP
      2'OMe U antisense strand siRNA
```

```
<220> FEATURE:
<223> OTHER INFORMATION: vFLIP 2'OMe U antisense strand siRNA
<220> FEATURE:
<221> NAME/KEY: modified_base
<222> LOCATION: (1)...(1)
<223> OTHER INFORMATION: n = 2'-O-methyl uridine modified by
      5'-phosphate
<220> FEATURE:
<221> NAME/KEY: modified_base
<222> LOCATION: (2)...(21)
<223> OTHER INFORMATION: n = 2'-O-methyl uridine

<400> SEQUENCE: 26
nnaggaggaa caanaccact t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:vFLIP
      2'OMe C antisense strand siRNA
<220> FEATURE:
<223> OTHER INFORMATION: vFLIP 2'OMe C antisense strand siRNA
<220> FEATURE:
<221> NAME/KEY: modified_base
<222> LOCATION: (1)...(1)
<223> OTHER INFORMATION: n = uridine modified by 5'-phosphate
<220> FEATURE:
<221> NAME/KEY: modified_base
<222> LOCATION: (2)...(21)
<223> OTHER INFORMATION: n = 2'-O-methyl cytidine

<400> SEQUENCE: 27
nuaggaggaa naauannant t                                              21

<210> SEQ ID NO 28
<211> LENGTH: 21
<212> TYPE: RNA
<213> ORGANISM: Artificial Sequence
<220> FEATURE:
<223> OTHER INFORMATION: beta-gal 728 native sense strand siRNA

<400> SEQUENCE: 28
cuacacaaau cagcgauuuu u                                              21

<210> SEQ ID NO 29
<211> LENGTH: 21
<212> TYPE: RNA
<213> ORGANISM: Artificial Sequence
<220> FEATURE:
<223> OTHER INFORMATION: beta-gal 728 2'OMe U sense strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 29
cnacacaaan cagcgannnu u                                              21

<210> SEQ ID NO 30
<211> LENGTH: 21
<212> TYPE: RNA
<213> ORGANISM: Artificial Sequence
<220> FEATURE:
<223> OTHER INFORMATION: beta-gal 728 2'OMe G sense strand siRNA
<220> FEATURE:
<221> NAME/KEY: modified_base
<222> LOCATION: (1)...(21)
<223> OTHER INFORMATION: n = 2'-O-methyl guanosine

<400> SEQUENCE: 30
```
cuacacaaau cancnauuuu u    21

<210> SEQ ID NO 31
<211> LENGTH: 21
<212> TYPE: RNA
<213> ORGANISM: Artificial Sequence
<220> FEATURE:
<223> OTHER INFORMATION: beta-gal 728 2'OMe C sense strand siRNA
<220> FEATURE:
<221> NAME/KEY: modified_base
<222> LOCATION: (1)...(21)
<223> OTHER INFORMATION: n = 2'-O-methyl cytidine

<400> SEQUENCE: 31
nuananaaau nagngauuuu u    21

<210> SEQ ID NO 32
<211> LENGTH: 21
<212> TYPE: RNA
<213> ORGANISM: Artificial Sequence
<220> FEATURE:
<223> OTHER INFORMATION: beta-gal 728 2'OMe A sense strand siRNA
<220> FEATURE:
<221> NAME/KEY: modified_base
<222> LOCATION: (1)...(21)
<223> OTHER INFORMATION: n = 2'-O-methyl adenosine

<400> SEQUENCE: 32
cuncncnnnu cngcgnuuuu u    21

<210> SEQ ID NO 33
<211> LENGTH: 21
<212> TYPE: RNA
<213> ORGANISM: Artificial Sequence
<220> FEATURE:
<223> OTHER INFORMATION: beta-gal 728 native antisense strand siRNA
<220> FEATURE:
<221> NAME/KEY: modified_base
<222> LOCATION: (1)...(1)
<223> OTHER INFORMATION: n = adenosine modified by 5'-phosphate

<400> SEQUENCE: 33
naaucgcuga uuuguguagu u    21

<210> SEQ ID NO 34
<211> LENGTH: 21
<212> TYPE: RNA
<213> ORGANISM: Artificial Sequence
<220> FEATURE:
<223> OTHER INFORMATION: luciferase (Luc) native sense strand siRNA

<400> SEQUENCE: 34
gauuaugucc gguuauguau u    21

<210> SEQ ID NO 35
<211> LENGTH: 21
<212> TYPE: RNA
<213> ORGANISM: Artificial Sequence
<220> FEATURE:
<223> OTHER INFORMATION: luciferase (Luc) 2'OMe U sense strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 35
gannangncc ggnnangnau u    21

```
<210> SEQ ID NO 36
<211> LENGTH: 21
<212> TYPE: RNA
<213> ORGANISM: Artificial Sequence
<220> FEATURE:
<223> OTHER INFORMATION: luciferase (Luc) native antisense strand siRNA
<220> FEATURE:
<221> NAME/KEY: modified_base
<222> LOCATION: (1)...(1)
<223> OTHER INFORMATION: n = uridine modified by 5'-phosphate

<400> SEQUENCE: 36
nacauaaccg gacauaaucu u                                              21

<210> SEQ ID NO 37
<211> LENGTH: 21
<212> TYPE: RNA
<213> ORGANISM: Artificial Sequence
<220> FEATURE:
<223> OTHER INFORMATION: cyclophilin B (Cyp B) native sense strand siRNA

<400> SEQUENCE: 37
ggaaagacug uuccaaaaau u                                              21

<210> SEQ ID NO 38
<211> LENGTH: 21
<212> TYPE: RNA
<213> ORGANISM: Artificial Sequence
<220> FEATURE:
<223> OTHER INFORMATION: cyclophilin B (Cyp B) 2'OMe U sense strand
      siRNA
<220> FEATURE:
<221> NAME/KEY: modified_base
<222> LOCATION: (1)...(21)
<223> OTHER INFORMATION: n = 2'-O-methyl uridine

<400> SEQUENCE: 38
ggaaagacng nnccaaaaau u                                              21

<210> SEQ ID NO 39
<211> LENGTH: 21
<212> TYPE: RNA
<213> ORGANISM: Artificial Sequence
<220> FEATURE:
<223> OTHER INFORMATION: cyclophilin B (Cyp B) antisense strand siRNA
<220> FEATURE:
<221> NAME/KEY: modified_base
<222> LOCATION: (1)...(1)
<223> OTHER INFORMATION: n = uridine modified by 5'-phosphate

<400> SEQUENCE: 39
nuuuuggaac agucuuuccu u                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:NP1496
      native sense strand siRNA
<220> FEATURE:
<223> OTHER INFORMATION: NP1496 native sense strand siRNA

<400> SEQUENCE: 40
ggaucuuauu ucuucggagt t                                              21

<210> SEQ ID NO 41
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:NP1496
      2'OMe U sense strand siRNA
<220> FEATURE:
<223> OTHER INFORMATION: NP1496 2'OMe U sense strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 41
ggancunaun ucnucggagt t                                             21

<210> SEQ ID NO 42
<211> LENGTH: 21
<212> TYPE: DNA
<213> ORGANISM: Artificial Sequence
<220> FEATURE:
<223> OTHER INFORMATION: Description of Combined DNA/RNA Molecule:NP1496
      native antisense strand siRNA
<220> FEATURE:
<223> OTHER INFORMATION: NP1496 native antisense strand siRNA
<220> FEATURE:
<221> NAME/KEY: modified_base
<222> LOCATION: (1)...(1)
<223> OTHER INFORMATION: n = cytidine modified by 5'-phosphate

<400> SEQUENCE: 42
nuccgaagaa auaagaucct t                                             21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:PA2087
      native sense strand siRNA
<220> FEATURE:
<223> OTHER INFORMATION: PA2087 native sense strand siRNA

<400> SEQUENCE: 43
gcaauugagg agugccugat t                                             21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:PA2087
      2'OMe U sense strand siRNA
<220> FEATURE:
<223> OTHER INFORMATION: PA2087 2'OMe U sense strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 44
gcaanngagg agngccngat t                                             21

<210> SEQ ID NO 45
<211> LENGTH: 21
<212> TYPE: DNA
<213> ORGANISM: Artificial Sequence
<220> FEATURE:
<223> OTHER INFORMATION: Description of Combined DNA/RNA Molecule:PA2087
      native antisense strand siRNA
<220> FEATURE:
<223> OTHER INFORMATION: PA2087 native antisense strand siRNA
<220> FEATURE:
<221> NAME/KEY: modified_base
<222> LOCATION: (1)...(1)
```

```
<223> OTHER INFORMATION: n = uridine modified by 5'-phosphate

<400> SEQUENCE: 45
ncaggcacuc cucaauugct t                                              21

<210> SEQ ID NO 46
<211> LENGTH: 21
<212> TYPE: RNA
<213> ORGANISM: Artificial Sequence
<220> FEATURE:
<223> OTHER INFORMATION: apolipoprotein B (ApoB) 10048 sense strand
      siRNA

<400> SEQUENCE: 46 agugcauca cacugaauac c                                               21

<210> SEQ ID NO 47
<211> LENGTH: 21
<212> TYPE: RNA
<213> ORGANISM: Artificial Sequence
<220> FEATURE:
<223> OTHER INFORMATION: apolipoprotein B (ApoB) 10048 antisense strand
      siRNA

<400> SEQUENCE: 47
uauucagugu gaugacacuu g                                              21

<210> SEQ ID NO 48
<211> LENGTH: 21
<212> TYPE: RNA
<213> ORGANISM: Artificial Sequence
<220> FEATURE:
<223> OTHER INFORMATION: apolipoprotein B (ApoB) 10048 U2 G1 sense
      strand siRNA
<220> FEATURE:
<221> NAME/KEY: modified_base
<222> LOCATION: (3)...(8)
<223> OTHER INFORMATION: n = 2'-O-methyl uridine
<220> FEATURE:
<221> NAME/KEY: modified_base
<222> LOCATION: (15)...(15)
<223> OTHER INFORMATION: n = 2'-O-methyl guanosine

<400> SEQUENCE: 48
agngucanca cacunaauac c                                              21

<210> SEQ ID NO 49
<211> LENGTH: 21
<212> TYPE: RNA
<213> ORGANISM: Artificial Sequence
<220> FEATURE:
<223> OTHER INFORMATION: apolipoprotein B (ApoB) 10048 U4 antisense
      strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 49
uauncagngn gaugacacnu g                                              21

<210> SEQ ID NO 50
<211> LENGTH: 21
<212> TYPE: RNA
<213> ORGANISM: Artificial Sequence
<220> FEATURE:
<223> OTHER INFORMATION: apolipoprotein B (ApoB) 10048 U2 G1 sense
      strand siRNA
<220> FEATURE:
<221> NAME/KEY: modified_base
```

```
<222> LOCATION: (4)...(4)
<223> OTHER INFORMATION: n = 2'-O-methyl guanosine
<220> FEATURE:
<221> NAME/KEY: modified_base
<222> LOCATION: (8)...(15)
<223> OTHER INFORMATION: n = 2'-O-methyl uridine

<400> SEQUENCE: 50
agunucanca cacngaauac c                                              21

<210> SEQ ID NO 51
<211> LENGTH: 21
<212> TYPE: RNA
<213> ORGANISM: Artificial Sequence
<220> FEATURE:
<223> OTHER INFORMATION: apolipoprotein B (ApoB) 10048 U2 G2 antisense
      strand siRNA
<220> FEATURE:
<221> NAME/KEY: modified_base
<222> LOCATION: (4)...(4)
<223> OTHER INFORMATION: n = 2'-O-methyl uridine
<220> FEATURE:
<221> NAME/KEY: modified_base
<222> LOCATION: (7)...(9)
<223> OTHER INFORMATION: n = 2'-O-methyl guanosine
<220> FEATURE:
<221> NAME/KEY: modified_base
<222> LOCATION: (19)...(19)
<223> OTHER INFORMATION: n = 2'-O-methyl uridine

<400> SEQUENCE: 51
uauncanunu gaugacacnu g                                              21

<210> SEQ ID NO 52
<211> LENGTH: 21
<212> TYPE: RNA
<213> ORGANISM: Artificial Sequence
<220> FEATURE:
<223> OTHER INFORMATION: apolipoprotein B (ApoB) 10048 U5 sense strand
      siRNA
<220> FEATURE:
<221> NAME/KEY: modified_base
<222> LOCATION: (1)...(21)
<223> OTHER INFORMATION: n = 2'-O-methyl uridine

<400> SEQUENCE: 52
agngncanca cacngaanac c                                              21

<210> SEQ ID NO 53
<211> LENGTH: 21
<212> TYPE: RNA
<213> ORGANISM: Artificial Sequence
<220> FEATURE:
<223> OTHER INFORMATION: apolipoprotein B (ApoB) 10048 U3 antisense
      strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 53
uauucagngu gangacacnu g                                              21

<210> SEQ ID NO 54
<211> LENGTH: 21
<212> TYPE: RNA
<213> ORGANISM: Artificial Sequence
<220> FEATURE:
<223> OTHER INFORMATION: apolipoprotein B (ApoB) 10048 U5 antisense
      strand siRNA
<220> FEATURE:
<221> NAME/KEY: modified_base
```

<222> LOCATION: (1)...(21)
<223> OTHER INFORMATION: n = 2'-O-methyl uridine

<400> SEQUENCE: 54
uauncagngn gangacacnu g                                              21

<210> SEQ ID NO 55
<211> LENGTH: 21
<212> TYPE: RNA
<213> ORGANISM: Artificial Sequence
<220> FEATURE:
<223> OTHER INFORMATION: apolipoprotein B (ApoB) 10048 U2 G3 sense
      strand siRNA
<220> FEATURE:
<221> NAME/KEY: modified_base
<222> LOCATION: (2)...(4)
<223> OTHER INFORMATION: n = 2'-O-methyl guanosine
<220> FEATURE:
<221> NAME/KEY: modified_base
<222> LOCATION: (8)...(8)
<223> OTHER INFORMATION: n = 2'-O-methyl uridine
<220> FEATURE:
<221> NAME/KEY: modified_base
<222> LOCATION: (15)...(15)
<223> OTHER INFORMATION: n = 2'-O-methyl guanosine
<220> FEATURE:
<221> NAME/KEY: modified_base
<222> LOCATION: (18)...(18)
<223> OTHER INFORMATION: n = 2'-O-methyl uridine

<400> SEQUENCE: 55
anunucanca cacunaanac c                                              21

<210> SEQ ID NO 56
<211> LENGTH: 21
<212> TYPE: RNA
<213> ORGANISM: Artificial Sequence
<220> FEATURE:
<223> OTHER INFORMATION: apolipoprotein B (ApoB) 10048 U2 G3 antisense
      strand siRNA
<220> FEATURE:
<221> NAME/KEY: modified_base
<222> LOCATION: (4)...(4)
<223> OTHER INFORMATION: n = 2'-O-methyl uridine
<220> FEATURE:
<221> NAME/KEY: modified_base
<222> LOCATION: (7)...(11)
<223> OTHER INFORMATION: n = 2'-O-methyl guanosine
<220> FEATURE:
<221> NAME/KEY: modified_base
<222> LOCATION: (19)...(19)
<223> OTHER INFORMATION: n = 2'-O-methyl uridine

<400> SEQUENCE: 56
uauncanunu naugacacnu g                                              21

<210> SEQ ID NO 57
<211> LENGTH: 21
<212> TYPE: RNA
<213> ORGANISM: Artificial Sequence
<220> FEATURE:
<223> OTHER INFORMATION: apolipoprotein B (ApoB) 10048 U5 G2 sense
      strand siRNA
<220> FEATURE:
<221> NAME/KEY: modified_base
<222> LOCATION: (2)...(2)
<223> OTHER INFORMATION: n = 2'-O-methyl guanosine
<220> FEATURE:
<221> NAME/KEY: modified_base
<222> LOCATION: (3)...(3)
<223> OTHER INFORMATION: n = 2'-O-methyl uridine
<220> FEATURE:
<221> NAME/KEY: modified_base
<222> LOCATION: (4)...(4)

```
<223> OTHER INFORMATION: n = 2'-O-methyl guanosine
<220> FEATURE:
<221> NAME/KEY: modified_base
<222> LOCATION: (5)...(18)
<223> OTHER INFORMATION: n = 2'-O-methyl uridine

<400> SEQUENCE: 57
annnncanca cacngaaanac c                                            21

<210> SEQ ID NO 58
<211> LENGTH: 21
<212> TYPE: RNA
<213> ORGANISM: Artificial Sequence
<220> FEATURE:
<223> OTHER INFORMATION: apolipoprotein B (ApoB) 10048 U4 G4 antisense
      strand siRNA
<220> FEATURE:
<221> NAME/KEY: modified_base
<222> LOCATION: (4)...(4)
<223> OTHER INFORMATION: n = 2'-O-methyl uridine
<220> FEATURE:
<221> NAME/KEY: modified_base
<222> LOCATION: (7)...(7)
<223> OTHER INFORMATION: n = 2'-O-methyl guanosine
<220> FEATURE:
<221> NAME/KEY: modified_base
<222> LOCATION: (8)...(8)
<223> OTHER INFORMATION: n = 2'-O-methyl uridine
<220> FEATURE:
<221> NAME/KEY: modified_base
<222> LOCATION: (9)...(9)
<223> OTHER INFORMATION: n = 2'-O-methyl guanosine
<220> FEATURE:
<221> NAME/KEY: modified_base
<222> LOCATION: (10)...(10)
<223> OTHER INFORMATION: n = 2'-O-methyl uridine
<220> FEATURE:
<221> NAME/KEY: modified_base
<222> LOCATION: (11)...(14)
<223> OTHER INFORMATION: n = 2'-O-methyl guanosine
<220> FEATURE:
<221> NAME/KEY: modified_base
<222> LOCATION: (19)...(19)
<223> OTHER INFORMATION: n = 2'-O-methyl uridine

<400> SEQUENCE: 58
uauncannnn naunacacnu g                                             21

<210> SEQ ID NO 59
<211> LENGTH: 21
<212> TYPE: RNA
<213> ORGANISM: Artificial Sequence
<220> FEATURE:
<223> OTHER INFORMATION: apolipoprotein B (ApoB) 10048 U5 G1 sense
      strand siRNA
<220> FEATURE:
<221> NAME/KEY: modified_base
<222> LOCATION: (3)...(14)
<223> OTHER INFORMATION: n = 2'-O-methyl uridine
<220> FEATURE:
<221> NAME/KEY: modified_base
<222> LOCATION: (15)...(15)
<223> OTHER INFORMATION: n = 2'-O-methyl guanosine
<220> FEATURE:
<221> NAME/KEY: modified_base
<222> LOCATION: (18)...(18)
<223> OTHER INFORMATION: n = 2'-O-methyl uridine

<400> SEQUENCE: 59
agngncanca cacnnaaanac c                                            21

<210> SEQ ID NO 60
<211> LENGTH: 21
<212> TYPE: RNA
```

```
<213> ORGANISM: Artificial Sequence
<220> FEATURE:
<223> OTHER INFORMATION: apolipoprotein B (ApoB) 10048 U7 G2 antisense
      strand siRNA
<220> FEATURE:
<221> NAME/KEY: modified_base
<222> LOCATION: (3)...(8)
<223> OTHER INFORMATION: n = 2'-O-methyl uridine
<220> FEATURE:
<221> NAME/KEY: modified_base
<222> LOCATION: (9)...(9)
<223> OTHER INFORMATION: n = 2'-O-methyl guanosine
<220> FEATURE:
<221> NAME/KEY: modified_base
<222> LOCATION: (10)...(13)
<223> OTHER INFORMATION: n = 2'-O-methyl uridine
<220> FEATURE:
<221> NAME/KEY: modified_base
<222> LOCATION: (14)...(14)
<223> OTHER INFORMATION: n = 2'-O-methyl guanosine
<220> FEATURE:
<221> NAME/KEY: modified_base
<222> LOCATION: (19)...(20)
<223> OTHER INFORMATION: n = 2'-O-methyl uridine

<400> SEQUENCE: 60
uanncagnnn gannacacnn g                                             21

<210> SEQ ID NO 61
<211> LENGTH: 21
<212> TYPE: RNA
<213> ORGANISM: Artificial Sequence
<220> FEATURE:
<223> OTHER INFORMATION: apolipoprotein B (ApoB) 10086 sense strand
      siRNA

<400> SEQUENCE: 61
acacuaagaa ccagaagauc a                                             21

<210> SEQ ID NO 62
<211> LENGTH: 21
<212> TYPE: RNA
<213> ORGANISM: Artificial Sequence
<220> FEATURE:
<223> OTHER INFORMATION: apolipoprotein B (ApoB) 10086 antisense strand
      siRNA

<400> SEQUENCE: 62
aucuucuggu ucuuaguguu a                                             21

<210> SEQ ID NO 63
<211> LENGTH: 21
<212> TYPE: RNA
<213> ORGANISM: Artificial Sequence
<220> FEATURE:
<223> OTHER INFORMATION: apolipoprotein B (ApoB) 10086 U1 G2 sense
      strand siRNA
<220> FEATURE:
<221> NAME/KEY: modified_base
<222> LOCATION: (5)...(5)
<223> OTHER INFORMATION: n = 2'-O-methyl uridine
<220> FEATURE:
<221> NAME/KEY: modified_base
<222> LOCATION: (8)...(14)
<223> OTHER INFORMATION: n = 2'-O-methyl guanosine

<400> SEQUENCE: 63
acacnaanaa ccanaagauc a                                             21

<210> SEQ ID NO 64
<211> LENGTH: 21
<212> TYPE: RNA
```

```
<213> ORGANISM: Artificial Sequence
<220> FEATURE:
<223> OTHER INFORMATION: apolipoprotein B (ApoB) 10086 U3 G1 antisense
      strand siRNA
<220> FEATURE:
<221> NAME/KEY: modified_base
<222> LOCATION: (5)...(5)
<223> OTHER INFORMATION: n = 2'-O-methyl uridine
<220> FEATURE:
<221> NAME/KEY: modified_base
<222> LOCATION: (9)...(9)
<223> OTHER INFORMATION: n = 2'-O-methyl guanosine
<220> FEATURE:
<221> NAME/KEY: modified_base
<222> LOCATION: (11)...(17)
<223> OTHER INFORMATION: n = 2'-O-methyl uridine

<400> SEQUENCE: 64
aucuncugnu ncuuagnguu a                                              21

<210> SEQ ID NO 65
<211> LENGTH: 21
<212> TYPE: RNA
<213> ORGANISM: Artificial Sequence
<220> FEATURE:
<223> OTHER INFORMATION: apolipoprotein B (ApoB) 10346 sense strand
      siRNA

<400> SEQUENCE: 65
auggaaauac caagucaaaa c                                              21

<210> SEQ ID NO 66
<211> LENGTH: 21
<212> TYPE: RNA
<213> ORGANISM: Artificial Sequence
<220> FEATURE:
<223> OTHER INFORMATION: apolipoprotein B (ApoB) 10346 antisense strand
      siRNA

<400> SEQUENCE: 66
uuugacuugg uauuccauu a                                               21

<210> SEQ ID NO 67
<211> LENGTH: 21
<212> TYPE: RNA
<213> ORGANISM: Artificial Sequence
<220> FEATURE:
<223> OTHER INFORMATION: apolipoprotein B (ApoB) 10346 U3 sense strand
      siRNA
<220> FEATURE:
<221> NAME/KEY: modified_base
<222> LOCATION: (1)...(21)
<223> OTHER INFORMATION: n = 2'-O-methyl uridine

<400> SEQUENCE: 67
anggaaanac caagncaaaa c                                              21

<210> SEQ ID NO 68
<211> LENGTH: 21
<212> TYPE: RNA
<213> ORGANISM: Artificial Sequence
<220> FEATURE:
<223> OTHER INFORMATION: apolipoprotein B (ApoB) 10346 U4 antisense
      strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 68
uungacungg naunccauu a                                               21
```

<210> SEQ ID NO 69
<211> LENGTH: 21
<212> TYPE: DNA
<213> ORGANISM: Artificial Sequence
<220> FEATURE:
<223> OTHER INFORMATION: Description of Combined DNA/RNA Molecule:
      mitotic kinesin Eg5 2263 sense strand siRNA
<220> FEATURE:
<223> OTHER INFORMATION: mitotic kinesin Eg5 2263 sense strand siRNA

<400> SEQUENCE: 69
cugaagaccu gaagacaaut t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Combined DNA/RNA Molecule:
      mitotic kinesin Eg5 2263 antisense strand siRNA
<220> FEATURE:
<223> OTHER INFORMATION: mitotic kinesin Eg5 2263 antisense strand siRNA

<400> SEQUENCE: 70
auugucuuca ggucuucagt t                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Combined DNA/RNA Molecule:
      mitotic kinesin Eg5 2263 U sense strand siRNA
<220> FEATURE:
<223> OTHER INFORMATION: mitotic kinesin Eg5 2263 U sense strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 71
cngaagaccn gaagacaant t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Combined DNA/RNA Molecule:
      mitotic kinesin Eg5 2263 G sense strand siRNA
<220> FEATURE:
<223> OTHER INFORMATION: mitotic kinesin Eg5 2263 G sense strand siRNA
<220> FEATURE:
<221> NAME/KEY: modified_base
<222> LOCATION: (1)...(21)
<223> OTHER INFORMATION: n = 2'-O-methyl guanosine

<400> SEQUENCE: 72
cunaanaccu naanacaaut t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Combined DNA/RNA Molecule:
      mitotic kinesin Eg5 2263 U antisense strand siRNA
<220> FEATURE:
<223> OTHER INFORMATION: mitotic kinesin Eg5 2263 U antisense strand
      siRNA

```
<220> FEATURE:
<221> NAME/KEY: modified_base
<222> LOCATION: (1)...(21)
<223> OTHER INFORMATION: n = 2'-O-methyl uridine

<400> SEQUENCE: 73
auugucunca ggncuncagt t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Combined DNA/RNA Molecule:
      mitotic kinesin Eg5 2263 G antisense strand siRNA
<220> FEATURE:
<223> OTHER INFORMATION: mitotic kinesin Eg5 2263 G antisense strand
      siRNA
<220> FEATURE:
<221> NAME/KEY: modified_base
<222> LOCATION: (1)...(21)
<223> OTHER INFORMATION: n = 2'-O-methyl guanosine

<400> SEQUENCE: 74
auunucuuca gnucuucant t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 411 sense strand siRNA
<220> FEATURE:
<223> OTHER INFORMATION: influenza nucleocapsid protein (NP) 411 sense
      strand siRNA

<400> SEQUENCE: 75
agcuaauaau ggugacgaut t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 411 antisense strand siRNA
<220> FEATURE:
<223> OTHER INFORMATION: influenza nucleocapsid protein (NP) 411
      antisense strand siRNA

<400> SEQUENCE: 76
aucgucacca uuauuagcut t                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 411 U5 sense strand siRNA
<220> FEATURE:
<223> OTHER INFORMATION: influenza nucleocapsid protein (NP) 411 U5
      sense strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 77
agcnaanaan ggngacgant t                                              21
```

<210> SEQ ID NO 78
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 929 sense strand siRNA
<220> FEATURE:
<223> OTHER INFORMATION: influenza nucleocapsid protein (NP) 929 sense
      strand siRNA

<400> SEQUENCE: 78
gauacucucu agucggaaut t                                           21

<210> SEQ ID NO 79
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 929 antisense strand siRNA
<220> FEATURE:
<223> OTHER INFORMATION: influenza nucleocapsid protein (NP) 929
      antisense strand siRNA

<400> SEQUENCE: 79
auuccgacua gagaguauct t                                           21

<210> SEQ ID NO 80
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 929 U6 sense strand siRNA
<220> FEATURE:
<223> OTHER INFORMATION: influenza nucleocapsid protein (NP) 929 U6
      sense strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 80
ganacncncn agncggaant t                                           21

<210> SEQ ID NO 81
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 1116 sense strand siRNA
<220> FEATURE:
<223> OTHER INFORMATION: influenza nucleocapsid protein (NP) 1116 sense
      strand siRNA

<400> SEQUENCE: 81
gcuuuccacu agaggaguut t                                           21

<210> SEQ ID NO 82
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 1116 antisense strand siRNA
<220> FEATURE:
<223> OTHER INFORMATION: influenza nucleocapsid protein (NP) 1116
      antisense strand siRNA

<400> SEQUENCE: 82
aacuccucua guggaaagct t          21

<210> SEQ ID NO 83
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 1116 U5 sense strand siRNA
<220> FEATURE:
<223> OTHER INFORMATION: influenza nucleocapsid protein (NP) 1116 U5
      sense strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 83
gcnunccacn agaggaguut t          21

<210> SEQ ID NO 84
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 1496 sense strand siRNA
<220> FEATURE:
<223> OTHER INFORMATION: influenza nucleocapsid protein (NP) 1496 sense
      strand siRNA

<400> SEQUENCE: 84
ggaucuuauu ucuucggagt t          21

<210> SEQ ID NO 85
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 1496 antisense strand siRNA
<220> FEATURE:
<223> OTHER INFORMATION: influenza nucleocapsid protein (NP) 1496
      antisense strand siRNA

<400> SEQUENCE: 85
cuccgaagaa auaagaucct t          21

<210> SEQ ID NO 86
<211> LENGTH: 21
<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 1496 U4 sense strand siRNA
<220> FEATURE:
<223> OTHER INFORMATION: influenza nucleocapsid protein (NP) 1496 U4
      sense strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 86
ggancunaun ucnucggagt t          21

<210> SEQ ID NO 87
<211> LENGTH: 21

```
-continued

<212> TYPE: DNA
<213> ORGANISM: Artificial Sequence
<220> FEATURE:
<223> OTHER INFORMATION: Description of Combined DNA/RNA Molecule:
      influenza nucleocapsid protein (NP) 1496 U8 sense strand siRNA
<220> FEATURE:
<223> OTHER INFORMATION: influenza nucleocapsid protein (NP) 1496 U8
      sense strand siRNA
<220> FEATURE:
<221> NAME/KEY: modified_base
<222> LOCATION: (1)...(21)
<223> OTHER INFORMATION: n = 2'-O-methyl uridine

<400> SEQUENCE: 87
ggancnnann ncnncggagt t                                              21
```

MODIFIED SIRNA MOLECULES AND USES THEREOF

CROSS-REFERENCES TO RELATED APPLICATIONS

The present application claims priority to U.S. Provisional Application No. 60/732,964, filed Nov. 2, 2005, U.S. Provisional Application No. 60/817,933, filed Jun. 30, 2006, and is a continuation application of U.S. application Ser. No. 11/592,756, filed Nov. 2, 2006, now U.S. Pat. No. 8,101,741, the disclosures of which are herein incorporated by reference in their entirety for all purposes.

BACKGROUND OF THE INVENTION

RNA interference (RNAi) is an evolutionarily conserved, sequence-specific mechanism triggered by double-stranded RNA (dsRNA) that induces degradation of complementary target single stranded mRNA and "silencing" of the corresponding translated sequences (McManus et al., *Nature Rev. Genet.*, 3:737 (2002)). RNAi functions by enzymatic cleavage of longer dsRNA strands into biologically active "short-interfering RNA" (siRNA) sequences of about 21-23 nucleotides in length (Elbashir et al., *Genes Dev.*, 15:188 (2001)). siRNA can be used to downregulate or silence the transcription and translation of a gene product of interest, i.e., a target sequence.

As part of the innate defense mechanism against invading pathogens, the mammalian immune system is activated by a number of exogenous RNA (Alexopoulou et al., *Nature*, 413:732-738 (2001); Heil et al., *Science*, 303:1526-1529 (2004); Diebold et al., *Science*, 303:1529-1531 (2004)) and DNA species (Krieg, *Ann. Rev. Immunol.*, 20:709-760 (2002)), resulting in the release of interferons and inflammatory cytokines. The consequences of activating this response can be severe, with local and systemic inflammatory reactions potentially leading to toxic shock-like syndromes. These immunotoxicities can be triggered by very low doses of an immunostimulatory agent, particularly in more sensitive species, including humans (Michie et al., *N. Engl. J. Med.*, 318:1481-1486 (1988); Krown et al., *Semin. Oncol.*, 13:207-217 (1986)). It has recently been demonstrated that synthetic siRNA can be a potent activator of the innate immune response when administered with vehicles that facilitate intracellular delivery (Judge et al., *Nat. Biotechnol.*, 23:457-462 (2005); Hornung et al., *Nat. Med.*, 11:263-270 (2005); Sioud, *J. Mol. Biol.*, 348:1079-1090 (2005)). Although still poorly defined, immune recognition of siRNA is sequence dependent and likely activates innate immune cells through the Toll-like receptor-7 (TLR7) pathway, causing potent induction of interferon-alpha (IFN-α) and inflammatory cytokines. Toxicities associated with the administration of siRNA in vivo have been attributed to such a response (Morrissey et al., *Nat. Biotechnol.*, 23:1002-1007 (2005); Judge et al., supra).

Stabilization of synthetic siRNA against rapid nuclease degradation is generally regarded as a prerequisite for in vivo and therapeutic applications. This can be achieved using a variety of stabilization chemistries previously developed for other nucleic acid drugs, such as ribozymes and antisense molecules (Manoharan, *Curr. Opin. Chem. Biol.*, 8:570-579 (2004)). These include chemical modifications to the native 2'-OH group in the ribose sugar backbone, such as 2'-O-methyl (2'OMe) and 2'-Fluoro (2° F.) substitutions that can be readily introduced into siRNA as 2'-modified nucleotides during RNA synthesis. Although a number of reports have demonstrated that chemically stabilized siRNA containing 2'OMe (Czauderna et al., *Nucl. Acids Res.*, 31:2705-2716 (2003); Allerson et al., *J. Med. Chem.*, 48:901-904 (2005); Prakash et al., *J. Med. Chem.*, 48:4247-4253 (2005)), 2° F. (Chiu et al., *RNA*, 9:1034-1048 (2003); Layzer et al., *RNA*, 10:766-771 (2004); Allerson et al., supra; Prakash et al., supra), 2'-deoxy (Chiu et al., supra), or "locked nucleic acid" (LNA) (Hornung et al., supra; Elmen et al., *Nucl. Acids Res.*, 33:439-447 (2005)) modifications can be designed that retain functional RNAi activity, such modifications appear to be tolerated only in certain ill-defined positional or sequence-related contexts. In fact, the introduction of chemical modifications to native siRNA duplexes can, in many cases, have a negative impact on RNAi activity (Hornung et al., supra; Czauderna et al., supra; Prakash et al., supra; Chiu et al., supra; Elmen et al., supra). As a result, the design of chemically modified siRNA has required a stochastic screening approach to identify duplexes that retain potent gene silencing activity.

Poor uptake of exogenous nucleic acids by cells represents an additional barrier to the development of siRNA-based drugs. siRNA can be encapsulated within liposomes termed stable nucleic acid-lipid particles (SNALP), which enhance intracellular uptake of nucleic acids and are suitable for systemic administration. These systems are effective at mediating RNAi in vitro (Judge et al., supra) and have been shown to inhibit viral replication at therapeutically viable siRNA doses in a murine model of hepatitis B (Morrissey et al., supra). However, these studies were performed with synthetic siRNA that included greater than 90% modified nucleotides, which may compromise the potency of RNAi-mediated gene silencing.

Thus, there is a strong need in the art for minimally modified siRNA molecules that abrogate the immunostimulatory activity of siRNA without having a negative impact on RNAi activity. The present invention addresses this and other needs.

SUMMARY OF THE INVENTION

The present invention provides chemically modified siRNA molecules and methods of using such siRNA molecules to silence target gene expression.

The present invention is based, in part, upon the surprising discovery that minimal chemical modifications, such as 2'-O-methyl (2'OMe) modifications, at selective positions within one or both strands of the siRNA duplex are sufficient to reduce or completely abrogate the immunostimulatory activity of siRNA. In certain instances, by restricting chemical modification to the non-targeting sense strand of the siRNA duplex, the immunostimulatory activity of siRNA can be abolished while retaining full RNAi activity. Alternatively, minimal chemical modifications, such as 2'OMe modifications, at selective positions within the sense and antisense strands of the siRNA duplex are sufficient to decrease the immunostimulatory properties of siRNA while retaining RNAi activity. Using Apolipoprotein B (ApoB) and the mitotic kinesin Eg5 as non-limiting examples of endogenous gene targets, potent gene silencing can be achieved in vivo using the modified siRNA molecules of the present invention without cytokine induction, immunotoxicity, or off-target effects associated with immune activation triggered by a corresponding unmodified siRNA sequence. As a result, patients will experience the full benefits of siRNA therapy without suffering any of the immunostimulatory side-effects associated with such therapy.

In one aspect, the present invention provides a modified siRNA comprising a double-stranded region of about 15 to about 60 nucleotides in length (e.g., about 15-60, 15-50, 15-40, 15-30, 15-25, or 19-25 nucleotides in length), wherein the modified siRNA is less immunostimulatory than a corresponding unmodified siRNA sequence and is capable of silencing expression of a target sequence.

Typically, the modified siRNA comprises from about 1% to about 100% (e.g. about 1%, 5%, 10%, 15%, 20%, 25%, 30%, 35%, 40%, 45%, 50%, 55%, 60%, 65%, 70%, 75%, 80%, 85%, 90%, 95%, or 100%) modified nucleotides in the double-stranded region of the siRNA duplex. In preferred embodiments, less than about 20% (e.g., less than about 20%, 15%, 10%, or 5%) or from about 1% to about 20% (e.g., from about 1%-20%, 5%-20%, 10%-20%, or 15%-20%) of the nucleotides in the double-stranded region comprise modified nucleotides. As a non-limiting example, the modified siRNA can contain as few as two 2'OMe-modified nucleotides, representing about 5% of the native 2'-OH positions in the double-stranded region of the siRNA duplex. This minimal degree of chemical modification, when incorporated into highly immunostimulatory siRNA sequences, can reduce or completely abrogate siRNA-mediated interferon and inflammatory cytokine induction in vitro and in vivo (see, Example 1).

In some embodiments, the modified siRNA comprises modified nucleotides including, but not limited to, 2'OMe nucleotides, 2'-deoxy-2'-fluoro (2° F.) nucleotides, 2'-deoxy nucleotides, 2'-O-(2-methoxyethyl) (MOE) nucleotides, locked nucleic acid (LNA) nucleotides, and mixtures thereof. In preferred embodiments, the modified siRNA comprises 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof. In certain instances, the modified siRNA does not comprise 2'OMe-cytosine nucleotides. In other embodiments, the modified siRNA comprises a hairpin loop structure.

The modified siRNA can comprise modified nucleotides in one strand (i.e., sense or antisense) or both strands of the double-stranded region of the siRNA. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% less immunostimulatory than the corresponding unmodified siRNA sequence. Preferably, the modified siRNA is at least about 80% (e.g., 80%, 85%, 90%, 91%, 92%, 93%, 94%, 95%, 96%, 97%, 98%, 99%, or 100%) less immunostimulatory than the corresponding unmodified siRNA sequence. It will be readily apparent to those of skill in the art that the immunostimulatory properties of the modified siRNA molecule and the corresponding unmodified siRNA molecule can be determined by, for example, measuring INF-α and/or IL-6 levels two to twelve hours after systemic administration in a mammal using an appropriate lipid-based delivery system (such as the SNALP delivery system or other lipoplex systems disclosed herein).

In certain embodiments, the modified siRNA has an $IC_{50}$ less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA. In yet other embodiments, the modified siRNA preferably has an $IC_{50}$ less than or equal to two-fold that of the corresponding unmodified siRNA. It will be readily apparent to those of skill in the art that a dose response curve can be generated and the $IC_{50}$ values for the modified siRNA and the corresponding unmodified siRNA can be readily determined using methods known to those of skill in the art.

Preferably, the modified siRNA is at least about 80% (e.g., 80%, 85%, 90%, 91%, 92%, 93%, 94%, 95%, 96%, 97%, 98%, 99%, or 100%) less immunostimulatory than the corresponding unmodified siRNA sequence, and the modified siRNA has an $IC_{50}$ less than or equal to ten-fold (preferably three-fold and, more preferably, two-fold) that of the corresponding unmodified siRNA.

In yet another embodiments, the modified siRNA is capable of silencing at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, or more of the expression of the target sequence relative to the corresponding unmodified siRNA sequence.

In some embodiments, the modified siRNA does not comprise phosphate backbone modifications, e.g., in the sense and/or antisense strand of the double-stranded region. In other embodiments, the modified siRNA does not comprise 2'-deoxy nucleotides, e.g., in the sense and/or antisense strand of the double-stranded region. In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The modified siRNA of the present invention may have 3' overhangs of one, two, three, four, or more nucleotides on one or both sides of the double-stranded region, or may lack overhangs (i.e., have blunt ends). Preferably, the modified siRNA has 3' overhangs of two nucleotides on each side of the double-stranded region. In certain instances, the 3' overhang on the antisense strand has complementarity to the target sequence and the 3' overhang on the sense strand has complementarity to the complementary strand of the target sequence (see, e.g., the ApoB siRNA duplexes in Table 3). Alternatively, the 3' overhangs do not have complementarity to the target sequence or the complementary strand thereof. In some embodiments, the 3' overhangs comprise one, two, three, four, or more nucleotides such as 2'-deoxy (2'H) nucleotides. Preferably, the 3' overhangs comprise deoxythymidine (dT) nucleotides.

In some embodiments, the corresponding unmodified siRNA sequence comprises at least one, two, three, four, five, six, seven, or more 5'-GU-3' motifs (SEQ ID NO:1). The 5'-GU-3' motif can be in the sense strand, the antisense strand, or both strands of the unmodified siRNA sequence.

In certain embodiments, the modified siRNA further comprises a carrier system, e.g., to deliver the modified siRNA into a cell of a mammal. Non-limiting examples of carrier systems suitable for use in the present invention include nucleic acid-lipid particles, liposomes, micelles, virosomes, nucleic acid complexes, and mixtures thereof. In certain instances, the modified siRNA molecule is complexed with a lipid such as a cationic lipid to form a lipoplex. In certain other instances, the modified siRNA molecule is complexed with a polymer such as a cationic polymer (e.g., polyethylenimine (PEI)) to form a polyplex. The modified siRNA molecule may also be complexed with cyclodextrin or a polymer thereof. Preferably, the modified siRNA molecule is encapsulated in a nucleic acid-lipid particle.

The present invention also provides a pharmaceutical composition comprising a modified siRNA described herein and a pharmaceutically acceptable carrier.

In a related aspect, the present invention provides a modified siRNA comprising a double-stranded region of about 15 to about 60 nucleotides in length (e.g., about 15-60, 15-50, 15-40, 15-30, 15-25, or 19-25 nucleotides in length), wherein at least one, two, three, four, five, six, seven, eight, nine, ten, or more of the nucleotides in the sense strand of the siRNA comprise modified nucleotides and no nucleotides in the antisense strand of the siRNA are modified nucleotides.

In another aspect, the present invention provides a modified siRNA comprising a double-stranded region of about 15 to about 60 nucleotides in length (e.g., about 15-60, 15-50, 15-40, 15-30, 15-25, or 19-25 nucleotides in length), wherein at least two of the nucleotides in the double-stranded region comprise modified nucleotides selected from the group consisting of modified guanosine nucleotides, modified uridine nucleotides, and mixtures thereof. The modified siRNA is notably less immunostimulatory than a corresponding unmodified siRNA sequence and is capable of silencing expression of a target sequence.

Typically, the modified siRNA comprises from about 1% to about 100% (e.g., about 1%, 5%, 10%, 15%, 20%, 25%, 30%, 35%, 40%, 45%, 50%, 55%, 60%, 65%, 70%, 75%, 80%, 85%, 90%, 95%, or 100%) modified nucleotides in the double-stranded region of the siRNA duplex. In preferred embodiments, less than about 30% (e.g., less than about 30%, 25%, 20%, 15%, 10%, or 5%) or from about 1% to about 30% (e.g., from about 1%-30%, 5%-30%, 10%-30%, 15%-30%, 20%-30%, or 25%-30%) of the nucleotides in the double-stranded region comprise modified nucleotides. As a non-limiting example, the modified siRNA can contain ten 2'OMe-guanosine and/or 2'OMe-uridine nucleotides, representing less than about 30% of the native 2'-OH positions in the double-stranded region of the siRNA duplex. This minimal degree of chemical modification, when incorporated into highly immunostimulatory siRNA sequences, can reduce or completely abrogate siRNA-mediated interferon and inflammatory cytokine induction in vitro and in vivo (see, Examples 2-4).

In some embodiments, the modified siRNA comprises modified guanosine and/or uridine nucleotides including, but not limited to, 2'OMe-guanosine nucleotides, 2'OMe-uridine nucleotides, 2'F-guanosine nucleotides, 2'F-uridine nucleotides, 2'-deoxy guanosine nucleotides, 2'-deoxy uridine nucleotides, 2'OMOE-guanosine nucleotides, 2'OMOE-uridine nucleotides, LNA guanosine nucleotides, LNA uridine nucleotides, and mixtures thereof. In preferred embodiments, the modified siRNA comprises 2'OMe-guanosine nucleotides, 2'OMe-uridine nucleotides, and mixtures thereof. In other embodiments, the modified siRNA comprises a hairpin loop structure.

The modified siRNA can comprise modified nucleotides in one strand (i.e., sense or antisense) or both strands of the double-stranded region of the siRNA. Preferably, at least two, three, four, five, six, seven, eight, nine, ten, or more of the uridine and/or guanosine nucleotides are modified at selective positions in the double-stranded region of the siRNA duplex.

In certain embodiments, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% less immunostimulatory than the corresponding unmodified siRNA sequence. Preferably, the modified siRNA is at least about 80% (e.g., 80%, 85%, 90%, 91%, 92%, 93%, 94%, 95%, 96%, 97%, 98%, 99%, or 100%) less immunostimulatory than the corresponding unmodified siRNA sequence and has an $IC_{50}$ less than or equal to ten-fold that of the corresponding unmodified siRNA. In other embodiments, the modified siRNA has an $IC_{50}$ less than or equal to three-fold that of the corresponding unmodified siRNA. In yet other embodiments, the modified siRNA preferably has an $IC_{50}$ less than or equal to two-fold that of the corresponding unmodified siRNA.

In other embodiments, the modified siRNA is capable of silencing at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, or more of the expression of the target sequence relative to the corresponding unmodified siRNA sequence.

In some embodiments, the modified siRNA does not comprise phosphate backbone modifications, e.g., in the sense and/or antisense strand of the double-stranded region. In other embodiments, the modified siRNA does not comprise 2'-deoxy nucleotides, e.g., in the sense and/or antisense strand of the double-stranded region. In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The modified siRNA of the present invention may have 3' overhangs of one, two, three, four, or more nucleotides on one or both sides of the double-stranded region, or may lack overhangs (i.e., have blunt ends). Preferably, the modified siRNA has 3' overhangs of two nucleotides on each side of the double-stranded region. In some embodiments, the 3' overhangs comprise one, two, three, four, or more nucleotides such as 2'-deoxy (2'H) nucleotides. Preferably, the 3' overhangs comprise deoxythymidine (dT) nucleotides.

In some embodiments, the corresponding unmodified siRNA sequence comprises at least one, two, three, four, five, six, seven, or more 5'-GU-3' motifs (SEQ ID NO:1). The 5'-GU-3' motif can be in the sense strand, the antisense strand, or both strands of the unmodified siRNA sequence.

In certain embodiments, the modified siRNA further comprises a carrier system, e.g., to deliver the modified siRNA into a cell of a mammal. Non-limiting examples of carrier systems include nucleic acid-lipid particles, liposomes, micelles, virosomes, nucleic acid complexes, and mixtures thereof. In certain instances, the modified siRNA molecule is complexed with a lipid such as a cationic lipid to form a lipoplex. In certain other instances, the modified siRNA molecule is complexed with a polymer such as a cationic polymer (e.g., PEI) to form a polyplex. The modified siRNA molecule may also be complexed with cyclodextrin or a polymer thereof. Preferably, the modified siRNA molecule is encapsulated in a nucleic acid-lipid particle.

The present invention also provides a pharmaceutical composition comprising a modified siRNA described herein and a pharmaceutically acceptable carrier.

In yet another aspect, the present invention provides a nucleic acid-lipid particle comprising a modified siRNA described herein, a cationic lipid, and a non-cationic lipid. In certain instances, the nucleic acid-lipid particle further comprises a conjugated lipid that inhibits aggregation of particles. Preferably, the nucleic acid-lipid particle comprises a modified siRNA described herein, a cationic lipid, a non-cationic lipid, and a conjugated lipid that inhibits aggregation of particles.

The cationic lipid may be, e.g., N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxypropylamine (DODMA), 1,2-DiLinoleyloxy-N,N-dimethylaminopropane (DLinDMA), 1,2-Dilinolenyloxy-N,N-dimethylaminopropane (DLendMA), or mixtures thereof. The cationic lipid may comprise from about 20 mol % to about 50 mol % or about 40 mol % of the total lipid present in the particle.

The non-cationic lipid may be an anionic lipid or a neutral lipid including, but not limited to, distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dipalmitoyl-phosphatidylcholine (DPPC), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), cholesterol, or mixtures thereof. The non-cationic lipid may comprise from about 5 mol % to about 90 mol % or about 20 mol % of the total lipid present in the particle.

The conjugated lipid that inhibits aggregation of particles may be a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be a PEG-dilauryloxypropyl (C12), a PEG-dimyristyloxypropyl (C14), a PEG-dipalmityloxypropyl (C16), or a PEG-distearyloxypropyl (C18). In some embodiments, the conjugated lipid that inhibits aggregation of particles is a CPL that has the formula: A-W-Y, wherein A is a lipid moiety, W is a hydrophilic polymer, and Y is a polycationic moiety. W may be a polymer selected from the group consisting of PEG, polyamide, polylactic acid, polyglycolic acid, polylactic acid/polyglycolic acid copolymers, or combinations thereof, the polymer having a molecular weight of from about 250 to about 7000 daltons. In some embodiments, Y has at least 4 positive charges at a selected pH. In some embodiments, Y may be lysine, arginine, asparagine, glutamine, derivatives thereof, or combinations thereof. The conjugated lipid that prevents aggregation of particles may be from 0 mol % to about 20 mol % or about 2 mol % of the total lipid present in the particle.

In some embodiments, the nucleic acid-lipid particle further comprises cholesterol at, e.g., about 10 mol % to about 60 mol %, about 30 mol % to about 50 mol %, or about 48 mol % of the total lipid present in the particle.

In certain embodiments, the modified siRNA in the nucleic acid-lipid particle is not substantially degraded after exposure of the particle to a nuclease at 37° C. for at least 20, 30, 45, or 60 minutes; or after incubation of the particle in serum at 37° C. for at least 30, 45, or 60 minutes.

In some embodiments, the modified siRNA is fully encapsulated in the nucleic acid-lipid particle. In other embodiments, the modified siRNA is complexed with the lipid portion of the particle.

The present invention further provides pharmaceutical compositions comprising the nucleic acid-lipid particles described herein and a pharmaceutically acceptable carrier.

In still yet another aspect, the modified siRNA described herein is used in methods for silencing expression of a target sequence. In particular, it is an object of the present invention to provide in vitro and in vivo methods for treatment of a disease or disorder in a mammal by downregulating or silencing the transcription and/or translation of a target gene of interest. In one embodiment, the present invention provides a method for introducing an siRNA that silences expression (e.g., mRNA and/or protein levels) of a target sequence into a cell by contacting the cell with a modified siRNA described herein. In another embodiment, the present invention provides a method for in vivo delivery of an siRNA that silences expression of a target sequence by administering to a mammal a modified siRNA described herein. Administration of the modified siRNA can be by any route known in the art, such as, e.g., oral, intranasal, intravenous, intraperitoneal, intramuscular, intra-articular, intralesional, intratracheal, subcutaneous, or intradermal.

In these methods, the modified siRNA is typically formulated with a carrier system, and the carrier system comprising the modified siRNA is administered to a mammal requiring such treatment. Examples of carrier systems suitable for use in the present invention include, but are not limited to, nucleic acid-lipid particles, liposomes, micelles, virosomes, nucleic acid complexes (e.g., lipoplexes, polyplexes, etc.), and mixtures thereof. The carrier system may comprise at least one, two, three, four, five, six, seven, eight, nine, ten, or more of the modified siRNA molecules described herein. Alternatively, cells are removed from a mammal such as a human, the modified siRNA is delivered in vitro, and the cells are then administered to the mammal, such as by injection.

In some embodiments, the modified siRNA is in a nucleic acid-lipid particle comprising the modified siRNA, a cationic lipid, and a non-cationic lipid. Preferably, the modified siRNA is in a nucleic acid-lipid particle comprising the modified siRNA, a cationic lipid, a non-cationic lipid, and a conjugated lipid that inhibits aggregation of particles. A therapeutically effective amount of the nucleic acid-lipid particle can be administered to the mammalian subject (e.g., a rodent such as a mouse or a primate such as a human, chimpanzee, or monkey).

In another embodiment, at least about 1%, 2%, 4%, 6%, 8%, or 10% of the total administered dose of the nucleic acid-lipid particles is present in plasma at about 1, 2, 4, 6, 8, 12, 16, 18, or 24 hours after administration. In a further embodiment, more than about 20%, 30%, or 40% or as much as about 60%, 70%, or 80% of the total administered dose of the nucleic acid-lipid particles is present in plasma at about 1, 4, 6, 8, 10, 12, 20, or 24 hours after administration. In one embodiment, the effect of a modified siRNA (e.g., downregulation of a target sequence) at a site proximal or distal to the site of administration is detectable at about 12, 24, 48, 72, or 96 hours, or at about 6, 8, 10, 12, 14, 16, 18, 19, 20, 22, 24, 26, or 28 days after administration of the nucleic acid-lipid particles. In another embodiment, downregulation of expression of the target sequence is detectable at about 12, 24, 48, 72, or 96 hours, or at about 6, 8, 10, 12, 14, 16, 18, 19, 20, 22, 24, 26, or 28 days after administration. In certain instances, downregulation of expression of a gene sequence is detected by measuring mRNA or protein levels in a biological sample from the mammal.

The nucleic acid-lipid particles are suitable for use in intravenous nucleic acid delivery as they are stable in circulation, of a size required for pharmacodynamic behavior resulting in access to extravascular sites, and target cell populations. The present invention also provides pharmaceutically acceptable compositions comprising nucleic acid-lipid particles.

In a further aspect, the present invention provides a method for modifying an siRNA having immunostimulatory properties comprising: (a) providing an unmodified siRNA sequence capable of silencing expression of a target sequence and comprising a double-stranded sequence of about 15 to about 60 nucleotides in length (e.g., about 15-60, 15-50, 15-40, 15-30, 15-25, or 19-25 nucleotides in length); and (b) modifying the siRNA by substituting at least one nucleotide in the sense or antisense strand with a modified nucleotide, thereby generating a modified siRNA that is less immunostimulatory than the unmodified siRNA sequence and is capable of silencing expression of the target sequence.

In some embodiments, the modified nucleotide includes, but is not limited to, 2'OMe nucleotides, 2° F. nucleotides, 2'-deoxy nucleotides, 2'OMOE nucleotides, LNA nucleotides, and mixtures thereof. In preferred embodiments, the modified nucleotide comprises a 2'OMe nucleotide (e.g., 2'OMe purine and/or pyrimidine nucleotide) such as, for example, a 2'OMe-guanosine nucleotide, 2'OMe-uridine nucleotide, 2'OMe-adenosine nucleotide, 2'OMe-cytosine nucleotide, and mixtures thereof. In certain instances, the modified nucleotide is not a 2'OMe-cytosine nucleotide.

In certain instances, the unmodified siRNA sequence comprises at least one, two, three, four, five, six, seven, or more 5'-GU-3' motifs (SEQ ID NO:1). The 5'-GU-3' motif can be in the sense strand, the antisense strand, or both strands of the unmodified siRNA sequence. Preferably, at least one nucleotide in the 5'-GU-3' motif is substituted with a modified nucleotide. As a non-limiting example, both nucleotides in the 5'-GU-3' motif can be substituted with modified nucleotides.

In some embodiments, the method further comprises: (c) confirming that the modified siRNA is less immunostimulatory by contacting the modified siRNA with a mammalian responder cell under conditions suitable for the responder cell to produce a detectable immune response. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-12, or a combination thereof.

In a related aspect, the present invention provides a method for identifying and modifying an siRNA having immunostimulatory properties. The method comprises: (a) contacting an unmodified siRNA sequence with a mammalian responder cell under conditions suitable for the responder cell to produce a detectable immune response; (b) identifying the unmodified siRNA sequence as an immunostimulatory siRNA by the presence of a detectable immune response in the responder cell; and (c) modifying the immunostimulatory siRNA by substituting at least one nucleotide with a modified nucleotide, thereby generating a modified siRNA sequence that is less immunostimulatory than the unmodified siRNA sequence.

In certain embodiments, the modified nucleotide includes, but is not limited to, 2'OMe nucleotides, 2° F. nucleotides, 2'-deoxy nucleotides, 2'OMOE nucleotides, LNA nucleotides, and mixtures thereof. In preferred embodiments, the modified nucleotide comprises a 2'OMe nucleotide (e.g., 2'OMe purine and/or pyrimidine nucleotide) such as, for example, a 2'OMe-guanosine nucleotide, 2'OMe-uridine nucleotide, 2'OMe-adenosine nucleotide, 2'OMe-cytosine nucleotide, and mixtures thereof. In certain instances, the modified nucleotide is not a 2'OMe-cytosine nucleotide.

In certain instances, the unmodified siRNA sequence comprises at least one, two, three, four, five, six, seven, or more 5'-GU-3' motifs. The 5'-GU-3' motif can be in the sense strand, the antisense strand, or both strands of the unmodified siRNA sequence. Preferably, at least one nucleotide in the 5'-GU-3' motif is substituted with a modified nucleotide. As a non-limiting example, both nucleotides in the 5'-GU-3' motif can be substituted with modified nucleotides.

In one embodiment, the mammalian responder cell is a peripheral blood mononuclear cell (PBMC), a macrophage, and the like. In another embodiment, the detectable immune response comprises production of a cytokine or growth factor such as, for example, TNF-α, IFN-α, IFN-β, IFN-γ, IL-6, IL-12, or a combination thereof.

In an additional aspect, the present invention provides isolated nucleic acid molecules comprising a modified sequence set forth in Tables 1 and 2. The modified sequence can further include its complementary strand, thereby generating a modified siRNA duplex. In a related aspect, the present invention provides isolated nucleic acid molecules comprising a modified siRNA duplex set forth in Tables 3, 5, and 6.

Other features, objects, and advantages of the invention and its preferred embodiments will become apparent from the detailed description, examples, and claims that follow.

BRIEF DESCRIPTION OF THE DRAWINGS

FIG. 6 illustrates data demonstrating the generation of non-inflammatory β-gal siRNAs that retain full RNAi activity. Immunostimulatory β-gal 728 siRNA was chemically modified by the incorporation of either 2'OMe-uridine (U), guanosine (G), cytidine (C), or adenosine (A) into the sense strand (S) of the siRNA duplex.

FIG. 7 illustrates data demonstrating the generation of non-inflammatory luciferase siRNA that retain full RNAi activity. Immunostimulatory luciferase (Luc) siRNA was chemically modified by the incorporation of 2'OMe-uridine (U) into the sense strand (S) of the siRNA duplex.

FIG. 10 illustrates data demonstrating silencing of ApoB expression in vivo without activation of the innate immune response. (Figs. A-E) In vivo effects following intravenous administration of encapsulated ApoB or mismatch siRNA in mice. Mice were treated on d 0, 1, and 2 with encapsulated unmodified, 2'OMe U(S), or GU(AS) modified ApoB, and unmodified or 2'OMe U(S) modified mismatch siRNA at 5 mg/kg per day.

Figure 1A:
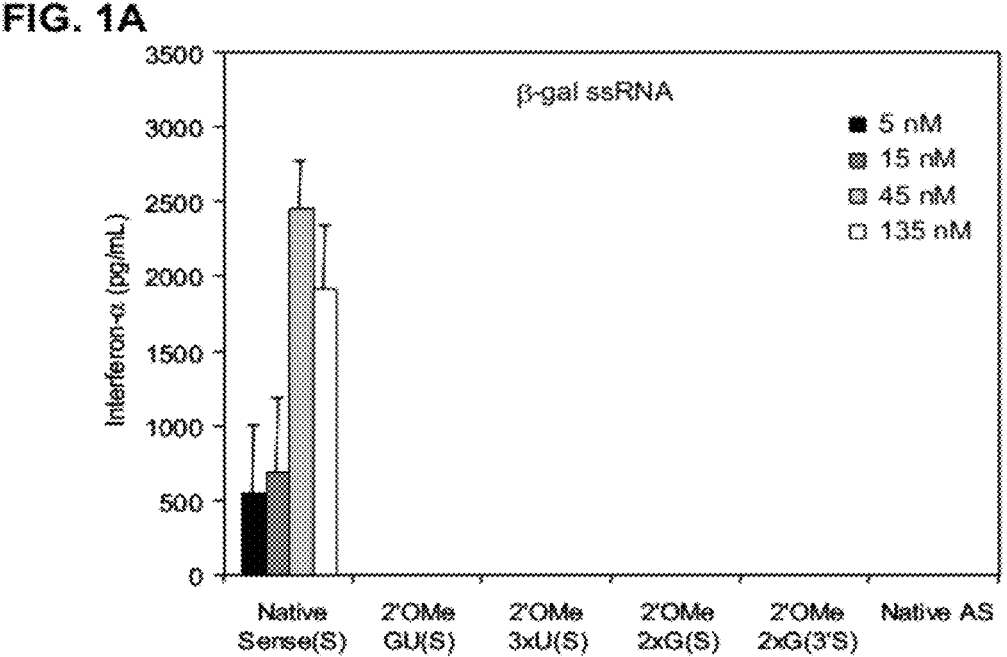
FIG. 1 illustrates data demonstrating that 2'OMe modification abrogates immunostimulatory ssRNA-mediated interferon induction in human PBMC. Liposome encapsulated, unmodified (native) and 2'OMe U-, G-, or GU-modified ssRNA representing the sense (S) or antisense (AS) strands of (FIG. 1A) β-gal and (FIG. 1B) ApoB siRNA were cultured with PBMC at increasing concentrations (5-135 nM). Sequences are shown in Table 1. IFN-α was assayed in culture supernatants at 24 hours. Values are mean+SD of triplicate cultures.

As used herein, the term "mismatch motif" or "mismatch region" refers to a portion of an siRNA sequence that does not have 100% complementarity to its target sequence. An siRNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

An "effective amount" or "therapeutically effective amount" of an siRNA is an amount sufficient to produce the desired effect, e.g., an inhibition of expression of a target sequence in comparison to the normal expression level detected in the absence of the siRNA. Inhibition of expression of a target gene or target sequence is achieved when the value obtained with the siRNA relative to the control is about 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or mRNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by an siRNA is intended to mean a detectable decrease of an immune response to siRNA (e.g., a modified siRNA). The amount of decrease of an immune response by a modified siRNA may be determined relative to the level of an immune response in the presence of an unmodified siRNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified siRNA. A decrease in the immune response to siRNA is typically measured by a decrease in cytokine production (e.g., IFNγ, IFNα, TNFα, IL-6, or IL-12) by a responder cell in vitro or a decrease in cytokine production in the sera of a mammalian subject after administration of the siRNA.

As used herein, the term "responder cell" refers to a cell, preferable a mammalian cell, that produces a detectable immune response when contacted with an immunostimulatory siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-10, IL-12, IL-13, TGF, and combinations thereof.

"Substantial identity" refers to a sequence that hybridizes to a reference sequence under stringent conditions, or to a sequence that has a specified percent identity over a specified region of a reference sequence.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

A preferred example of algorithms that are suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/).

The BLAST algorithm also performs a statistical analysis of the similarity between two sequences (see, e.g., Karlin and Altschul, *Proc. Natl. Acad. Sci. USA*, 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (PI, PAC, BAC, YAC, artificial chromosomes), expression cassettes, chimeric sequences, chromosomal DNA, or derivatives and combinations of these groups. RNA may be in the form of siRNA, mRNA, tRNA, rRNA, tRNA, vRNA, and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.,* 19:5081 (1991); Ohtsuka et al., *J. Biol. Chem.,* 260:2605-2608 (1985); Rossolini et al., *Mol. Cell. Probes,* 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

"Lipid vesicle" refers to any lipid composition that can be used to deliver a compound such as an siRNA including, but not limited to, liposomes, wherein an aqueous volume is encapsulated by an amphipathic lipid bilayer; or wherein the lipids coat an interior comprising a large molecular component, such as a plasmid comprising an interfering RNA sequence, with a reduced aqueous interior; or lipid aggregates or micelles, wherein the encapsulated component is contained within a relatively disordered lipid mixture. The term lipid vesicle encompasses any of a variety of lipid-based carrier systems including, without limitation, SPLPs, pSPLPs, SNALPs, liposomes, micelles, virosomes, lipid-nucleic acid complexes, and mixtures thereof.

As used herein, "lipid encapsulated" can refer to a lipid formulation that provides a compound such as an siRNA with full encapsulation, partial encapsulation, or both. In a preferred embodiment, the nucleic acid is fully encapsulated in the lipid formulation (e.g., to form an SPLP, pSPLP, SNALP, or other nucleic acid-lipid particle).

As used herein, the term "SNALP" refers to a stable nucleic acid-lipid particle, including SPLP. A SNALP represents a vesicle of lipids coating a reduced aqueous interior comprising a nucleic acid (e.g., siRNA, ssDNA, dsDNA, ssRNA, micro RNA (miRNA), short hairpin RNA (shRNA), dsRNA, or a plasmid, including plasmids from which an interfering RNA is transcribed). As used herein, the term "SPLP" refers to a nucleic acid-lipid particle comprising a nucleic acid (e.g., a plasmid) encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection, accumulate at distal sites (e.g., sites physically separated from the administration site) and can mediate expression of the transfected gene at these distal sites. SPLPs include "pSPLP," which comprise an encapsulated condensing agent-nucleic acid complex as set forth in PCT Publication No. WO 00/03683.

The nucleic acid-lipid particles of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids, when present in the nucleic acid-lipid particles of the present invention, are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; and 6,815,432; and PCT Publication No. WO 96/40964.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle-adopting lipid" is intended to include any amphipathic lipid that is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane. Vesicle-adopting lipids include lipids that on their own tend to adopt a nonlamellar phase, yet which are capable of assuming a bilayer structure in the presence of a bilayer-stabilizing component. A typical example is dioleoylphosphatidylethanolamine (DOPE). Bilayer stabilizing components include, but are not limited to, conjugated lipids that inhibit aggregation of nucleic acid-lipid particles, polyamide oligomers (e.g., ATTA-lipid derivatives), peptides, proteins, detergents, lipid-derivatives, PEG-lipid derivatives such as PEG coupled to dialkyloxypropyls, PEG coupled to diacylglycerols, PEG coupled to phosphatidyl-ethanolamines, PEG conjugated to ceramides (see, e.g., U.S. Pat. No. 5,885,613), cationic PEG lipids, and mixtures thereof. PEG can be conjugated directly to the lipid or may be linked to the lipid via a linker moiety. Any linker moiety suitable for coupling the PEG to a lipid can be used including, e.g., non-ester containing linker moieties and ester-containing linker moieties.

The term "amphipathic lipid" refers, in part, to any suitable material wherein the hydrophobic portion of the lipid material orients into a hydrophobic phase, while the hydrophilic portion orients toward the aqueous phase. Amphipathic lipids are usually the major component of a lipid vesicle. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any neutral lipid as described above as well as anionic lipids.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH (e.g., pH of about 7.0). It has been surprisingly found that cationic lipids comprising alkyl chains with multiple sites of unsaturation, e.g., at least two or three sites of unsaturation, are particularly useful for forming nucleic acid-lipid particles with increased membrane fluidity. A number of cationic lipids and related analogs, which are also useful in the present invention, have been described in U.S. Patent Publication No. 20060083780; U.S. Pat. Nos. 5,208,036; 5,264,618; 5,279,833; 5,283,185; 5,753,613; and 5,785,992; and PCT Publication No. WO 96/10390. Examples of cationic lipids include, but are not limited to, N,N-dioleyl-N,N-dimethylammonium chloride (DODAC), dioctadecyldimethylammonium (DODMA), distearyldimethylammonium (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N-(N',N'-dimethylaminoethane)-carbamoyl) cholesterol (DC-Chol), N-(1,2-dimyristyloxyprop-3-yl)-N, N-dimethyl-N-hydroxyethyl ammonium bromide (DMRIE), 1,2-dilinoleyloxy-N,N-dimethylaminopropane (DLinDMA), 1,2-dilinolenyloxy-N,N-dimethylaminopropane (DLenDMA), and mixtures thereof. As a non-limiting example, cationic lipids that have a positive charge below physiological pH include, but are not limited to, DODAP, DODMA, and DSDMA. In some cases, the cationic lipids comprise a protonatable tertiary amine head group, C18 alkyl chains, ether linkages between the head group and alkyl chains, and 0 to 3 double bonds. Such lipids include, e.g., DSDMA, DLinDMA, DLenDMA, and DODMA. The cationic lipids may also comprise ether linkages and pH titratable head groups. Such lipids include, e.g., DODMA.

The term "hydrophobic lipid" refers to compounds having apolar groups that include, but are not limited to, long chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N-N-dialkylamino, 1,2-diacyloxy-3-aminopropane, and 1,2-dialkyl-3-aminopropane.

The term "fusogenic" refers to the ability of a liposome, a SNALP, or other drug delivery system to fuse with membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery that leads to a broad biodistribution of a compound such as an siRNA within an organism. Some techniques of administration can lead to the systemic delivery of certain compounds, but not others. Systemic delivery means that a useful, preferably therapeutic, amount of a compound is exposed to most parts of the body. To obtain broad biodistribution generally requires a blood lifetime such that the compound is not rapidly degraded or cleared (such as by first pass organs (liver, lung, etc.) or by rapid, nonspecific cell binding) before reaching a disease site distal to the site of administration. Systemic delivery of nucleic acid-lipid particles can be by any means known in the art including, for example, intravenous, subcutaneous, and intraperitoneal. In a preferred embodiment, systemic delivery of nucleic acid-lipid particles is by intravenous delivery.

"Local delivery," as used herein, refers to delivery of a compound such as an siRNA directly to a target site within an organism. For example, a compound can be locally delivered by direct injection into a disease site such as a tumor or other target site such as a site of inflammation or a target organ such as the liver, heart, pancreas, kidney, and the like.

The term "mammal" refers to any mammalian species such as a human, mouse, rat, dog, cat, hamster, guinea pig, rabbit, livestock, and the like.

III. siRNAs

The modified siRNA molecules of the present invention are capable of silencing expression of a target sequence, are about 15 to 60 nucleotides in length, are less immunostimulatory than a corresponding unmodified siRNA sequence, and retain RNAi activity against the target sequence. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. In preferred embodiments, one or more of the uridine and/or guanosine nucleotides are modified. The modified nucleotides can be present in one strand (i.e., sense or antisense) or both strands of the siRNA. The siRNA sequences may have overhangs (e.g., 3' or 5' overhangs as described in Elbashir et al., *Genes Dev.*, 15:188 (2001) or Nykänen et al., *Cell*, 107:309 (2001)), or may lack overhangs (i.e., have blunt ends).

The modified siRNA generally comprises from about 1% to about 100% (e.g. about 1%, 5%, 10%, 15%, 20%, 25%, 30%, 35%, 40%, 45%, 50%, 55%, 60%, 65%, 70%, 75%, 80%, 85%, 90%, 95%, or 100%) modified nucleotides in the double-stranded region of the siRNA duplex. In one preferred embodiment, less than about 20% (e.g., less than about 20%, 19%, 18%, 17%, 16%, 15%, 14%, 13%, 12%, 11%, 10%, 9%, 8%, 7%, 6%, 5%, 4%, 3%, 2%, or 1%) or from about 1% to about 20% (e.g., from about 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, or 19%-20%) of the nucleotides in the double-stranded region comprise modified nucleotides. In another preferred embodiment, e.g., when one or both strands of the siRNA are selectively modified at uridine and/or guanosine nucleotides, the resulting modified siRNA can comprise less than about 30% modified nucleotides (e.g., less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% modified nucleotides) or from about 1% to about 30% modified nucleotides (e.g., from about 1%-30%, 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, or 29%-30% modified nucleotides).

A. Selection of siRNA Sequences

Suitable siRNA sequences can be identified using any means known in the art. Typically, the methods described in Elbashir et al., Nature, 411:494-498 (2001) and Elbashir et al., *EMBO J*, 20:6877-6888 (2001) are combined with rational design rules set forth in Reynolds et al., *Nature Biotech.*, 22(3):326-330 (2004).

Generally, the nucleotide sequence 3' of the AUG start codon of a transcript from the target gene of interest is scanned for dinucleotide sequences (e.g., AA, NA, CC, GG, or UU, wherein N=C, G, or U) (see, e.g., Elbashir et al., *EMBO J.*, 20:6877-6888 (2001)). The nucleotides immediately 3' to the dinucleotide sequences are identified as potential siRNA target sequences. Typically, the 19, 21, 23, 25, 27, 29, 31, 33, 35, or more nucleotides immediately 3' to the dinucleotide sequences are identified as potential siRNA target sites. In some embodiments, the dinucleotide sequence is an AA or NA sequence and the 19 nucleotides immediately 3' to the AA or NA dinucleotide are identified as a potential siRNA target site. siRNA target sites are usually spaced at different positions along the length of the target gene. To further enhance silencing efficiency of the siRNA sequences, potential siRNA target sites may be analyzed to identify sites that do not contain regions of homology to other coding sequences, e.g., in the target cell or organism. For example, a suitable siRNA target site of about 21 base pairs typically will not have more than 16-17 contiguous base pairs of homology to coding sequences in the target cell or organism. If the siRNA sequences are to be expressed from an RNA Pol III promoter, siRNA target sequences lacking more than 4 contiguous A's or T's are selected.

Once a potential siRNA sequence has been identified, the sequence can be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://boz094.ust.hk/RNAi/siRNA. One of skill in the art will appreciate that sequences with one or more of the foregoing characteristics may be selected for further analysis and testing as potential siRNA sequences.

Additionally, potential siRNA target sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal foldback structures. However, one of skill in the art will appreciate that sequences with one or more of the foregoing characteristics may still be selected for further analysis and testing as potential siRNA sequences.

In some embodiments, potential siRNA target sequences may be further analyzed based on siRNA duplex asymmetry as described in, e.g., Khvorova et al., *Cell*, 115:209-216 (2003); and Schwarz et al., *Cell*, 115:199-208 (2003). In other embodiments, potential siRNA target sequences may be further analyzed based on secondary structure at the mRNA target site as described in, e.g., Luo et al., *Biophys. Res. Commun.*, 318:303-310 (2004). For example, mRNA secondary structure can be modeled using the Mfold algorithm (available at http://www.bioinfo.rpi.edu/applications/mfold/rna/form1.cgi) to select siRNA sequences which favor accessibility at the mRNA target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3',5'-UGU-3',5'-GUGU-3',5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.*, 255:4980-4983 (1980)); enzyme-linked immunosorbent assays (ELISA) as described, for example, by Raines et al., *J. Biol. Chem.*, 257:5154-5160 (1982); immunocytochemical techniques, including the use of fluorochromes (Brooks et al., *Clin. Exp. Immunol.*, 39:477 (1980)); and neutralization of activity (Bowen-Pope et al., *Proc. Natl. Acad. Sci. USA*, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

A non-limiting example of an in vivo model for detecting an immune response includes an in vivo mouse cytokine induction assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler and Milstein, *Nature*, 256: 495-497 (1975); and Harlow and Lane, ANTIBODIES, A LABORATORY MANUAL, Cold Spring Harbor Publication, New York (1999)). Generation of monoclonal antibodies has been previously described and can be accomplished by any means known in the art (see, e.g., Buhring et al. in Hybridoma, Vol. 10, No. 1, pp. 77-78 (1991)). In some methods, the monoclonal antibody is labeled (e.g., with any composition detectable by spectroscopic, photochemical, biochemical, electrical, optical, chemical means, and the like) to facilitate detection.

B. Generating siRNA Molecules siRNA molecules can be provided in several forms including, e.g., as one or more isolated small-interfering RNA (siRNA) duplexes. The siRNA sequences may have overhangs (e.g., 3' or 5' overhangs as described in Elbashir et al., *Genes Dev.*, 15:188 (2001) or Nykänen et al., *Cell*, 107:309 (2001), or may lack overhangs (i.e., have blunt ends).

Preferably, siRNA molecules are chemically synthesized. The single stranded molecules that comprise the siRNA molecule can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The synthesis of the single stranded molecules makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 μmol scale protocol with a 2.5 min coupling step for 2'-O-methylated nucleotides. Alternatively, syntheses at the 0.2 μmol scale can be performed on a 96-well plate synthesizer from Protogene (Palo Alto, Calif.). However, a larger or smaller scale of synthesis is also within the scope of the present invention. Suitable reagents for synthesis of the siRNA single stranded molecules, methods for RNA deprotection, and methods for RNA purification are known to those of skill in the art.

The siRNA molecules can also be synthesized via a tandem synthesis technique, wherein both strands are synthesized as a single continuous fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, the siRNA molecules can be assembled from two distinct single stranded molecules, wherein one strand comprises the sense strand and the other comprises the antisense strand of the siRNA. For example, each strand can be synthesized separately and joined together by hybridization or ligation following synthesis and/or deprotection. In certain other instances, the siRNA molecules can be synthesized as a single continuous fragment, where the self-complementary sense and antisense regions hybridize to form an siRNA duplex having hairpin secondary structure.

C. Modifying siRNA Sequences

In certain aspects, the siRNA molecules of the present invention comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence.

Examples of modified nucleotides suitable for use in the present invention include, but are not limited to, ribonucleotides having a 2'-O-methyl (2'OMe), 2'-deoxy-2'-fluoro (2° F.), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in the siRNA molecules of the present invention. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2° F.) nucleotides, 2'-deoxy-2'-chloro (2'Cl) nucleotides, and 2'-azido nucleotides. In certain instances, the siRNA molecules of the present invention include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.*, 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.*, 29:2437-2447 (2001)) can be incorporated into the siRNA molecules of the present invention.

In certain embodiments, the siRNA molecules of the present invention further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-($\beta$-D-erythrofuranosyl) nucleotides, 4'-thio nucleotides, carbocyclic nucleotides, 1,5-anhydrohexitol nucleotides, L-nucleotides, $\alpha$-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties*, in *Modern Synthetic Methods*, VCH, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA.

In some embodiments, the sense and/or antisense strand can further comprise a 3'-terminal overhang having about 1 to about 4 (e.g., 1, 2, 3, or 4) 2'-deoxy ribonucleotides and/or any combination of modified and unmodified nucleotides. Additional examples of modified nucleotides and types of chemical modifications that can be introduced into the modified siRNA molecules of the present invention are described, e.g., in UK Patent No. GB 2,397,818 B and U.S. Patent Publication Nos. 20040192626 and 20050282188.

The modified siRNA molecules of the present invention can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the chemically-modified siRNA molecule. The conjugate can be attached at the 5' and/or 3'-end of the sense and/or antisense strand of the chemically-modified siRNA via a covalent attachment such as, e.g., a biodegradable linker. The conjugate can also be attached to the chemically-modified siRNA, e.g., through a carbamate group or other linking group (see, e.g., U.S. Patent Publication Nos. 20050074771, 20050043219, and 20050158727). In certain instances, the conjugate is a molecule that facilitates the delivery of the chemically-modified siRNA into a cell. Examples of conjugate molecules suitable for attachment to the chemically-modified siRNA of the present invention include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the chemically-modified siRNA molecule can be evaluated for improved pharmacokinetic profiles, bioavailability, and/or stability of the siRNA while retaining full RNAi activity. As such, one skilled in the art can screen chemically-modified siRNA molecules having various conjugates attached thereto to identify ones having improved properties and full RNAi activity using any of a variety of well-known in vitro cell culture or in vivo animal models.

D. Target Genes

The modified siRNA molecules described herein can be used to downregulate or silence the translation (i.e., expression) of a gene of interest. Genes of interest include, but are not limited to, genes associated with viral infection and survival, genes associated with metabolic diseases and disorders (e.g., liver diseases and disorders), genes associated with tumorigenesis and cell transformation, angiogenic genes, immunomodulator genes such as those associated with inflammatory and autoimmune responses, ligand receptor genes, and genes associated with neurodegenerative disorders.

Genes associated with viral infection and survival include those expressed by a virus in order to bind, enter, and replicate in a cell. Of particular interest are viral sequences associated with chronic viral diseases. Viral sequences of particular interest include sequences of Filoviruses such as Ebola virus and Marburg virus (see, e.g., U.S. patent application Ser. No. 11/584,341; and Geisbert et al., *J. Infect. Dis.*, 193:1650-1657 (2006)); Arenaviruses such as Lassa virus, Junin virus, Machupo virus, Guanarito virus, and Sabia virus (Buchmeier et al., Arenaviridae: the viruses and their replication, In: FIELDS VIROLOGY, Knipe et al. (eds.), 4th ed., Lippincott-Raven, Philadelphia, (2001)); Influenza viruses such as Influenza A, B, and C viruses, (see, e.g., U.S. Provisional Patent Application No. 60/737,945; Steinhauer et al., *Annu Rev Genet.*, 36:305-332 (2002); and Neumann et al., *J Gen Virol.*, 83:2635-2662 (2002)); Hepatitis viruses (Hamasaki et al., *FEBS Lett.*, 543:51 (2003); Yokota et al., *EMBO Rep.*, 4:602 (2003); Schlomai et al., *Hepatology*, 37:764 (2003); Wilson et al., *Proc. Natl. Acad. Sci. USA*, 100:2783 (2003); Kapadia et al., *Proc. Natl. Acad. Sci. USA*, 100:2014 (2003); and FIELDS VIROLOGY, Knipe et al. (eds.), 4th ed., Lippincott-Raven, Philadelphia (2001)); Human Immunodeficiency Virus (HIV) (Banerjea et al., *Mol. Ther.*, 8:62 (2003); Song et al., *J. Virol.*, 77:7174 (2003); Stephenson, *JAMA*, 289:1494 (2003); Qin et al., *Proc. Natl. Acad. Sci. USA*, 100:183 (2003)); Herpes viruses (Jia et al., *J. Virol.*, 77:3301 (2003)); and Human Papilloma Viruses (HPV) (Hall et al., *J. Virol.*, 77:6066 (2003); Jiang et al., *Oncogene*, 21:6041 (2002)).

Exemplary Filovirus nucleic acid sequences that can be silenced include, but are not limited to, nucleic acid sequences encoding structural proteins (e.g., VP30, VP35, nucleoprotein (NP), polymerase protein (L-pol)) and membrane-associated proteins (e.g., VP40, glycoprotein (GP), VP24). Complete genome sequences for Ebola virus are set forth in, e.g., Genbank Accession Nos. NC_002549; AY769362; NC_006432; NC_004161; AY729654; AY354458; AY142960; AB050936; AF522874; AF499101; AF272001; and AF086833. Ebola virus VP24 sequences are set forth in, e.g., Genbank Accession Nos. U77385 and AY058897. Ebola virus L-pol sequences are set forth in, e.g., Genbank Accession No. X67110. Ebola virus VP40 sequences are set forth in, e.g., Genbank Accession No. AY058896. Ebola virus NP sequences are set forth in, e.g., Genbank Accession No. AY058895. Ebola virus GP sequences are set forth in, e.g., Genbank Accession No. AY058898; Sanchez et al., *Virus Res.*, 29:215-240 (1993); Will et al., *J. Virol.*, 67:1203-1210 (1993); Volchkov et al., *FEBS Lett.*, 305:181-184 (1992); and U.S. Pat. No. 6,713,069. Additional Ebola virus sequences are set forth in, e.g., Genbank Accession Nos. L11365 and X61274. Complete genome sequences for Marburg virus are set forth in, e.g., Genbank Accession Nos. NC_001608; AY430365; AY430366; and AY358025. Marburg virus GP sequences are set forth in, e.g., Genbank Accession Nos. AF005734; AF005733; and AF005732. Marburg virus VP35 sequences are set forth in, e.g., Genbank Accession Nos. AF005731 and AF005730. Additional Marburg virus sequences are set forth in, e.g., Genbank Accession Nos. X64406; Z29337; AF005735; and Z12132.

Exemplary Influenza virus nucleic acid sequences that can be silenced include, but are not limited to, nucleic acid sequences encoding nucleoprotein (NP), matrix proteins (M1 and M2), nonstructural proteins (NS1 and NS2), RNA polymerase (PA, PB1, PB2), neuraminidase (NA), and haemagglutinin (HA). Influenza A NP sequences are set forth in, e.g., Genbank Accession Nos. NC_004522; AY818138; AB166863; AB188817; AB189046; AB189054; AB189062; AY646169; AY646177; AY651486; AY651493; AY651494; AY651495; AY651496; AY651497; AY651498; AY651499; AY651500; AY651501; AY651502; AY651503; AY651504; AY651505; AY651506; AY651507; AY651509; AY651528; AY770996; AY790308; AY818138; and AY818140. Influenza A PA sequences are set forth in, e.g., Genbank Accession Nos. AY818132; AY790280; AY646171; AY818132; AY818133; AY646179; AY818134; AY551934; AY651613; AY651610; AY651620; AY651617; AY651600; AY651611; AY651606; AY651618; AY651608; AY651607; AY651605; AY651609; AY651615; AY651616; AY651640; AY651614; AY651612; AY651621; AY651619; AY770995; and AY724786.

Exemplary hepatitis virus nucleic acid sequences that can be silenced include, but are not limited to, nucleic acid sequences involved in transcription and translation (e.g., En1, En2, X, P) and nucleic acid sequences encoding structural proteins (e.g., core proteins including C and C-related proteins, capsid and envelope proteins including S, M, and/or L proteins, or fragments thereof) (see, e.g., FIELDS VIROLOGY, supra). Exemplary Hepatitis C nucleic acid sequences that can be silenced include, but are not limited to, serine proteases (e.g., NS3/NS4), helicases (e.g. NS3), polymerases (e.g., NS5B), and envelope proteins (e.g., E1, E2, and p7). Hepatitis A nucleic acid sequences are set forth in, e.g., Genbank Accession No. NC_001489; Hepatitis B nucleic acid sequences are set forth in, e.g., Genbank Accession No. NC_003977; Hepatitis C nucleic acid sequences are set forth in, e.g., Genbank Accession No. NC_004102; Hepatitis D nucleic acid sequence are set forth in, e.g., Genbank Accession No. NC_001653; Hepatitis E nucleic acid sequences are set forth in, e.g., Genbank Accession No. NC_001434; and Hepatitis G nucleic acid sequences are set forth in, e.g., Genbank Accession No. NC_001710. Silencing of sequences that encode genes associated with viral infection and survival can conveniently be used in combination with the administration of conventional agents used to treat the viral condition.

Genes associated with metabolic diseases and disorders (e.g., disorders in which the liver is the target and liver diseases and disorders) include, for example, genes expressed in dyslipidemia (e.g., liver X receptors such as LXRα and LXRβ (Genback Accession No. NM_007121), farnesoid X receptors (FXR) (Genbank Accession No. NM_005123), sterol-regulatory element binding protein (SREBP), Site-1 protease (S1P), 3-hydroxy-3-methylglutaryl coenzyme-A reductase (HMG coenzyme-A reductase), Apolipoprotein (ApoB), and Apolipoprotein (ApoE)); and diabetes (e.g., Glucose 6-phosphatase) (see, e.g., Forman et al., *Cell*, 81:687 (1995); Seol et al., *Mol. Endocrinol.*, 9:72 (1995), Zavacki et al., *Proc. Natl. Acad. Sci. USA*, 94:7909 (1997); Sakai et al., *Cell*, 85:1037-1046 (1996); Duncan et al., *J. Biol. Chem.*, 272:12778-12785 (1997); Willy et al., *Genes Dev.*, 9:1033-1045 (1995); Lehmann et al., *J. Biol. Chem.*, 272:3137-3140 (1997); Janowski et al., *Nature*, 383:728-731 (1996); and Peet et al., *Cell*, 93:693-704 (1998)). One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder.

Examples of gene sequences associated with tumorigenesis and cell transformation include mitotic kinesins such as Eg5; translocation sequences such as MLL fusion genes, BCR-ABL (Wilda et al., *Oncogene*, 21:5716 (2002); Scherr et al., *Blood*, 101:1566 (2003)), TEL-AML1, EWS-FLI1, TLS-FUS, PAX3-FKHR, BCL-2, AML1-ETO, and AML1-MTG8 (Heidenreich et al., *Blood*, 101:3157 (2003)); overexpressed sequences such as multidrug resistance genes (Nieth et al., *FEBS Lett.*, 545:144 (2003); Wu et al, *Cancer Res.* 63:1515 (2003)), cyclins (Li et al., *Cancer Res.*, 63:3593 (2003); Zou et al., *Genes Dev.*, 16:2923 (2002)), beta-catenin (Verma et al., *Clin Cancer Res.*, 9:1291 (2003)), telomerase genes (Kosciolek et al., *Mol Cancer Ther.*, 2:209 (2003)), c-MYC, N-MYC, BCL-2, ERBB1, and ERBB2 (Nagy et al. *Exp. Cell Res.*, 285:39 (2003)); and mutated sequences such as RAS (reviewed in Tuschl and Borkhardt, *Mol. Interventions*, 2:158 (2002)). Silencing of sequences that encode DNA repair enzymes find use in combination with the administration of chemotherapeutic agents (Collis et al., *Cancer Res.*, 63:1550 (2003)). Genes encoding proteins associated with tumor migration are also target sequences of interest, for example, integrins, selectins, and metalloproteinases. The foregoing examples are not exclusive. Any whole or partial gene sequence that facilitates or promotes tumorigenesis or cell transformation, tumor growth, or tumor migration can be included as a template sequence.

Angiogenic genes are able to promote the formation of new vessels. Of particular interest is Vascular Endothelial Growth Factor (VEGF) (Reich et al., *Mol. Vis.*, 9:210 (2003)) or VEGFr. siRNA sequences that target VEGFr are set forth in, e.g., GB 2396864; U.S. Patent Publication No. 20040142895; and CA2456444.

Anti-angiogenic genes are able to inhibit neovascularization. These genes are particularly useful for treating those cancers in which angiogenesis plays a role in the pathological development of the disease. Examples of anti-angiogenic genes include, but are not limited to, endostatin (see, e.g., U.S. Pat. No. 6,174,861), angiostatin (see, e.g., U.S. Pat. No. 5,639,725), and VEGF-R2 (see, e.g., Decaussin et al., *J. Pathol.*, 188: 369-377 (1999)).

Immunomodulator genes are genes that modulate one or more immune responses. Examples of immunomodulator genes include, without limitation, cytokines such as growth factors (e.g., TGF-α, TGF-β, EGF, FGF, IGF, NGF, PDGF, CGF, GM-CSF, SCF, etc.), interleukins (e.g., IL-2, IL-4, IL-12 (Hill et al., *J. Immunol.*, 171:691 (2003)), IL-15, IL-18, IL-20, etc.), interferons (e.g., IFN-α, IFN-β, IFN-γ, etc.) and TNF. Fas and Fas Ligand genes are also immunomodulator target sequences of interest (Song et al., *Nat. Med.*, 9:347 (2003)). Genes encoding secondary signaling molecules in hematopoietic and lymphoid cells are also included in the present invention, for example, Tec family kinases such as Bruton's tyrosine kinase (Btk) (Heinonen et al., *FEBS Lett.*, 527:274 (2002)).

Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g., inhibit, activate, etc.) the physiological pathway that the receptor is involved in (e.g., glucose level modulation, blood cell development, mitogenesis, etc.). Examples of cell receptor ligands include, but are not limited to, cytokines, growth factors, interleukins, interferons, erythropoietin (EPO), insulin, glucagon, G-protein coupled receptor ligands, etc. Templates coding for an expansion of trinucleotide repeats (e.g., CAG repeats) find use in silencing pathogenic sequences in neurodegenerative disorders caused by the expansion of trinucleotide repeats, such as spinobulbular muscular atrophy and Huntington's Disease (Caplen et al., *Hum. Mol. Genet.*, 11:175 (2002)).

In addition to its utility in silencing the expression of any of the above-described genes for therapeutic purposes, the siRNA described herein are also useful in research and development applications as well as diagnostic, prophylactic, prognostic, clinical, and other healthcare applications. As a non-limiting example, the modified siRNA molecules of the present invention can be used in target validation studies directed at testing whether a gene of interest has the potential to be a therapeutic target. The modified siRNA molecules of the present invention can also be used in target identification studies aimed at discovering genes as potential therapeutic targets.

IV. Carrier Systems Containing siRNA

In one aspect, the present invention provides carrier systems containing the modified siRNA molecules described herein. In some embodiments, the carrier system is a lipid-based carrier system such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Preferably, the carrier system is a stabilized nucleic acid-lipid particle such as a SNALP or SPLP. One skilled in the art will appreciate that the modified siRNA molecule of the present invention can also be delivered as naked siRNA.

A. Stabilized Nucleic Acid-Lipid Particles

The stabilized nucleic acid-lipid particles (SNALPs) of the present invention typically comprise a modified siRNA molecule as described herein, a cationic lipid (e.g., a cationic lipid of Formula I or II), and a non-cationic lipid. The SNALPs can further comprise a bilayer stabilizing component (i.e., a conjugated lipid that inhibits aggregation of the particles). The SNALPs may comprise at least 1, 2, 3, 4, 5, 6, 7, 8, 9, 10, or more of the modified siRNA molecules described herein, alone or in combination with at least 1, 2, 3, 4, 5, 6, 7, 8, 9, 10, or more unmodified siRNA molecules.

The SNALPs of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids are resistant in aqueous solution to degradation with a nuclease when present in the nucleic acid-lipid particles. Nucleic acid-lipid particles and their method of preparation are disclosed in, e.g., U.S. Pat. Nos. 5,753,613; 5,785,992; 5,705,385; 5,976,567; 5,981,501; 6,110,745; and 6,320,017; and PCT Publication No. WO 96/40964.

1. Cationic Lipids

Any of a variety of cationic lipids may be used in the stabilized nucleic acid-lipid particles of the present invention, either alone or in combination with one or more other cationic lipid species or non-cationic lipid species.

Cationic lipids which are useful in the present invention can be any of a number of lipid species which carry a net positive charge at physiological pH. Such lipids include, but are not limited to, DODAC, DODMA, DSDMA, DOTMA, DDAB, DOTAP, DOSPA, DOGS, DC-Chol, DMRIE, and mixtures thereof. A number of these lipids and related analogs have been described in U.S. Patent Publication No. 20060083780; U.S. Pat. Nos. 5,208,036; 5,264,618; 5,279,833; 5,283,185; and 5,753,613; and 5,785,992; and PCT Publication No. WO 96/10390. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

Furthermore, cationic lipids of Formula I having the following structures are useful in the present invention.

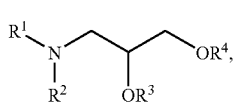
(I)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl (C18), etc. In certain other instances, $R^3$ and $R^4$ are different, i.e., $R^3$ is tetradectrienyl (C14) and $R^4$ is linoleyl (C18). In a preferred embodiment, the cationic lipid of Formula I is symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl. In a particularly preferred embodiments, the cationic lipid of Formula I is DLinDMA or DLenDMA.

Moreover, cationic lipids of Formula II having the following structures are useful in the present invention.

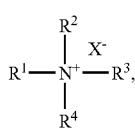
(II)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl (C18), etc. In certain other instances, $R^3$ and $R^4$ are different, i.e., $R^3$ is tetradectrienyl (C14) and $R^4$ is linoleyl (C18). In a preferred embodiment, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

The cationic lipid typically comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % of the total lipid present in the particle. It will be readily apparent to one of skill in the art that depending on the intended use of the particles, the proportions of the components can be varied and the delivery efficiency of a particular formulation can be measured using, e.g., an endosomal release parameter (ERP) assay. For example, for systemic delivery, the cationic lipid may comprise from about 5 mol % to about 15 mol % of the total lipid present in the particle, and for local or regional delivery, the cationic lipid may comprise from about 30 mol % to about 50 mol %, or about 40 mol % of the total lipid present in the particle.

2. Non-Cationic Lipids

The non-cationic lipids used in the stabilized nucleic acid-lipid particles of the present invention can be any of a variety of neutral uncharged, zwitterionic, or anionic lipids capable of producing a stable complex. They are preferably neutral, although they can alternatively be positively or negatively charged. Examples of non-cationic lipids include, without limitation, phospholipid-related materials such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), and stearoyloleoyl-phosphatidylethanolamine (SOPE). Non-cationic lipids or sterols such as cholesterol may also be present. Additional nonphosphorous containing lipids include, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, diacylphosphatidylcholine, diacylphosphatidylethanolamine, and the like. Other lipids such as lysophosphatidylcholine and lysophosphatidylethanolamine may be present. Non-cationic lipids also include polyethylene glycol-based polymers such as PEG 2000, PEG 5000, and polyethylene glycol conjugated to phospholipids or to ceramides (referred to as PEG-Cer), as described in U.S. patent application Ser. No. 08/316,429.

In preferred embodiments, the non-cationic lipids are diacylphosphatidylcholine (e.g., distearoylphosphatidylcholine, dioleoylphosphatidylcholine, dipalmitoylphosphatidylcholine, and dilinoleoylphosphatidylcholine), diacylphosphatidylethanolamine (e.g., dioleoylphosphatidylethanolamine and palmitoyloleoyl-phosphatidylethanolamine), ceramide, or sphingomyelin. The acyl groups in these lipids are preferably acyl groups derived from fatty acids having $C_{10}$-$C_{24}$ carbon chains. More preferably, the acyl groups are lauroyl, myristoyl, palmitoyl, stearoyl, or oleoyl. In particularly preferred embodiments, the non-cationic lipid includes one or more of cholesterol, DOPE, or ESM.

The non-cationic lipid typically comprises from about 5 mol % to about 90 mol %, from about 10 mol % to about 85 mol %, from about 20 mol % to about 80 mol %, or about 20 mol % of the total lipid present in the particle. The particles may further comprise cholesterol. If present, the cholesterol typically comprises from about 0 mol % to about 10 mol %, from about 2 mol % to about 10 mol %, from about 10 mol % to about 60 mol %, from about 12 mol % to about 58 mol %, from about 20 mol % to about 55 mol %, from about 30 mol % to about 50 mol %, or about 48 mol % of the total lipid present in the particle.

3. Bilayer Stabilizing Component

In addition to cationic and non-cationic lipids, the stabilized nucleic acid-lipid particles of the present invention can comprise a bilayer stabilizing component (BSC) such as an ATTA-lipid or a PEG-lipid such as PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides, or a mixture thereof (see, e.g., U.S. Pat. No. 5,885,613). In a preferred embodiment, the BSC is a conjugated lipid that prevents the aggregation of particles. Suitable conjugated lipids include, but are not limited to, PEG-lipid conjugates, ATTA-lipid conjugates, cationic-polymer-lipid conjugates (CPLs), and mixtures thereof. In another preferred embodiment, the particles comprise either a PEG-lipid conjugate or an ATTA-lipid conjugate together with a CPL.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH) is particularly useful for preparing the PEG-lipid conjugates including, e.g., PEG-DAA conjugates.

In a preferred embodiment, the PEG has an average molecular weight of from about 550 daltons to about 10,000 daltons, more preferably from about 750 daltons to about 5,000 daltons, more preferably from about 1,000 daltons to about 5,000 daltons, more preferably from about 1,500 daltons to about 3,000 daltons, and even more preferably about 2,000 daltons or about 750 daltons. The PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the bilayer stabilizing component. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" refers to, without limitation, compounds disclosed in U.S. Pat. Nos. 6,320,017 and 6,586,559. These compounds include a compound having the formula:

(III)

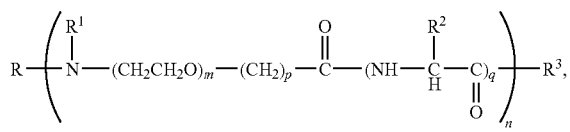

wherein R is a member selected from the group consisting of hydrogen, alkyl and acyl; $R^1$ is a member selected from the group consisting of hydrogen, and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" refers to a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauryl (C12), myristyl (C14), palmityl (C16), stearyl (C18), and icosyl (C20). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc. Diacylglycerols have the following general formula:

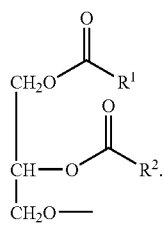

(IV)

The term "dialkyloxypropyl" refers to a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

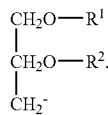

(V)

In a preferred embodiment, the PEG-lipid is a PEG-DAA conjugate having the following formula:

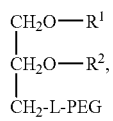

(VI)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, lauryl (C12), myristyl (C14), palmityl (C16), stearyl (C18), and icosyl (C20). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VI above, the PEG has an average molecular weight ranging from about 550 daltons to about 10,000 daltons, more preferably from about 750 daltons to about 5,000 daltons, more preferably from about 1,000 daltons to about 5,000 daltons, more preferably from about 1,500 daltons to about 3,000 daltons, and even more preferably about 2,000 daltons or about 750 daltons. The PEG can be optionally substituted with alkyl, alkoxy, acyl, or aryl. In a preferred embodiment, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992), Larock, COMPREHENSIVE ORGANIC TRANSFORMATIONS (VCH 1989); and Furniss, VOGEL'S TEXTBOOK OF PRACTICAL ORGANIC CHEMISTRY 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a dilauryloxypropyl (C12)-PEG conjugate, dimyristyloxypropyl (C14)-PEG conjugate, a dipalmityloxypropyl (C16)-PEG conjugate, or a distearyloxypropyl (C18)-PEG conjugate. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the particles (e.g., SNALPs or SPLPs) of the present invention can further comprise cationic poly(ethylene glycol) (PEG) lipids or CPLs that have been designed for insertion into lipid bilayers to impart a positive charge (see, e.g., Chen et al., *Bioconj. Chem.*, 11:433-437 (2000)). Suitable SPLPs and SPLP-CPLs for use in the present invention, and methods of making and using SPLPs and SPLP-CPLs, are disclosed, e.g., in U.S. Pat. No. 6,852,334 and PCT Publication No. WO 00/62813. Cationic polymer lipids (CPLs) useful in the present invention have the following architectural features: (1) a lipid anchor, such as a hydrophobic lipid, for incorporating the CPLs into the lipid bilayer; (2) a hydrophilic spacer, such as a polyethylene glycol, for linking the lipid anchor to a cationic head group; and (3) a polycationic moiety, such as a naturally occurring amino acid, to produce a protonizable cationic head group.

Suitable CPLs include compounds of Formula VII:

A-W-Y (VII), wherein A, W, and Y are as described below.

With reference to Formula VII, "A" is a lipid moiety such as an amphipathic lipid, a neutral lipid, or a hydrophobic lipid that acts as a lipid anchor. Suitable lipid examples include vesicle-forming lipids or vesicle adopting lipids and include, but are not limited to, diacylglycerolyls, dialkylglycerolyls, N-N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

The bilayer stabilizing component (e.g., PEG-lipid) typically comprises from about 0 mol % to about 20 mol %, from about 0.5 mol % to about 20 mol %, from about 1.5 mol % to about 18 mol %, from about 4 mol % to about 15 mol %, from about 5 mol % to about 12 mol %, or about 2 mol % of the total lipid present in the particle. One of ordinary skill in the art will appreciate that the concentration of the bilayer stabilizing component can be varied depending on the bilayer stabilizing component employed and the rate at which the nucleic acid-lipid particle is to become fusogenic.

By controlling the composition and concentration of the bilayer stabilizing component, one can control the rate at which the bilayer stabilizing component exchanges out of the nucleic acid-lipid particle and, in turn, the rate at which the nucleic acid-lipid particle becomes fusogenic. For instance, when a polyethyleneglycol-phosphatidylethanolamine conjugate or a polyethyleneglycol-ceramide conjugate is used as the bilayer stabilizing component, the rate at which the nucleic acid-lipid particle becomes fusogenic can be varied, for example, by varying the concentration of the bilayer stabilizing component, by varying the molecular weight of the polyethyleneglycol, or by varying the chain length and degree of saturation of the acyl chain groups on the phosphatidylethanolamine or the ceramide. In addition, other variables including, for example, pH, temperature, ionic strength, etc. can be used to vary and/or control the rate at which the nucleic acid-lipid particle becomes fusogenic. Other methods which can be used to control the rate at which the nucleic acid-lipid particle becomes fusogenic will become apparent to those of skill in the art upon reading this disclosure.

B. Additional Carrier Systems

Non-limiting examples of additional lipid-based carrier systems suitable for use in the present invention include lipoplexes (see, e.g., U.S. Patent Publication No. 20030203865; and Zhang et al., *J. Control Release*, 100:165-180 (2004)), pH-sensitive lipoplexes (see, e.g., U.S. Patent Publication No. 20020192275), reversibly masked lipoplexes (see, e.g., U.S. Patent Publication Nos. 20030180950), cationic lipid-based compositions (see, e.g., U.S. Pat. No. 6,756,054; and U.S. Patent Publication No. 20050234232), cationic liposomes (see, e.g., U.S. Patent Publication Nos. 20030229040, 20020160038, and 20020012998; U.S. Pat. No. 5,908,635; and PCT Publication No. WO 01/72283), anionic liposomes (see, e.g., U.S. Patent Publication No. 20030026831), pH-sensitive liposomes (see, e.g., U.S. Patent Publication No. 20020192274; and AU 2003210303), antibody-coated liposomes (see, e.g., U.S. Patent Publication No. 20030108597; and PCT Publication No. WO 00/50008), cell-type specific liposomes (see, e.g., U.S. Patent Publication No. 20030198664), liposomes containing nucleic acid and peptides (see, e.g., U.S. Pat. No. 6,207,456), liposomes containing lipids derivatized with releasable hydrophilic polymers (see, e.g., U.S. Patent Publication No. 20030031704), lipid-entrapped nucleic acid (see, e.g., PCT Publication Nos. WO 03/057190 and WO 03/059322), lipid-encapsulated nucleic acid (see, e.g., U.S. Patent Publication No. 20030129221; and U.S. Pat. No. 5,756,122), other liposomal compositions (see, e.g., U.S. Patent Publication Nos. 20030035829 and 20030072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 20050037086).

Examples of polymer-based carrier systems suitable for use in the present invention include, but are not limited to, cationic polymer-nucleic acid complexes (i.e., polyplexes). To form a polyplex, a nucleic acid (e.g., siRNA) is typically complexed with a cationic polymer having a linear, branched, star, or dendritic polymeric structure that condenses the nucleic acid into positively charged particles capable of interacting with anionic proteoglycans at the cell surface and entering cells by endocytosis. In some embodiments, the polyplex comprises nucleic acid (e.g. siRNA) complexed with a cationic polymer such as polyethylenimine (PEI) (see, e.g., U.S. Pat. No. 6,013,240; commercially available from Qbiogene, Inc. (Carlsbad, Calif.) as In vivo jetPEI™, a linear form of PEI), polypropylenimine (PPI), polyvinylpyrrolidone (PVP), poly-L-lysine (PLL), diethylaminoethyl (DEAE)-dextran, poly(β-amino ester) (PAE) polymers (see, e.g., Lynn et al., *J. Am. Chem. Soc.*, 123:8155-8156 (2001)), chitosan, polyamidoamine (PAMAM) dendrimers (see, e.g., Kukowska-Latallo et al., *Proc. Natl. Acad. Sci. USA*, 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No. WO/9602655; PCT Publication No. WO95/21931; Zhang et al., *J. Control Release*, 100:165-180 (2004); and Tiera et al., *Curr. Gene Ther.*, 6:59-71 (2006)), and a mixture thereof. In other embodiments, the polyplex comprises cationic polymer-nucleic acid complexes as described in U.S. Patent Publication Nos. 20060211643, 20050222064, 20030125281, and 20030185890, and PCT Publication No. WO 03/066069; biodegradable poly(β-amino ester) polymer-nucleic acid complexes as described in U.S. Patent Publication No. 20040071654; microparticles containing polymeric matrices as described in U.S. Patent Publication No. 20040142475; other microparticle compositions as described in U.S. Patent Publication No. 20030157030; condensed nucleic acid complexes as described in U.S. Patent Publication No. 20050123600; and nanocapsule and microcapsule compositions as described in AU 2002358514 and PCT Publication No. WO 02/096551.

In certain instances, the modified siRNA molecule may be complexed with cyclodextrin or a polymer thereof. Non-limiting examples of cyclodextrin-based carrier systems include the cyclodextrin-modified polymer-nucleic acid complexes described in U.S. Patent Publication No. 20040087024; the linear cyclodextrin copolymer-nucleic acid complexes described in U.S. Pat. Nos. 6,509,323, 6,884,789, and 7,091,192; and the cyclodextrin polymer-complexing agent-nucleic acid complexes described in U.S. Pat. No. 7,018,609. In certain other instances, the modified siRNA molecule may be complexed with a peptide or polypeptide. An example of a protein-based carrier system includes, but is not limited to, the cationic oligopeptide-nucleic acid complex described in PCT Publication No. WO95/21931.

V. Preparation of Nucleic Acid-Lipid Particles

The serum-stable nucleic acid-lipid particles of the present invention, in which the modified siRNA described herein is encapsulated in a lipid bilayer and is protected from degradation, can be formed by any method known in the art including, but not limited to, a continuous mixing method, a direct dilution process, a detergent dialysis method, or a modification of a reverse-phase method which utilizes organic solvents to provide a single phase during mixing of the components.

In preferred embodiments, the cationic lipids are lipids of Formula I and II or combinations thereof. In other preferred embodiments, the non-cationic lipids are egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, or combinations thereof. In still other preferred embodiments, the organic solvents are methanol, chloroform, methylene chloride, ethanol, diethyl ether, or combinations thereof.

In a preferred embodiment, the present invention provides for nucleic acid-lipid particles produced via a continuous mixing method, e.g., process that includes providing an aqueous solution comprising a nucleic acid such as an siRNA in a first reservoir, providing an organic lipid solution in a second reservoir, and mixing the aqueous solution with the organic lipid solution such that the organic lipid solution mixes with the aqueous solution so as to substantially instantaneously produce a liposome encapsulating the nucleic acid (e.g., siRNA). This process and the apparatus for carrying this process are described in detail in U.S. Patent Publication No. 20040142025.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The serum-stable nucleic acid-lipid particles formed using the continuous mixing method typically have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

In another embodiment, the present invention provides for nucleic acid-lipid particles produced via a direct dilution process that includes forming a liposome solution and immediately and directly introducing the liposome solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of liposome solution introduced thereto. As a non-limiting example, a liposome solution in 45% ethanol when introduced into the collection vessel containing an equal volume of ethanol will advantageously yield smaller particles in about 22.5%, about 20%, or about 15% ethanol.

In yet another embodiment, the present invention provides for nucleic acid-lipid particles produced via a direct dilution process in which a third reservoir containing dilution buffer is fluidly coupled to a second mixing region. In this embodiment, the liposome solution formed in a first mixing region is immediately and directly mixed with dilution buffer in the second mixing region. In preferred aspects, the second mixing region includes a T-connector arranged so that the liposome solution and the dilution buffer flows meet as opposing 180° flows; however, connectors providing shallower angles can be used, e.g., from about 27° to about 180°. A pump mechanism delivers a controllable flow of buffer to the second mixing region. In one aspect, the flow rate of dilution buffer provided to the second mixing region is controlled to be substantially equal to the flow rate of liposome solution introduced thereto from the first mixing region. This embodiment advantageously allows for more control of the flow of dilution buffer mixing with the liposome solution in the second mixing region, and therefore also the concentration of liposome solution in buffer throughout the second mixing process. Such control of the dilution buffer flow rate advantageously allows for small particle size formation at reduced concentrations.

These processes and the apparatuses for carrying out these direct dilution processes is described in detail in U.S. patent application Ser. No. 11/495,150.

The serum-stable nucleic acid-lipid particles formed using the direct dilution process typically have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

In some embodiments, the particles are formed using detergent dialysis. Without intending to be bound by any particular mechanism of formation, a nucleic acid such as an siRNA is contacted with a detergent solution of cationic lipids to form a coated nucleic acid complex. These coated nucleic acids can aggregate and precipitate. However, the presence of a detergent reduces this aggregation and allows the coated nucleic acids to react with excess lipids (typically, non-cationic lipids) to form particles in which the nucleic acid is encapsulated in a lipid bilayer. Thus, the serum-stable nucleic acid-lipid particles can be prepared as follows:

(a) combining a nucleic acid with cationic lipids in a detergent solution to form a coated nucleic acid-lipid complex;

(b) contacting non-cationic lipids with the coated nucleic acid-lipid complex to form a detergent solution comprising a nucleic acid-lipid complex and non-cationic lipids; and (c) dialyzing the detergent solution of step (b) to provide a solution of serum-stable nucleic acid-lipid particles, wherein the nucleic acid is encapsulated in a lipid bilayer and the particles are serum-stable and have a size of from about 50 to about 150 nm.

An initial solution of coated nucleic acid-lipid complexes is formed by combining the nucleic acid with the cationic lipids in a detergent solution. In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-β-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and nucleic acids will typically be combined to produce a charge ratio (+/−) of about 1:1 to about 20:1, in a ratio of about 1:1 to about 12:1, or in a ratio of about 2:1 to about 6:1. Additionally, the overall concentration of nucleic acid in solution will typically be from about 25 μg/ml to about 1 mg/ml, from about 25 μg/ml to about 200 μg/ml, or from about 50 μg/ml to about 100 μg/ml. The combination of nucleic acids and cationic lipids in detergent solution is kept, typically at room temperature, for a period of time which is sufficient for the coated complexes to form. Alternatively, the nucleic acids and cationic lipids can be combined in the detergent solution and warmed to temperatures of up to about 37° C., about 50° C., about 60° C., or about 70° C. For nucleic acids which are particularly sensitive to temperature, the coated complexes can be formed at lower temperatures, typically down to about 4° C.

In some embodiments, the nucleic acid to lipid ratios (mass/mass ratios) in a formed nucleic acid-lipid particle will range from about 0.01 to about 0.2, from about 0.02 to about 0.1, from about 0.03 to about 0.1, or from about 0.01 to about 0.08. The ratio of the starting materials also falls within this range. In other embodiments, the nucleic acid-lipid particle preparation uses about 400 μg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

The detergent solution of the coated nucleic acid-lipid complexes is then contacted with non-cationic lipids to provide a detergent solution of nucleic acid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide, or sphingomyelin. The acyl groups in these lipids are preferably acyl groups derived from fatty acids having $C_{10}$-$C_{24}$ carbon chains. More preferably, the acyl groups are lauroyl, myristoyl, palmitoyl, stearoyl, or oleoyl. In particularly preferred embodiments, the non-cationic lipids are DSPC, DOPE, POPC, egg phosphatidylcholine (EPC), cholesterol, or a mixture thereof. In the most preferred embodiments, the nucleic acid-lipid particles are fusogenic particles with enhanced properties in vivo and the non-cationic lipid is DSPC or DOPE. In addition, the nucleic acid-lipid particles of the present invention may further comprise cholesterol. In other preferred embodiments, the non-cationic lipids can further comprise polyethylene glycol-based polymers such as PEG 2,000, PEG 5,000, and PEG conjugated to a diacylglycerol, a ceramide, or a phospholipid, as described in, e.g., U.S. Pat. No. 5,820,873 and U.S. Patent Publication No. 20030077829. In further preferred embodiments, the non-cationic lipids can further comprise polyethylene glycol-based polymers such as PEG 2,000, PEG 5,000, and PEG conjugated to a dialkyloxypropyl.

The amount of non-cationic lipid which is used in the present methods is typically from about 2 to about 20 mg of total lipids to 50 µg of nucleic acid. Preferably, the amount of total lipid is from about 5 to about 10 mg per 50 µg of nucleic acid.

Following formation of the detergent solution of nucleic acid-lipid complexes and non-cationic lipids, the detergent is removed, preferably by dialysis. The removal of the detergent results in the formation of a lipid-bilayer which surrounds the nucleic acid providing serum-stable nucleic acid-lipid particles which have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

The serum-stable nucleic acid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the serum-stable nucleic acid-lipid particles can be prepared as follows:

(a) preparing a mixture comprising cationic lipids and non-cationic lipids in an organic solvent;

(b) contacting an aqueous solution of nucleic acid with the mixture in step (a) to provide a clear single phase; and (c) removing the organic solvent to provide a suspension of nucleic acid-lipid particles, wherein the nucleic acid is encapsulated in a lipid bilayer and the particles are stable in serum and have a size of from about 50 to about 150 nm.

The nucleic acids (e.g., siRNA), cationic lipids, and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of nucleic acid and lipids. Suitable solvents include, but are not limited to, chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents may also be used in the present invention.

Contacting the nucleic acid with the organic solution of cationic and non-cationic lipids is accomplished by mixing together a first solution of nucleic acid, which is typically an aqueous solution, and a second organic solution of the lipids. One of skill in the art will understand that this mixing can take place by any number of methods, for example, by mechanical means such as by using vortex mixers.

After the nucleic acid has been contacted with the organic solution of lipids, the organic solvent is removed, thus forming an aqueous suspension of serum-stable nucleic acid-lipid particles. The methods used to remove the organic solvent will typically involve evaporation at reduced pressures or blowing a stream of inert gas (e.g., nitrogen or argon) across the mixture.

The serum-stable nucleic acid-lipid particles thus formed will typically be sized from about 50 nm to about 150 nm, from about 60 nm to about 130 nm, from about 70 nm to about 110 nm, or from about 70 nm to about 90 nm. To achieve further size reduction or homogeneity of size in the particles, sizing can be conducted as described above.

In other embodiments, the methods will further comprise adding non-lipid polycations which are useful to effect the delivery to cells using the present compositions. Examples of suitable non-lipid polycations include, but are limited to, hexadimethrine bromide (sold under the brand name POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine, and polyethyleneimine.

In certain embodiments, the formation of the nucleic acid-lipid particles can be carried out either in a mono-phase system (e.g., a Bligh and Dyer monophase or similar mixture of aqueous and organic solvents) or in a two-phase system with suitable mixing.

When formation of the complexes is carried out in a mono-phase system, the cationic lipids and nucleic acids are each dissolved in a volume of the mono-phase mixture. Combination of the two solutions provides a single mixture in which the complexes form. Alternatively, the complexes can form in two-phase mixtures in which the cationic lipids bind to the nucleic acid (which is present in the aqueous phase), and "pull" it into the organic phase.

In another embodiment, the serum-stable nucleic acid-lipid particles can be prepared as follows:

(a) contacting nucleic acids with a solution comprising non-cationic lipids and a detergent to form a nucleic acid-lipid mixture;

(b) contacting cationic lipids with the nucleic acid-lipid mixture to neutralize a portion of the negative charge of the nucleic acids and form a charge-neutralized mixture of nucleic acids and lipids; and (c) removing the detergent from the charge-neutralized mixture to provide the nucleic acid-lipid particles in which the nucleic acids are protected from degradation.

In one group of embodiments, the solution of non-cationic lipids and detergent is an aqueous solution. Contacting the nucleic acids with the solution of non-cationic lipids and detergent is typically accomplished by mixing together a first solution of nucleic acids and a second solution of the lipids and detergent. One of skill in the art will understand that this mixing can take place by any number of methods, for example, by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to about 5 times the amount of cationic lipid, preferably from about 0.5 to about 2 times the amount of cationic lipid used.

In some embodiments, the nucleic acids are precondensed as described in, e.g., U.S. patent application Ser. No. 09/744,103.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DLinDMA and DLenDMA. These lipids and related analogs are described in U.S. Patent Publication No. 20060083780.

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the nucleic acid-lipid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 50 nm to several microns, about 50 nm to about 150 nm, from about 60 nm to about 130 nm, from about 70 nm to about 110 nm, or from about 70 nm to about 90 nm. To achieve further size reduction or homogeneity of size in the particles, the nucleic acid-lipid particles can be sonicated, filtered, or subjected to other sizing techniques which are used in liposomal formulations and are known to those of skill in the art.

In other embodiments, the methods will further comprise adding non-lipid polycations which are useful to effect the lipofection of cells using the present compositions. Examples of suitable non-lipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In another aspect, the serum-stable nucleic acid-lipid particles can be prepared as follows:

(a) contacting an amount of cationic lipids with nucleic acids in a solution; the solution comprising from about 15-35% water and about 65-85% organic solvent and the amount of cationic lipids being sufficient to produce a +/− charge ratio of from about 0.85 to about 2.0, to provide a hydrophobic nucleic acid-lipid complex;

(b) contacting the hydrophobic, nucleic acid-lipid complex in solution with non-cationic lipids, to provide a nucleic acid-lipid mixture; and (c) removing the organic solvents from the nucleic acid-lipid mixture to provide nucleic acid-lipid particles in which the nucleic acids are protected from degradation.

The nucleic acids (e.g., siRNA), non-cationic lipids, cationic lipids, and organic solvents which are useful in this aspect of the invention are the same as those described for the methods above which used detergents. In one group of embodiments, the solution of step (a) is a mono-phase. In another group of embodiments, the solution of step (a) is two-phase.

In preferred embodiments, the non-cationic lipids are ESM, DSPC, DOPC, POPC, DPPC, monomethyl-phosphatidylethanolamine, dimethyl-phosphatidylethanolamine, DMPE, DPPE, DSPE, DOPE, DEPE, SOPE, POPE, PEG-based polymers (e.g., PEG 2000, PEG 5000, PEG-modified diacylglycerols, or PEG-modified dialkyloxypropyls), cholesterol, or combinations thereof. In still other preferred embodiments, the organic solvents are methanol, chloroform, methylene chloride, ethanol, diethyl ether or combinations thereof.

In one embodiment, the nucleic acid is an siRNA as described herein; the cationic lipid is DLindMA, DLenDMA, DODAC, DDAB, DOTMA, DOSPA, DMRIE, DOGS, or combinations thereof; the non-cationic lipid is ESM, DOPE, PEG-DAG, DSPC, DPPC, DPPE, DMPE, monomethyl-phosphatidylethanolamine, dimethyl-phosphatidylethanolamine, DSPE, DEPE, SOPE, POPE, cholesterol, or combinations thereof (e.g., DSPC and PEG-DAA); and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to about 15 times the amount (on a mole basis) of cationic lipids which was used to provide the charge-neutralized nucleic acid-lipid complex. Preferably, the amount is from about 0.5 to about 9 times the amount of cationic lipids used.

In one embodiment, the nucleic acid-lipid particles preparing according to the above-described methods are either net charge neutral or carry an overall charge which provides the particles with greater gene lipofection activity. Preferably, the nucleic acid component of the particles is a nucleic acid which interferes with the production of an undesired protein. In other preferred embodiments, the non-cationic lipid may further comprise cholesterol.

A variety of general methods for making SNALP-CPLs (CPL-containing SNALPs) are discussed herein. Two general techniques include "post-insertion" technique, that is, insertion of a CPL into for example, a pre-formed SNALP, and the "standard" technique, wherein the CPL is included in the lipid mixture during for example, the SNALP formation steps. The post-insertion technique results in SNALPs having CPLs mainly in the external face of the SNALP bilayer membrane, whereas standard techniques provide SNALPs having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPL, are taught, for example, in U.S. Pat. Nos.

5,705,385; 6,586,410; 5,981,501; 6,534,484; and 6,852,334; U.S. Patent Publication No. 20020072121; and PCT Publication No. WO 00/62813.

VI. Kits

The present invention also provides nucleic acid-lipid particles in kit form. The kit may comprise a container which is compartmentalized for holding the various elements of the nucleic acid-lipid particles (e.g., the nucleic acids and the individual lipid components of the particles). In some embodiments, the kit may further comprise an endosomal membrane destabilizer (e.g., calcium ions). The kit typically contains the nucleic acid-lipid particle compositions of the present invention, preferably in dehydrated form, with instructions for their rehydration and administration. In certain instances, the particles and/or compositions comprising the particles may have a targeting moiety attached to the surface of the particle. Methods of attaching targeting moieties (e.g., antibodies, proteins) to lipids (such as those used in the present particles) are known to those of skill in the art.

VII. Administration of Nucleic Acid-Lipid Particles

Once formed, the serum-stable nucleic acid-lipid particles of the present invention are useful for the introduction of nucleic acids (e.g., siRNA) into cells. Accordingly, the present invention also provides methods for introducing a nucleic acid (e.g., siRNA) into a cell. The methods are carried out in vitro or in vivo by first forming the particles as described above and then contacting the particles with the cells for a period of time sufficient for delivery of the nucleic acid to the cells to occur.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

The nucleic acid-lipid particles of the present invention can be administered either alone or in a mixture with a pharmaceutically-acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically-acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically-acceptable" refers to molecular entities and compositions that do not produce an allergic or similar untoward reaction when administered to a human.

The pharmaceutically-acceptable carrier is generally added following particle formation. Thus, after the particle is formed, the particle can be diluted into pharmaceutically-acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

A. In Vivo Administration

Systemic delivery for in vivo therapy, i.e., delivery of a therapeutic nucleic acid to a distal target cell via body systems such as the circulation, has been achieved using nucleic acid-lipid particles such as those disclosed in PCT Publication No. WO 96/40964 and U.S. Pat. Nos. 5,705,385; 5,976,567; 5,981,501; and 6,410,328. This latter format provides a fully encapsulated nucleic acid-lipid particle that protects the nucleic acid from nuclease degradation in serum, is nonimmunogenic, is small in size, and is suitable for repeat dosing.

For in vivo administration, administration can be in any manner known in the art, e.g., by injection, oral administration, inhalation (e.g., intranasal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.*, 101:512 (1983); Mannino et al., *Biotechniques*, 6:682 (1988); Nicolau et al., *Crit. Rev. Ther. Drug Carrier Syst.*, 6:239 (1989); and Behr, *Acc. Chem. Res.*, 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid-nucleic acid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)).

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.*, 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the nucleic acid-lipid formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the nucleic acid-lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the nucleic acid-lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of the packaged nucleic acid (e.g., siRNA) suspended in diluents such as water, saline, or PEG 400; (b) capsules, sachets, or tablets, each containing a predetermined amount of the nucleic acid (e.g., siRNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the nucleic acid (e.g., siRNA) in a flavor, e.g., sucrose, as well as pastilles comprising the nucleic acid (e.g., siRNA) in an inert base, such as gelatin and glycerin or sucrose and acacia emulsions, gels, and the like containing, in addition to the nucleic acid (e.g., siRNA), carriers known in the art.

In another example of their use, nucleic acid-lipid particles can be incorporated into a broad range of topical dosage forms. For instance, the suspension containing the nucleic acid-lipid particles can be formulated and administered as gels, oils, emulsions, topical creams, pastes, ointments, lotions, foams, mousses, and the like.

When preparing pharmaceutical preparations of the nucleic acid-lipid particles of the invention, it is preferable to use quantities of the particles which have been purified to reduce or eliminate empty particles or particles with nucleic acid associated with the external surface.

The methods of the present invention may be practiced in a variety of hosts. Preferred hosts include mammalian species, such as avian (e.g., ducks), primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of nucleic acid to lipid, the particular nucleic acid used, the disease state being diagnosed, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In Vitro Administration

For in vitro applications, the delivery of nucleic acids (e.g., siRNA) can be to any cell grown in culture, whether of plant or animal origin, vertebrate or invertebrate, and of any tissue or type. In preferred embodiments, the cells are animal cells, more preferably mammalian cells, and most preferably human cells.

Contact between the cells and the nucleic acid-lipid particles, when carried out in vitro, takes place in a biologically compatible medium. The concentration of particles varies widely depending on the particular application, but is generally between about 1 μmol and about 10 mmol. Treatment of the cells with the nucleic acid-lipid particles is generally carried out at physiological temperatures (about 37° C.) for periods of time of from about 1 to 48 hours, preferably of from about 2 to 4 hours.

In one group of preferred embodiments, a nucleic acid-lipid particle suspension is added to 60-80% confluent plated cells having a cell density of from about $10^3$ to about $10^5$ cells/ml, more preferably about $2 \times 10^4$ cells/ml. The concentration of the suspension added to the cells is preferably of from about 0.01 to 0.2 μg/ml, more preferably about 0.1 μg/ml.

Using an Endosomal Release Parameter (ERP) assay, the delivery efficiency of the SNALP or other lipid-based carrier system can be optimized. An ERP assay is described in detail in U.S. Patent Publication No. 20030077829. More particularly, the purpose of an ERP assay is to distinguish the effect of various cationic lipids and helper lipid components of SNALPs based on their relative effect on binding/uptake or fusion with/destabilization of the endosomal membrane. This assay allows one to determine quantitatively how each component of the SNALP or other lipid-based carrier system affects delivery efficiency, thereby optimizing the SNALPs or other lipid-based carrier systems. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an interfering RNA. In other instances, an ERP assay can be adapted to measure downregulation of transcription or translation of a target sequence in the presence or absence of an interfering RNA (e.g., siRNA). By comparing the ERPs for each of the various SNALPs or other lipid-based formulations, one can readily determine the optimized system, e.g., the SNALP or other lipid-based formulation that has the greatest uptake in the cell.

C. Cells for Delivery of Interfering RNA

The compositions and methods of the present invention are used to treat a wide variety of cell types, in vivo and in vitro. Suitable cells include, e.g., hematopoietic precursor (stem) cells, fibroblasts, keratinocytes, hepatocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like.

In vivo delivery of nucleic acid-lipid particles encapsulating an interfering RNA (e.g., siRNA) is suited for targeting cells of any cell type. The methods and compositions can be employed with cells of a wide variety of vertebrates, including mammals, such as, e.g. canines, felines, equines, bovines, ovines, caprines, rodents (e.g., mice, rats, and guinea pigs), lagomorphs, swine, and primates (e.g. monkeys, chimpanzees, and humans).

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

D. Detection of SNALPs

In some embodiments, the nucleic acid-lipid particles are detectable in the subject at about 8, 12, 24, 48, 60, 72, or 96 hours, or 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of the interfering RNA (e.g., siRNA) sequence, detection of the target sequence of interest (i.e., by detecting expression or reduced expression of the sequence of interest), or a combination thereof.

1. Detection of Particles

Nucleic acid-lipid particles can be detected using any methods known in the art. For example, a label can be coupled directly or indirectly to a component of the SNALP or other carrier system using methods well-known in the art. A wide variety of labels can be used, with the choice of label depending on sensitivity required, ease of conjugation with the SNALP component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., siRNA) are detected and quantified herein by any of a number of means well-known to those of skill in the art. The detection of nucleic acids proceeds by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA™) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), *C& EN* 36; The *Journal Of NIH Research*, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241: 1077 (1988); Van Brunt, *Biotechnology*, 8:291 (1990); Wu and Wallace, *Gene*, 4:560 (1989); Barringer et al., *Gene*, 89:117 (1990); and Sooknanan and Malek, *Biotechnology*, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of ploynucleotides, where necessary, is typically performed by either native acrylamide gel electrophoresis or by anion exchange HPLC as described in Pearson et al., *J. Chrom.*, 255:137 149 (1983). The sequence of the synthetic polynucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

VIII. Examples

The present invention will be described in greater detail by way of the following examples. The following examples are offered for illustrative purposes, and are not intended to limit the present invention in any manner. Those of skill in the art will readily recognize a variety of noncritical parameters which can be changed or modified to yield essentially the same results.

Example 1

Design of Non-inflammatory Synthetic siRNA Mediating Potent Gene Silencing In Vivo This example illustrates that minimal 2'-O-methyl (2'OMe) modifications at selective positions in one strand of the siRNA duplex are sufficient to reduce or completely abrogate the immunostimulatory activity of siRNA, irrespective of its sequence. In fact, by restricting 2'OMe modifications to the non-targeting sense strand of the siRNA duplex, the immunostimulatory activity of siRNA can be abolished while retaining full RNAi activity.

Results

Figure 2A:
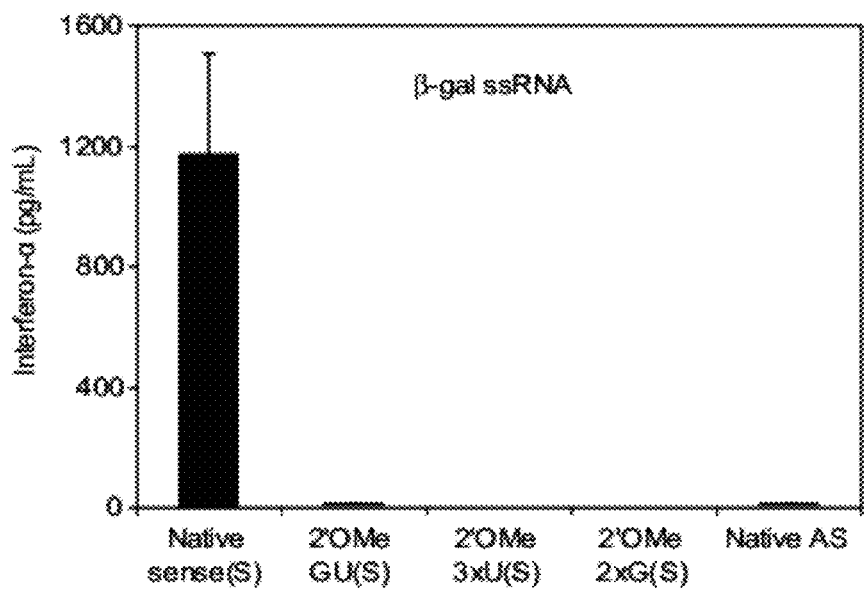
FIG. 2 illustrates data demonstrating that immune stimulation by ssRNA and siRNA complexed with polyethylenimine (PEI) is abrogated by 2'OMe modification. Interferon-α responses from human PBMC cultures treated with PEI complexed (FIG. 2A) native β-gal sense (S), antisense (AS), and 2'OMe-modified sense ssRNAs and (FIG. 2B) native, 2'OMe GU(S), and AC(AS) modified β-gal control siRNA duplexes. RNA were added at a final concentration of 225 nM and IFN-α assayed in culture supernatants after 16 hours. RNA sequences are shown in Table 1.

2'OMe modifications within ssRNA abrogate immune stimulation. To examine the extent and type of chemical modification required to inhibit immune cell activation by RNA, 2'OMe nucleotides were selectively introduced into the GU-rich immunostimulatory motif of a single-stranded RNA polynucleotide (ssRNA) derived from a β-galactosidase (β-gal) siRNA (Judge et al., *Nat. Biotechnol.*, 23:457-462 (2005)). Polynucleotide sequences used in this study are provided in Table 1. 2'OMe modification of the 5 nucleotides comprising the immunostimulatory 5'-UGUGU-3' motif (2'OMe GU) in the β-gal sense ssRNA completely abrogated interferon-alpha (IFN-α) induction when human peripheral blood mononuclear cell (PBMC) cultures were treated with lipid encapsulated ssRNA (FIG. 1A). Inhibition of the interferon response was also achieved by selectively modifying either the two guanosine (2'OMe 2×G) or the three uridine (2'OMe 3×U) nucleotides within the motif. The inhibitory effect of 2'-O-methylation did not appear to require the direct modification of the nucleotides within the immunostimulatory GU rich motif since selective modification of the two guanosine residues 3' to the UGUGU motif, towards the end of the β-gal ssRNA (2'OMe 2×G 3'), also resulted in complete abrogation of the interferon response in PBMC cultures (FIG. 1A). As described previously, the unmodified complementary antisense (AS) ssRNA sequence was inherently non-immunostimulatory in these assays (Judge et al., supra). Similar results were obtained when the cationic polymer polyethylenimine (PEI) was used to deliver the β-gal ssRNA to PBMC (FIG. 2A).

Figure 1B:
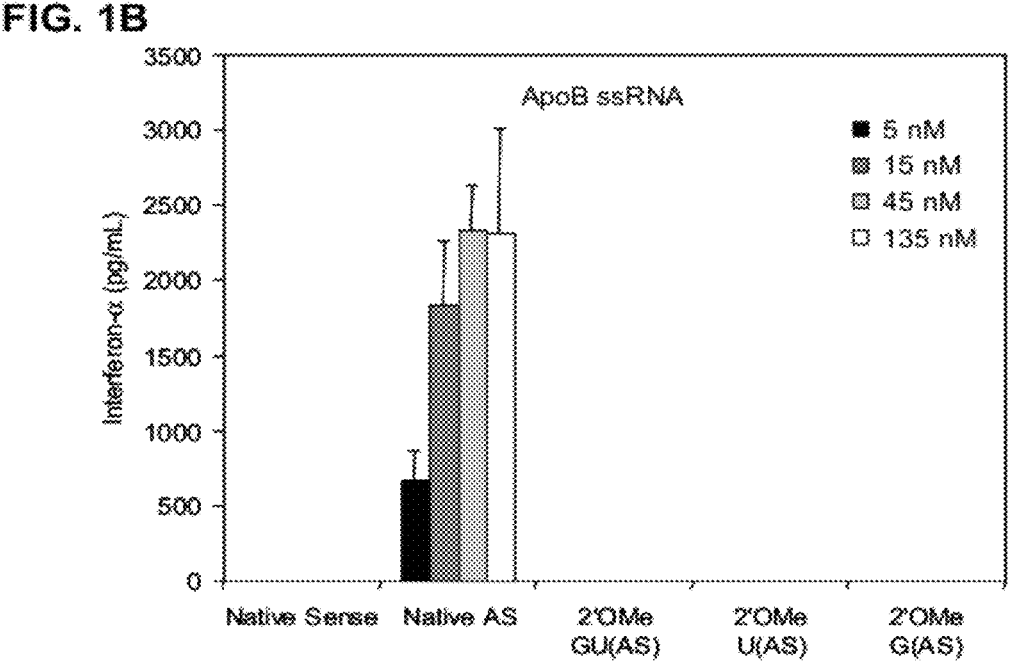

A similar approach was applied to the modification of the constituent 21- and 23-base strands of an siRNA duplex targeting human and mouse ApoB (Soutschek et al., *Nature*, 432:173-178 (2004)). As predicted by its GU-rich nucleotide sequence (Heil et al., *Science*, 303:1526-1529 (2004); Judge et al., supra), unmodified ApoB (AS) ssRNA stimulated a strong IFN-α response in PBMC cultures, even at low concentrations (FIG. 1B). This response was fully inhibited by 2'OMe modification of either the 5 nucleotides comprising the 5'-GUGUG-3' motif (2'OMe GU) or the 6 guanosine (2'OMe G) or 7 uridine (2'OMe U) residues in ApoB (AS) ssRNA (FIG. 1B). The unmodified, complementary ApoB sense polynucleotide (ApoB (S)) encapsulated in lipid particles did not induce IFN-α in PBMC (FIG. 1B), although high doses of this polynucleotide delivered as PEI polyplexes was found to activate a cytokine response. This weak response to PEI-complexed ApoB (S) ssRNA was also inhibited by 2'OMe-uridine modification. These findings demonstrate that the selective incorporation of 2'OMe-modified nucleotides within ssRNA is sufficient to prevent stimulation of the interferon response from innate immune cells.

TABLE 1

RNA polynucleotides used in this study.

| Name | Strand | Sequence 5'-3' | SEQ ID NO: |
|---|---|---|---|
| β-gal | Native (S) | UUGAUGUGUUUAGUCGCUAUU | 2 |
| | 2'OMe GU(S) | UUGAUGUGUUUAGUCGCUAUU | 3 |
| | 2'OMe 3xU(S) | UUGAUGUGUUUAGUCGCUAUU | 4 |
| | 2'OMe 2xG(S) | UUGAUGUGUUUAGUCGCUAUU | 5 |
| | 2'OMe 2xG 3'(S) | UUGAUGUGUUUAGUCGCUAUU | 6 |
| | Native (AS) | *UAGCGACUAAACACAUCAALTU | 7 |
| | 2'OMe AC(AS) | *UAGCGACUAAACACAUCAAUU | 8 |

TABLE 1-continued

RNA polynucleotides used in this study.

| Name | Strand | Sequence 5'-3' | SEQ ID NO: |
|---|---|---|---|
| ApoB | Native (S) | GUCAUCACACUGAAUACCAAU | 9 |
|  | 2'OMe U(S) | GUCAUCACACUGAAUACCAAU | 10 |
|  | 2'OMe G(S) | GUCAUCACACUGAAUACCAAU | 11 |
|  | 2'OMe C(S) | GUCAUCACACUGAAUACCAAU | 12 |
|  | 2'OMe A(S) | GUCAUCACACUGAAUACCAAU | 13 |
|  | Native (AS) | *AUUGGUAUUCAGUGUGAUGA-CAC | 14 |
|  | 2'OMe GU(AS) | *AUUGGUAUUCAGUGUGAUGACAC | 15 |
|  | 2'OMe U(AS) | *AUGGUAUUCAGUGUGAUGACAC | 16 |
|  | 2'OMe G(AS) | *AUUGGUAUUCAGUGUGAUGACAC | 17 |
| ApoB mismatch | Native (S) | GUGAUCAGACUCAAUACGAAU | 18 |
|  | 2'OMe U(S) | GUGAUCAGACUCAAUACGAAU | 19 |
|  | Native (AS) | *AUUCGUAUUGAGUCUGAUCA-CAC | 20 |
|  | 2'OMe GU(AS) | *AUUCGUAUUGAGUCUGAUCACAC | 21 |
| vFLIP | Native (S) | GUGGUAUUGUUCCUCCUAAdTdT | 22 |
|  | 2'OMe GU(S) | GUGGUAUUGUUCCUCCUAAdTdT | 23 |
|  | 2'OMe U(S) | GUGGUAUUGUUCCUCCUAAdTdT | 24 |
|  | Native (AS) | *UUAGGAGGAACAAUAC-CACdTdT | 25 |
|  | 2'OMe U(AS) | *UUAGGAGGAACAAUACCACdTdT | 26 |
|  | 2'OMe C(AS) | *UUAGGAGGAACAAUACCACdTdT | 27 |

Unmodified (native) and 2'OMe-modified RNA polynucleotides corresponding to the sense (S) and antisense (AS) strands of β-gal, ApoB, ApoB mismatch, and vFLIP siRNA. 2'OMe-modified nucleotides are indicated in bold and underlined. Asterisks represent 5' phosphates. "dT" = deoxythymidine.

Figure 2B:
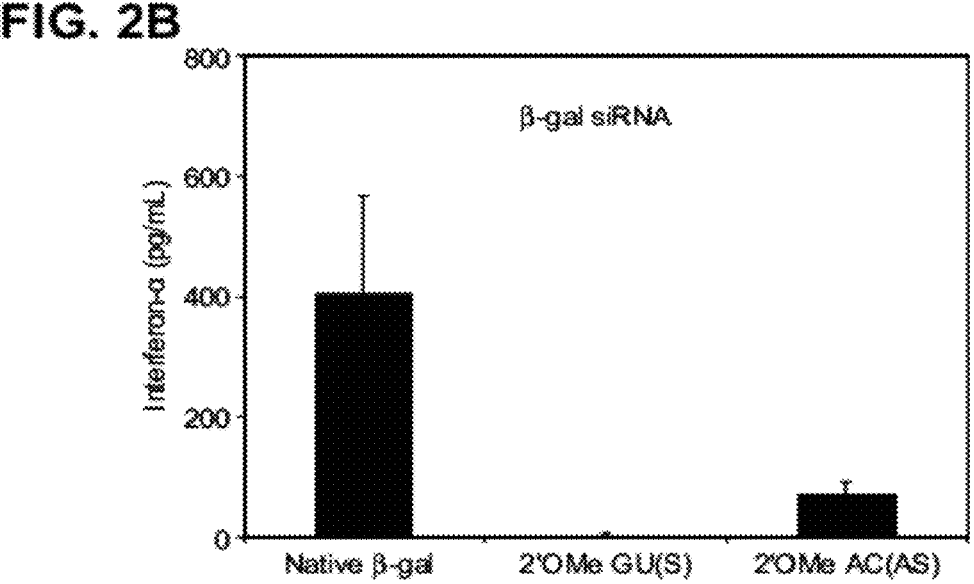
Figure 3A:
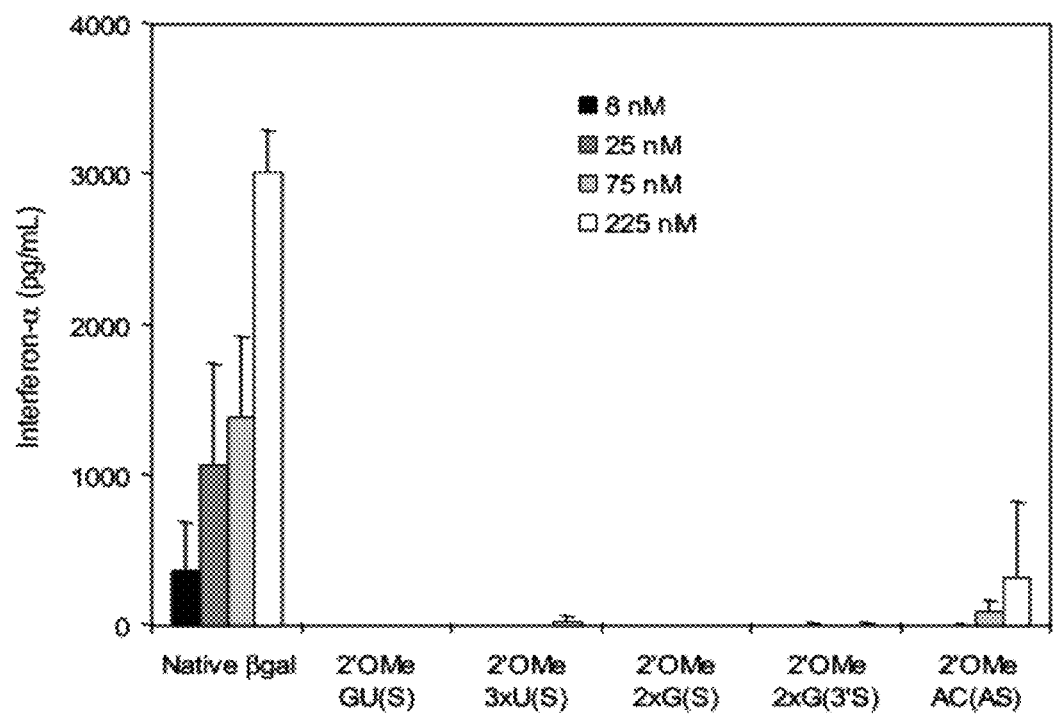
(FIGS. 3A, 3B) IFN-α and (FIG. 3C) TNF-α induction from human PBMC cultured with increasing concentrations (25-675 nM) of encapsulated (A) β-gal or (B, C) ApoB or ApoB mismatch siRNA. Cytokine responses to unmodified (native) siRNAs were compared to duplexes containing 2'OMe U, G, C, or A residues in either the sense (S) or antisense (AS) strands as indicated (see, Table 1 for siRNA sequences). Secreted cytokines were assayed after a 24 hour culture. Values are mean+SD. of triplicate cultures.
Figure 3B:
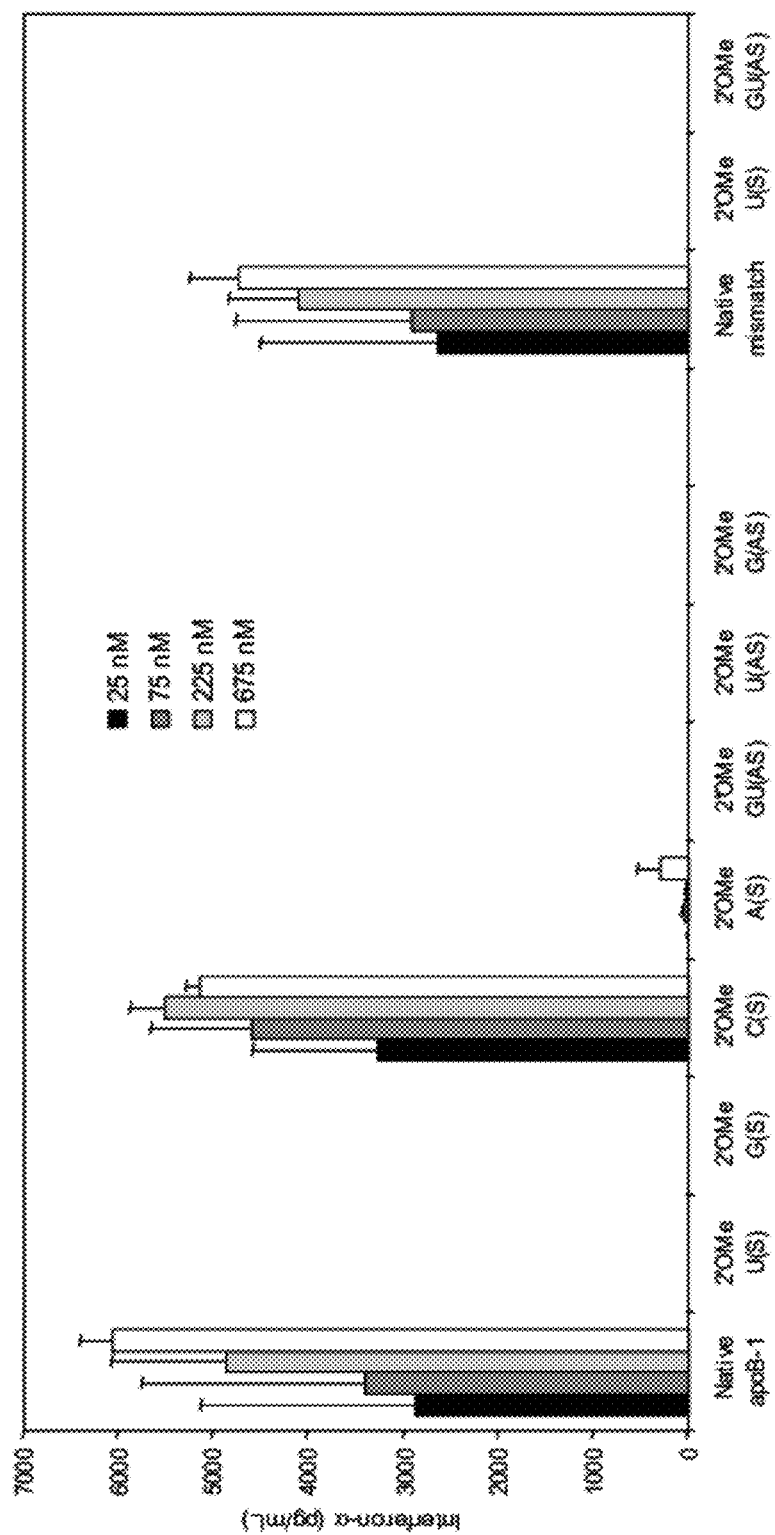
Figure 3C:
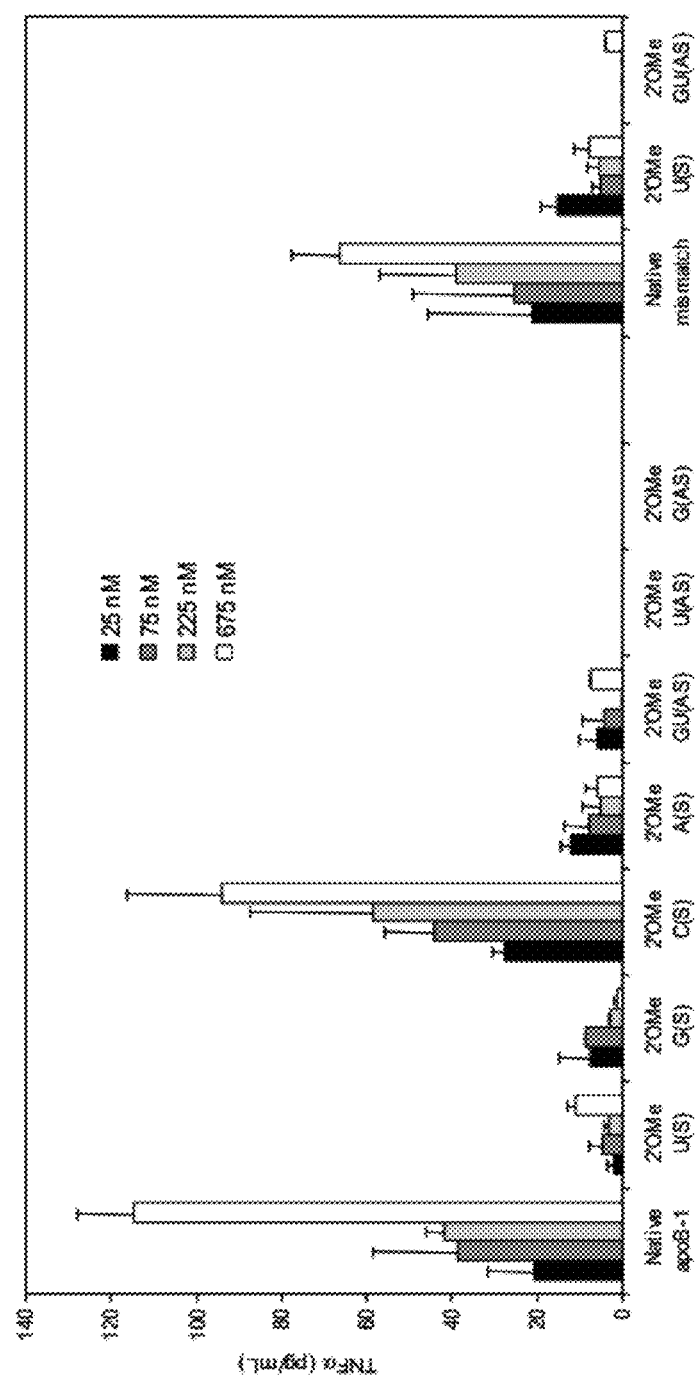
FIG. 3 illustrates data demonstrating that selective 2'OMe modification to siRNA duplexes abrogates cytokine induction in human PBMC.

Selective nucleotide modifications within siRNA abrogate immune stimulation. To examine whether selective 2'OMe modifications within siRNA duplexes also inhibited immune stimulation, a series of β-gal and ApoB siRNA comprising 2'OMe-modified sense or AS strands annealed to their complementary unmodified polynucleotides were generated (see, Table 1). Lipid encapsulated double-stranded β-gal siRNA comprising either the 2'OMe-modified UGUGU, 2×G, or 3×U sense strand annealed with the unmodified (non-immunostimulatory) AS strand induced no detectable interferon response from human PBMC (FIG. 3A). Interestingly, selective 2'OMe modification of the complementary 5'-ACACA-3' motif in the AS strand, juxtaposed to the unmodified 5'-UGUGU-3' motif in the sense strand, also diminished the level of IFN-α induction despite the annealed duplex containing the unmodified (immunostimulatory) sense strand (FIG. 3A). Similar results were obtained when PEI was used to deliver the β-gal siRNA to PBMC (FIG. 2B). Likewise, unmodified ApoB siRNA induced a strong IFN-α response in PBMC and this reaction was completely abrogated when 2'OMe GU, U, or G modified AS strands were incorporated in the ApoB duplex (FIG. 3B). Strikingly, modified ApoB siRNA containing 2'OMe G or U modified sense strands annealed to the unmodified, immunostimulatory AS strand were also rendered non-immunostimulatory (FIG. 3B). Abrogation of cytokine induction by 2'OMe G or U modifications to the sense strands of modified ApoB siRNA appeared absolute, as even high concentrations (675 nM, ~9 μg/ml) of modified siRNA failed to induce IFN-α or inflammatory cytokines such as TNF in PBMC cultures (FIGS. 3B and 3C).

The inhibitory effect of 2'-O-methylation on immune stimulation by siRNA was not observed with all patterns of modification, however, as ApoB siRNA containing 2'OMe-modified cytidine residues induced levels of cytokines similar to those induced by the native duplex (FIG. 3B). The incorporation of 2'OMe adenosine resulted in significant, but not absolute, inhibition of the cytokine response. These differences did not simply reflect the extent of chemical modification, as the 2'OMe G, U, C, and A modified ApoB contain 2, 5, 6, and 8 modified nucleotides in the sense strand, respectively. This suggests that unmodified U and/or G residues may play a key role in immune recognition of the duplex siRNA.

Figure 4C:
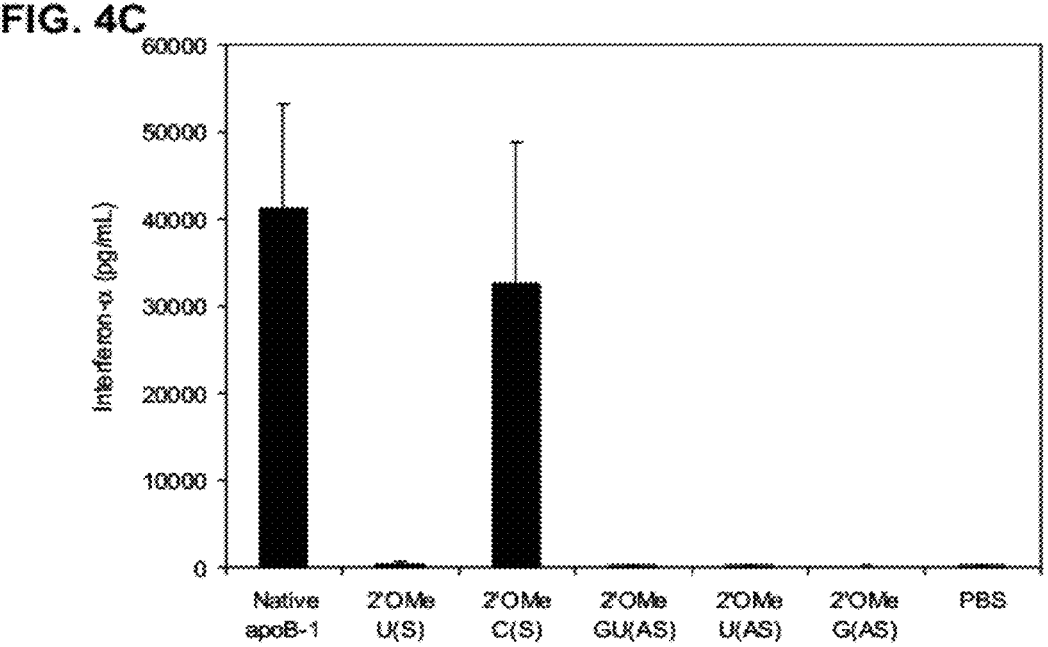
(FIGS. 4A, 4C, 4E, 4F) Serum IFN-α and (FIGS. 4B, 4D) TNF-α and IL-6 levels 6 hours after intravenous administration of encapsulated (FIGS. 4A, 4B) β-gal, (FIGS. 4C, 4D) ApoB, (FIG. 4E) ApoB mismatch, or (FIG. 4F) vFLIP siRNA. Responses to unmodified (native) siRNAs were compared to duplexes containing 2'OMe U, G, or C residues in either the sense (S) or antisense (AS) strands as indicated (see, Table 1 for siRNA sequences). All mice received 40 µg encapsulated siRNA. Values are mean+SD from 3-4 animals. Lower levels of quantitation are 75 pg/mL for IFN-α, 30 pg/mL for TNF-α, and 60 pg/mL for IL-6.
Figure 4D:
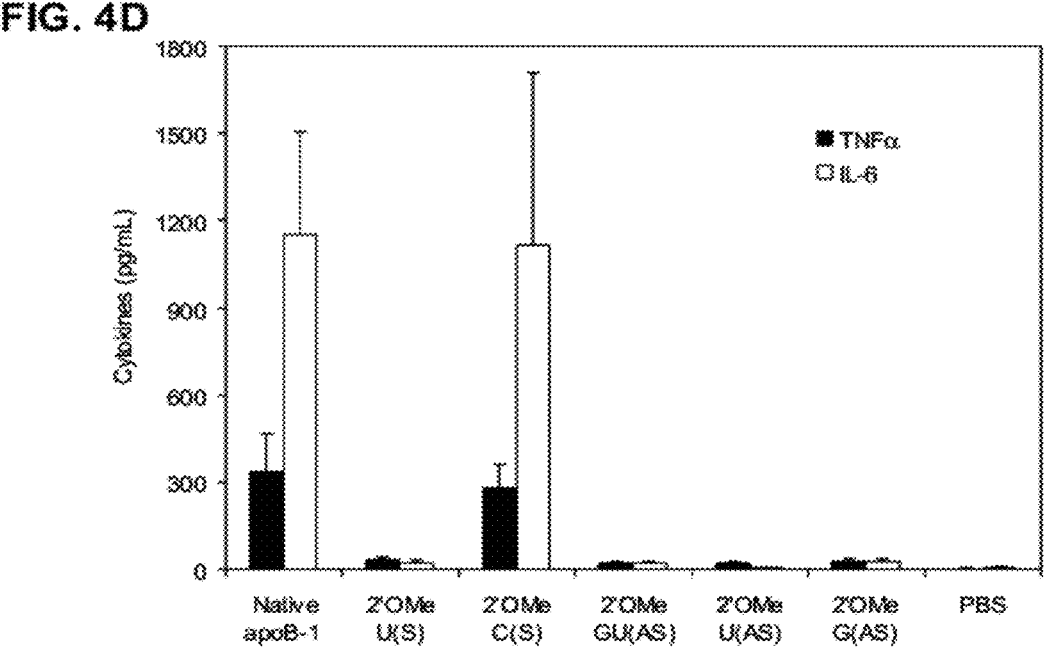
FIG. 4 illustrates data demonstrating that selective 2'OMe modification to siRNA duplexes abrogates cytokine induction in vivo.
Figure 4E:
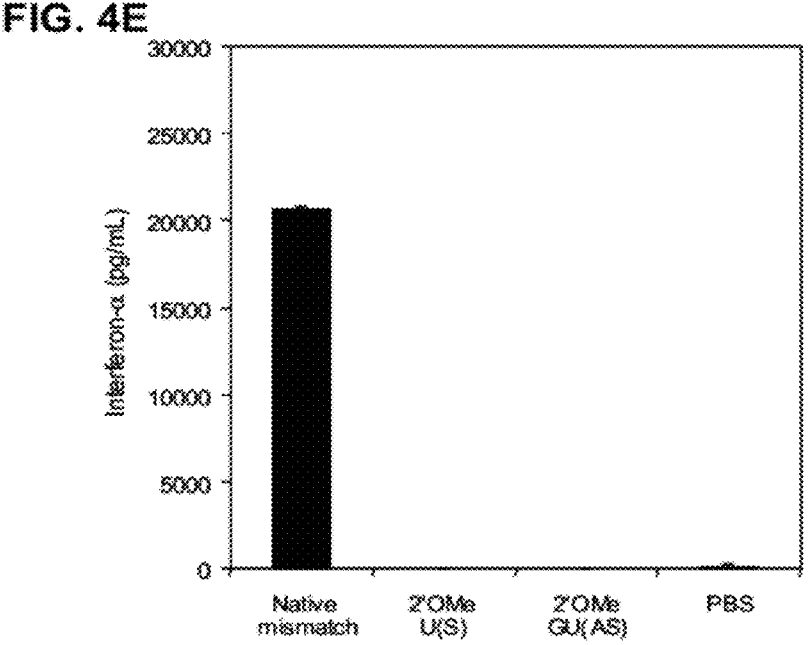
Figure 4F:
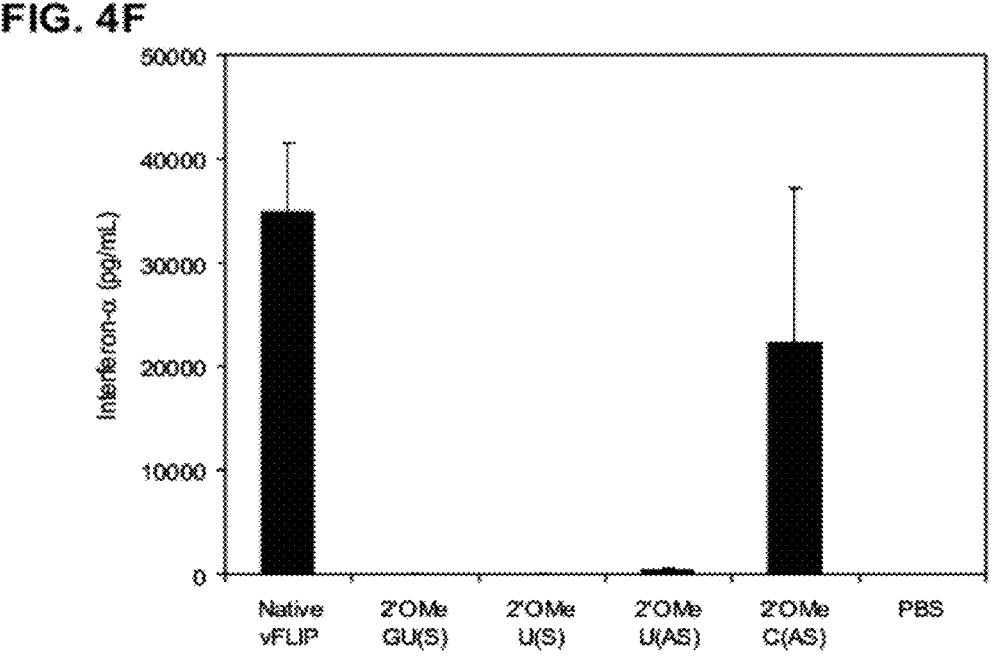
Figure 5A:
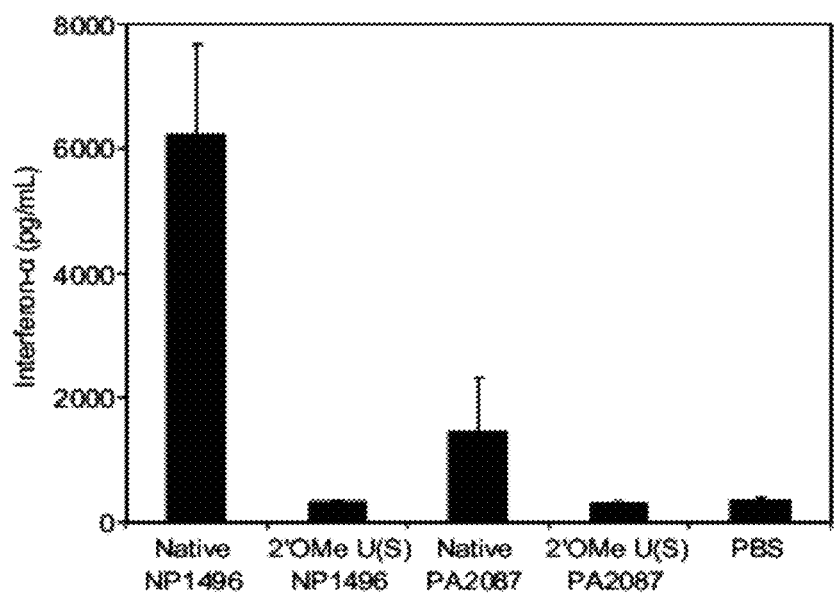
FIG. 5 illustrates data demonstrating that the cytokine response to siRNA in vivo is abrogated by selective incorporation of 2'OMe-uridines into the siRNA sense strand. Serum interferon-α levels in mice were determined 6 hours after intravenous administration of SNALPs containing siRNA targeting FIG. 5A influenza nucleoprotein (NP1496) and polymerase (PA2087) or (FIG. 5B) cyclophilin B (Cyp B). Responses to native, unmodified siRNA were compared to 2'OMe U(S) modified duplexes. Sequences are provided in Table 2.
Figure 5B:
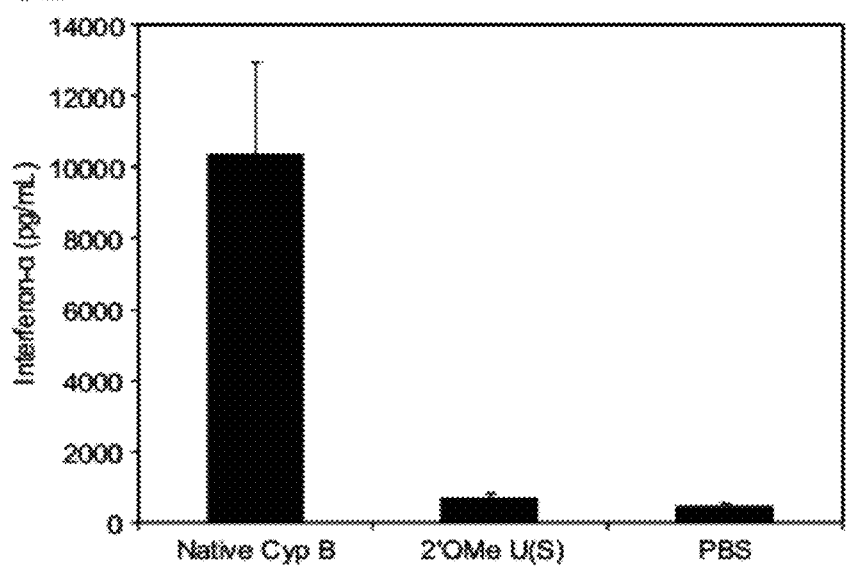
Figure 6A:
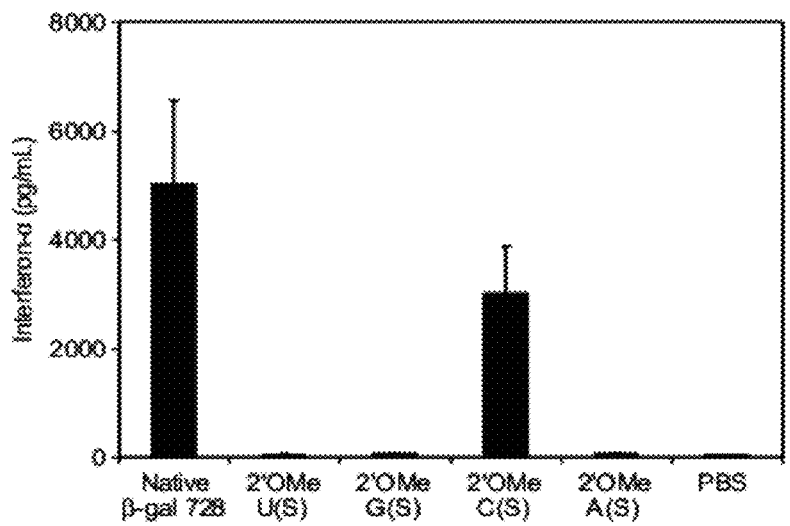
(FIG. 6A) Interferon-α induction in mice 6 hours after administration of 20 µg siRNA encapsulated in SNALPs.
Figure 6B:
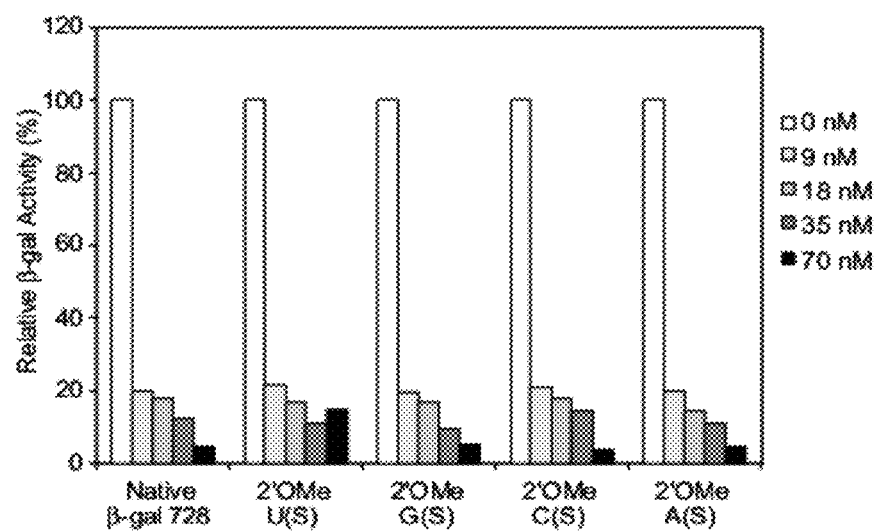
(FIG. 6B) In vitro RNA interference activity of the same β-gal 728 SNALP formulations. RNAi assays were performed in Neuro2A cells stably transfected with the *E. coli* LacZ gene. β-gal activity was assessed 48 hours after exposure to SNALPs and mean values expressed relative to PBS-treated cells. The SNALPs used in these studies comprised the lipids cholesterol:DSPC:DLinDMA:PEG-C-DMA in the molar ratio 48:10:40:2 and had particle sizes ranging from 80-90 nm in diameter. RNA sequences are provided in Table 2.
Figure 7A:
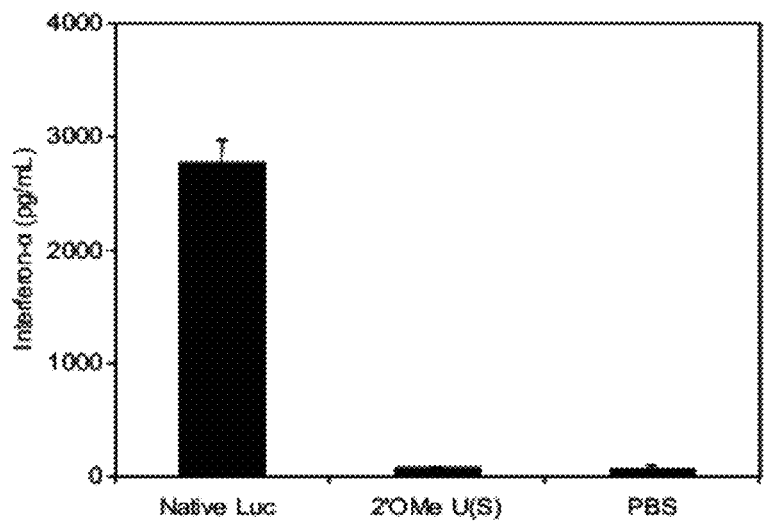
(FIG. 7A) Interferon-α induction in mice 6 hours after administration of 20 µg siRNA encapsulated in SNALPs.
Figure 7B:
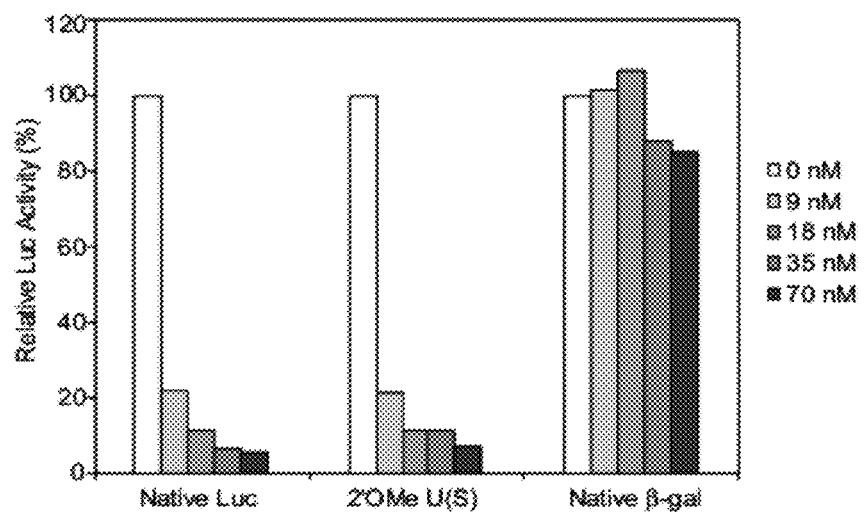
(FIG. 7B) In vitro RNA interference activity of Luc SNALP formulations. RNAi assays were performed in Neuro2A cells stably transfected with firefly luciferase. Luciferase activity was assessed 48 hours after exposure to SNALPs and mean values expressed relative to PBS-treated cells. The SNALPs used in these studies comprised the lipids cholesterol:DSPC:DLinDMA:PEG-C-DMA in the molar ratio 48:10:40:2 and had particle sizes ranging from 75-85 nm in diameter. RNA sequences are provided in Table 2.

To confirm that this approach to siRNA design would successfully inhibit inflammatory responses to siRNA in vivo, the immunostimulatory activity of the 2'OMe-modified β-gal and ApoB siRNA was assessed in mice. Intravenous administration of lipid encapsulated β-gal (FIGS. 4A and 4B) or ApoB (FIGS. 4C and 4D) siRNA containing 2'OMe-modified guanosine or uridine residues in either sense or antisense strands caused no detectable increase in serum IFN-α or inflammatory cytokines such as TNF. This was in marked contrast to the unmodified or cytosine modified siRNAs that induced substantial elevations in the level of these cytokines. These striking effects of selective 2'OMe modification were confirmed by applying a similar approach to modifying ApoB mismatch (Soutschek et al., *Nature*, 432:173-178 (2004)) and vFLIP (Guasparri et al., *J. Exp. Med.*, 199:993-1003 (2004)) siRNA sequences (see, Table 1). For the ApoB mismatch (FIG. 4E) and vFLIP (FIG. 4F) siRNA duplexes, modifying either the GU-rich regions or only the uridine residues in either one of the RNA strands completely abrogated cytokine induction by the siRNA duplex. Inhibition of the cytokine response to modified ApoB mismatch siRNA was also confirmed in human PBMC cultures (FIGS. 3B and 3C). As with ApoB, selective incorporation of 2'OMe cytosine residues into vFLIP siRNA did not substantially reduce the IFN-α response (FIG. 4F). Similar results have been consistently obtained for each siRNA sequence tested, in which the introduction of 2'OMe-uridine or guanosine residues generates non-inflammatory siRNA duplexes. For example, FIGS. 5-7 show that the introduction of 2'OMe-uridine or guanosine residues produces non-inflammatory siRNA duplexes for each of the five additional siRNA sequences provided in Table 2. Taken together, these findings support the conclusion that the underlying mechanism for immune recognition of short RNA duplexes is conserved between mouse and humans (Judge et al., supra; Hornung et al., *Nat. Med.*, 11:263-270 (2005)). These results indicate that this mechanism can be profoundly disrupted in either species by the incorporation of as few as two 2'OMe-modified nucleotides within either strand of an siRNA duplex.

TABLE 2

Additional RNA polynucleotides used in this study.

| Name | Strand | Sequence 5'-3' | SEQ ID NO: |
|---|---|---|---|
| β-gal 728 | Native (S) | CUACACAAAUCAGCGAUUUUU | 28 |
| | 2'OMe U(S) | CUACACAAAUCAGCGAUUUUU | 29 |
| | 2'OMe G(S) | CUACACAAACAGCGAUUUUU | 30 |
| | 2'OMe C(S) | CUACACAAUCAGCGAUUUUU | 31 |
| | 2'OMe A(S) | CUACACAAAUCAGCGAUUUUU | 32 |
| | Native (AS) | *AAAUCGCUGAUUUGUGUAGUU | 33 |
| Luciferase (Luc) | Native (S) | GAUUAUGUCCGGUUAUGUAUU | 34 |
| | 2'OMe U(S) | GAUUAUGUCCGGUUAUGUAUU | 35 |
| | Native (AS) | *UACAUAACCGGACAUAAUCUU | 36 |
| Cyclophilin B (Cyp B) | Native (S) | GGAAAGACUGUUCCAAAAAUU | 37 |
| | 2'OMe U(S) | GGAAAGACUGUUCCAAAAAUU | 38 |
| | Native (AS) | *UUUTJUGGAACAGUCUUUCCUU | 39 |
| NP1496 | Native (S) | GGAUCUUAUUUCUUCGGAGdTdT | 40 |
| | 2'OMe U(S) | GGAUCUUAUUUCUUCGGAGdTdT | 41 |
| | Native (AS) | *CUCCGAAGAAAUAAGAUCCdTdT | 42 |
| PA2087 | Native (S) | GCAAUUGAGGAGUGCCUGAdTdT | 43 |
| | 2'OMe U(S) | GCAAUUGAGGAGUGCCUGAdTdT | 44 |
| | Native (AS) | *UCAGGCACUCCUCAAUUGCdTdT | 45 |

Unmodified (native) and 2'OMe-modified RNA polynucleotides corresponding to the sense (S) and antisense (AS) strands of β-gal, luciferase (Luc), cyclophilin B (Cyp B), influenza nucleocapsid protein (NP), and influenza polymerase (PA) siRNA.
2'OMe-modified nucleotides are indicated in bold and underlined. Asterisks represent 5' phosphates. "dT" = deoxythymidine.

Figure 8:
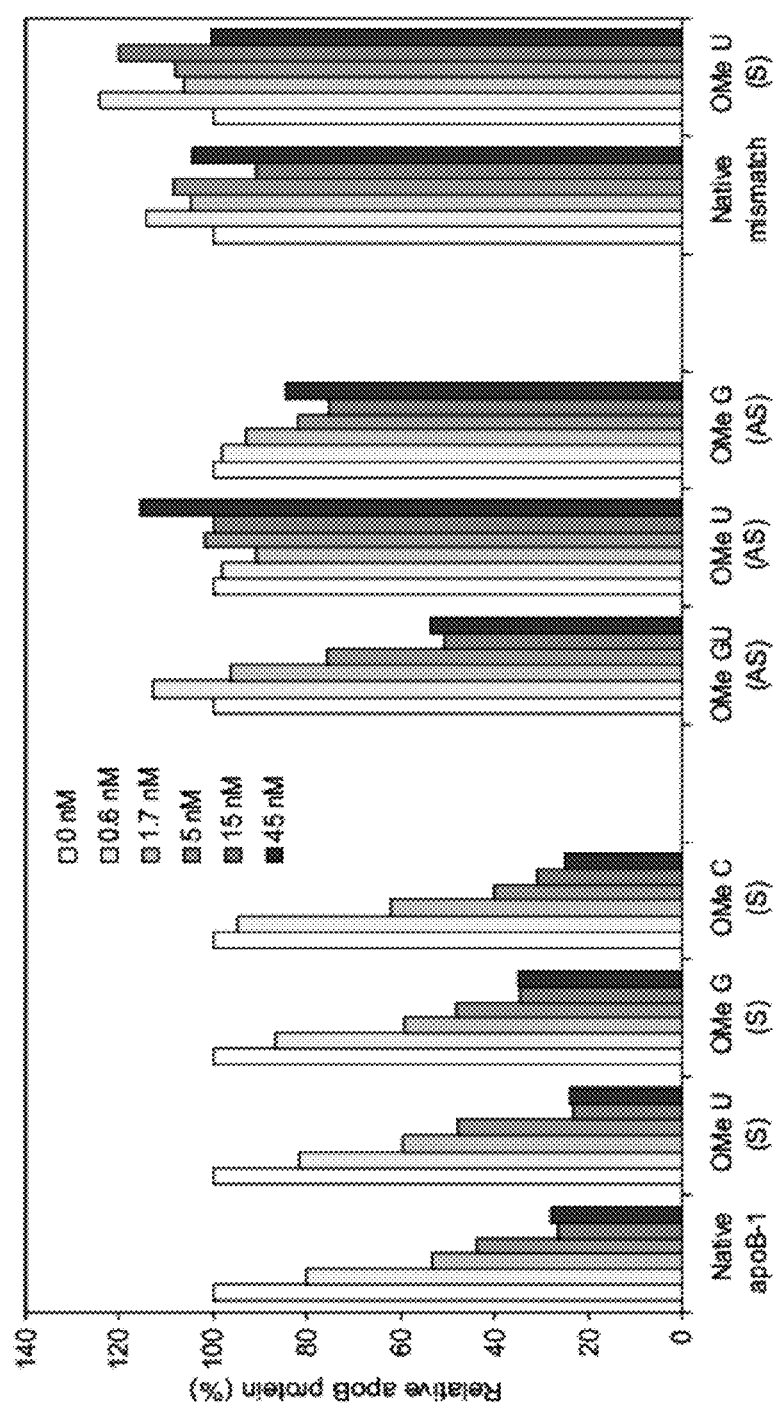
FIG. 8 illustrates data demonstrating in vitro silencing of ApoB expression by 2'OMe-modified siRNA. HepG2 cells were treated with encapsulated ApoB or mismatch siRNA at the indicated concentrations (0-45 nM). Unmodified (native) ApoB siRNA was compared to ApoB duplexes containing 2'OMe U, G, or C residues in the sense (S) or GU motif, U, or G residues in the antisense (AS) strands as indicated (see, Table 1 for modified siRNA sequences). Unmodified and 2'OMe U(S) ApoB mismatch siRNA served as control duplexes. ApoB protein in culture supernatants was measured by ELISA after 48 hours. ApoB levels are expressed as % of PBS-treated control cultures. Each value was derived from means of duplicate cultures and is representative of 3 separate experiments.

Restricting modifications to siRNA sense strand maintains RNAi activity. The gene silencing activity of native and 2'OMe-modified ApoB siRNAs was assessed in vitro. Unmodified ApoB encapsulated within liposomes caused potent, dose-dependent inhibition of ApoB protein in HepG2 cell culture supernatants (FIG. 8). Estimated $IC_{50}$ values (~1.5 nM) were in agreement with those established for this siRNA sequence using Oligofectamine transfection in a similar in vitro model (Soutschek et al., supra). Modified ApoB duplexes in which 2'OMe modifications were restricted to the non-targeting sense or passenger strand displayed ApoB silencing activity similar to that of the native siRNA (FIG. 8). In contrast, modifications to the targeting antisense (AS) or guide strand severely impacted the RNAi activity of the duplex. Incorporation of 2'OMe uridine or guanosine residues in the AS strand abrogated ApoB gene silencing, whereas the duplex containing the 5'-GUGUG-3' modified AS strand displayed substantially reduced activity (estimated $IC_{50}$=~15 nM) compared to the native or sense modified duplexes. Unmodified or modified ApoB mismatch control siRNAs yielded no significant inhibition of ApoB protein expression (FIG. 8). A similar strategy of restricting 2'OMe modifications to the sense strands of β-gal 728 and luciferase siRNA also proved successful in generating non-inflammatory siRNA that retained full RNAi activity (FIGS. 6-7). Although the negative impact of AS strand modification on gene silencing activity is consistent with previous work demonstrating that 2'OMe modification of the AS strand of an siRNA duplex, particularly at the 5' end, can reduce RNAi activity (Prakash et al., J. Med. Chem., 48:4247-4253 (2005)), siRNA sequences have been identified which can tolerate extensive 2'OMe modifications to the AS strand (Morrissey et al., Hepatology, 41:3149-1356 (2005); Czauderna et al., Nucl. Acids Res., 31:2705-2716 (2003)). These data illustrate that selective 2'OMe modifications, restricted to the sense strand of siRNA, offers a robust approach to overcoming the problem of immune activation by siRNA while reducing the chance of negatively impacting RNAi activity. These results indicate that this approach can be applied to many, if not all, siRNA sequences with inherent capacity to stimulate the innate immune response, encompassing the vast majority of conventionally designed synthetic siRNA.

Figure 9:
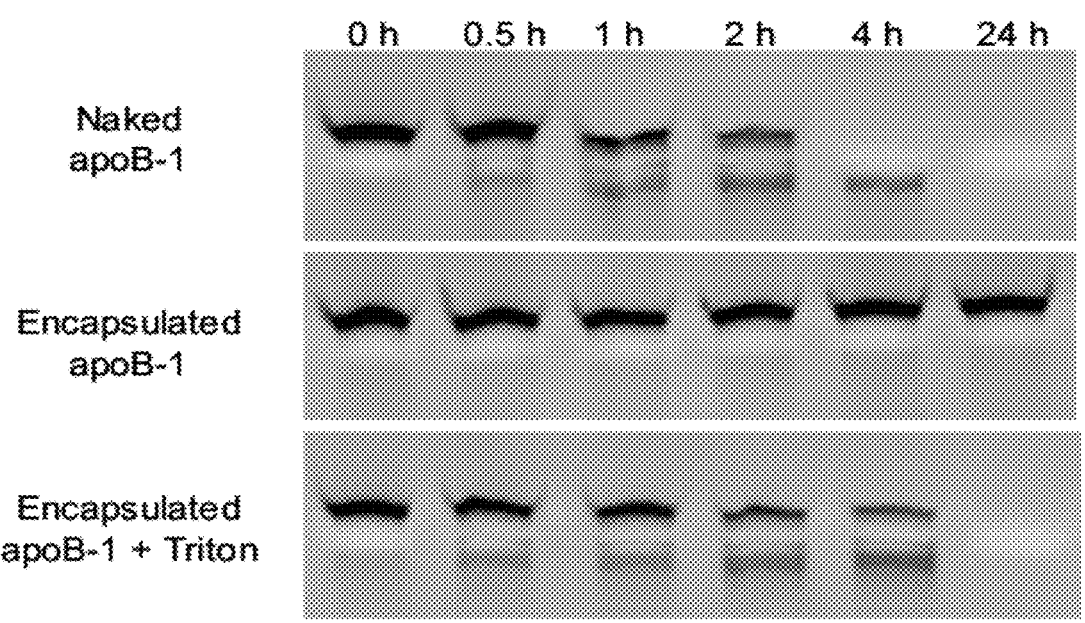
FIG. 9 illustrates data demonstrating that encapsulation of siRNA in lipid particles protects against serum nuclease degradation. Unmodified naked (top) or SNALP-encapsulated (middle) ApoB siRNA was incubated in 50% mouse serum at 37° C. Duplex integrity was assessed at indicated timepoints by non-denaturing PAGE analysis. Addition of Triton-X to disrupt lipid particle integrity (bottom) restored siRNA nuclease sensitivity.

Potent RNAi activity without immune stimulation in vivo. 2'OMe-modified ApoB siRNA were assessed for their ability to silence gene expression and immune stimulation in vivo. 2'OMe U(S) and GU(AS) modified ApoB were selected as non-inflammatory duplexes (see, FIGS. 3 and 4). This also afforded the opportunity to assess the impact of chemical modifications that reduced in vitro RNAi activity of the AS modified siRNA (see, FIG. 8). Native or 2'OMe-modified ApoB and mismatch siRNA were formulated in stable nucleic acid-lipid particles (SNALPs) previously shown to deliver siRNA to the liver (Morrissey et al., Nat. Biotechnol., 23:1002-1007 (2005)). For use in systemic applications, nucleic acid based drugs require stabilization or protection from nuclease degradation. Encapsulation inside the lipid bilayer protected unmodified and otherwise labile siRNA from serum nuclease degradation for greater than 24 hours at 37° C. in vitro, implying that encapsulation offers adequate nuclease protection without the need for extensive chemical modification to the siRNA. By comparison, naked siRNA was fully degraded within 4 hours under similar conditions (FIG. 9).

Figure 10A:
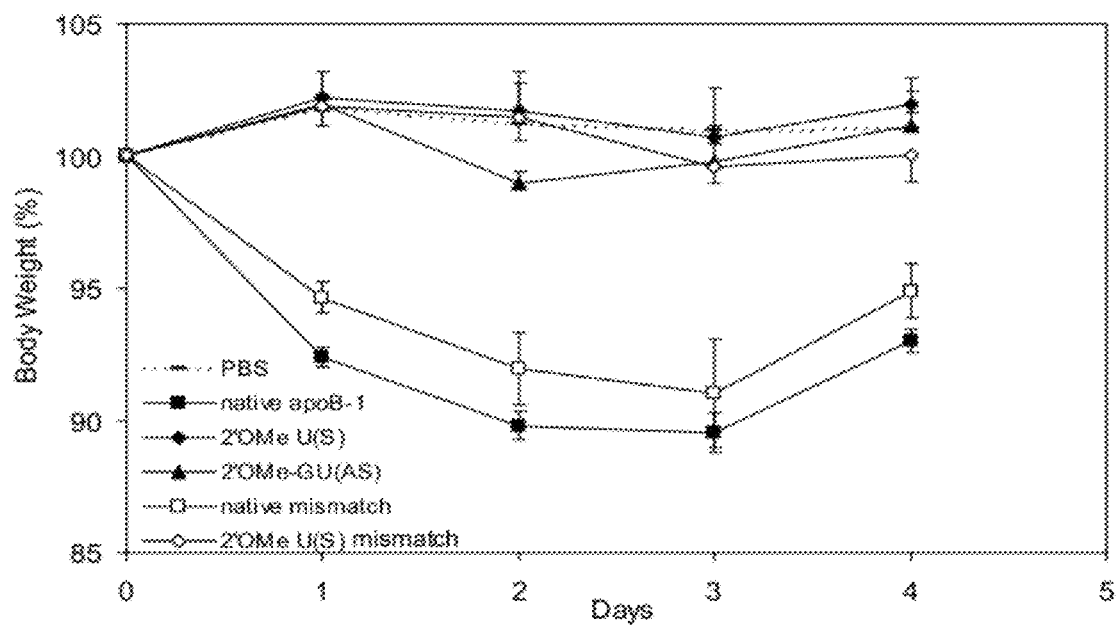
(FIG. 10A) Daily changes in body weight (% of day 0 weight) of ApoB (solid symbols) and mismatch (open symbols) siRNA treated mice over the 4-day study period.
Figure 10B:
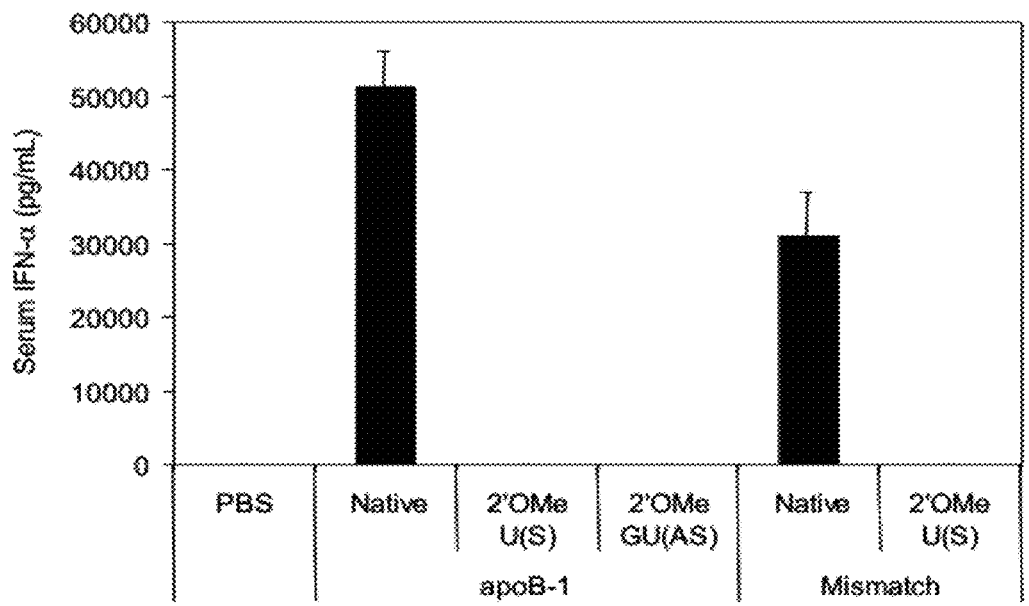
(FIG. 10B) Serum IFN-α from test bleeds 6 hours after initial treatment. ND=Not Detected; lower level of quantitation=75 pg/ml.

Encapsulated ApoB siRNA were administered intravenously to BALB/c mice at 5 mg/kg/day for 3 days. This regimen represents a 10-fold reduction in ApoB siRNA dose originally reported to be efficacious in experiments utilizing cholesterol-conjugated, chemically modified ApoB siRNA (Soutschek et al., supra). Animals receiving native, immunostimulatory ApoB or mismatch siRNA displayed overt symptoms of toxicity as evidenced by a loss of 10.5% and 9% of initial body weight respectively by day 3 (FIG. 10A) and mild deterioration in general body condition during the course of treatment. In contrast, treatment with the 2'OMe-modified siRNA was well tolerated with minimal (less than 1%) or no body weight loss (FIG. 10A). Abrogation of the innate cytokine response in these efficacy studies was confirmed by in-life serum IFN-α analysis (FIG. 10B), and accordingly the toxicity associated with administration of the unmodified siRNA was attributed to the systemic cytokine response. Of note, cytokine levels and body weight loss induced by unmodified mismatch siRNA were lower than for the corresponding active ApoB duplex. The mismatch control in this case was generated by four G/C substitutions within the ApoB sequence (Soutschek et al., supra), providing further evidence for the sequence-dependent effects on immune stimulation by RNA duplexes.

Figure 10C:
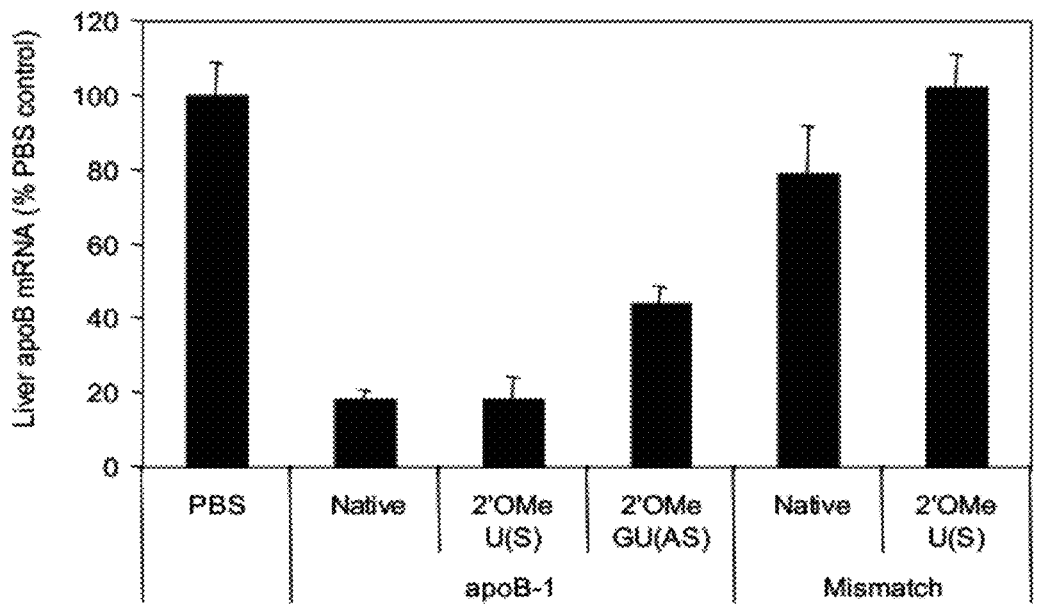
(FIG. 10C) ApoB mRNA levels in liver.

As a direct measure of RNAi-mediated knockdown, ApoB mRNA was determined in the liver two days after final siRNA treatment (FIG. 10C). In both the native and 2'OMe U(S) modified ApoB-treated groups, ApoB mRNA levels were significantly reduced compared to PBS-treated animals (18±2% and 18±5% of PBS controls, respectively). By comparison, mice treated with 2'OMe GU(AS) modified ApoB siRNA displayed less pronounced silencing of ApoB mRNA (44±4% of controls), correlating with reduced in vitro RNAi activity of this modified siRNA (see, FIG. 8). ApoB mRNA levels in the modified mismatch group were equivalent to those in PBS controls (FIG. 10C), while the native mismatch siRNA caused a modest reduction in ApoB mRNA levels (79±12% of PBS controls). The modest reduction in liver ApoB mRNA observed with the native mismatch siRNA was apparent in three separate experiments and correlated with interferon release and symptoms of toxicity associated with systemic administration and delivery of the unmodified siRNA.

Figure 10D:
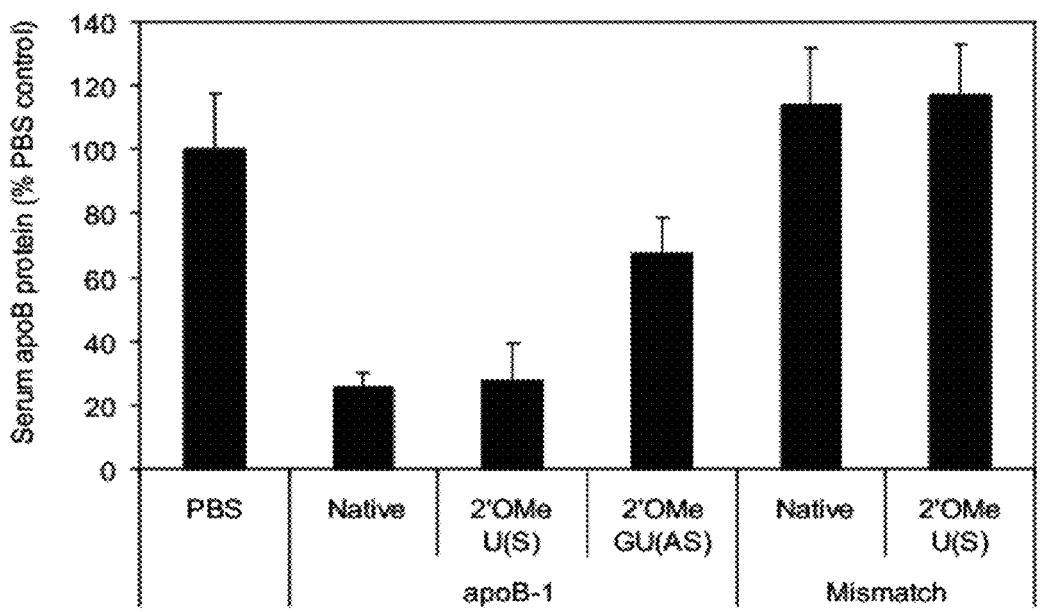
(FIG. 10D) ApoB protein in serum.
Figure 10E:
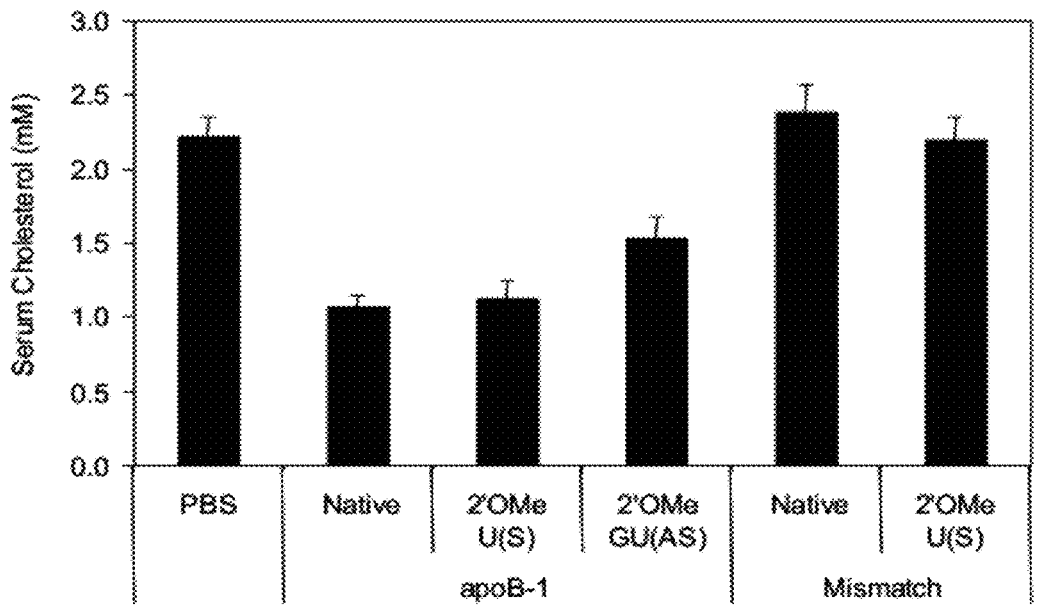
(FIG. 10E) Serum cholesterol (mM) 2 days after final siRNA treatment. ApoB levels are expressed as % of ApoB mRNA or ApoB protein compared to PBS-treated animals. All values are mean+SD of 5 animals. All data are representative of 2 separate experiments.

Silencing of ApoB mRNA in the liver resulted in proportional, sequence-specific reductions in serum ApoB protein. Mice treated with native, 2'OMe U(S), or GU(AS) modified ApoB siRNA had serum ApoB protein levels that were 26%, 28%, and 47% those of the PBS-treated animals, respectively (FIG. 10D). Functional silencing of ApoB expression was also reflected in significant reductions in serum cholesterol that correlated with the relative potency of mRNA and protein knockdown by the ApoB duplexes. Mice treated with native, 2'OMe U(S), or GU(AS) modified ApoB siRNA displayed serum cholesterol levels that were 48%, 51%, and 69% of cholesterol levels in the PBS control group (FIG. 10E). Neither mismatch siRNA had any effect on serum cholesterol (FIG. 10E). In separate experiments, the non-inflammatory 2'OMe G(S) modified ApoB siRNA mediated similar reductions in ApoB mRNA, protein, and serum cholesterol, in the absence of IFN induction.

Results from these studies demonstrate that lipid encapsulation of siRNA provides adequate serum stability for systemic applications and negates the need for extensive chemical modifications to the RNA. This, coupled with the effective delivery of the siRNA payload to the target organ, in this case the liver, facilitates the silencing of endogenous genes, exemplified in these studies by ApoB, a protein that represents a potential therapeutic target for hypercholesterolemia. Importantly, the 2'OMe-modified siRNA, designed to be non-inflammatory, displayed potency in vivo that is equivalent to the unmodified siRNA but without the immunotoxicity and other off-target effects associated with systemic administration of the unmodified siRNA. The approach described herein can be generally applicable to a wide range of gene targets and is suitable for use in a variety of therapeutic methods.

Discussion

Based on the finding that immune activation by siRNA is sequence-dependent, it has previously been shown to be possible to design active siRNA with negligible immunostimulatory activity by selecting sequences that lack GU-rich motifs (Judge et al., *Nat. Biotechnol.*, 23:457-462 (2005)). However, this strategy significantly limits the number of novel siRNA sequences that can be designed against a given target. Furthermore, it currently requires some degree of screening due to the relatively ill-defined nature of putative RNA immunostimulatory motifs. This study highlights a novel and robust approach to abrogate synthetic siRNA-mediated immune stimulation by selective incorporation of 2'OMe-modified nucleotides into the siRNA duplex. Remarkably, incorporation of as few as two 2'OMe guanosine or uridine residues in highly immunostimulatory siRNA molecules completely abrogated siRNA-mediated interferon and inflammatory cytokine induction in human PBMC and in mice in vivo. This degree of chemical modification represents ~5% of the native 2'-OH positions in the siRNA duplex. Since complete abrogation of the immune response required only one of the RNA strands to be selectively modified, 2'OMe modifications could be restricted to the sense strand of the duplex, therefore minimizing the potential for attenuating the potency of the siRNA. These findings have provided a simple rationale for the synthesis of non-immunostimulatory siRNA based on native sequences with proven RNAi activity. By combining selectively modified siRNA with an effective systemic delivery vehicle such as nucleic acid-lipid particles, potent silencing of an endogenous gene target can be achieved in vivo at therapeutically viable doses without the deleterious side-effects associated with systemic activation of the innate immune response.

Since the 2'-OH in the ribose backbone is a distinguishing feature of RNA, extensive chemical substitutions at this position would be anticipated to disrupt recognition of the modified nucleic acid by an RNA binding receptor pathway. However, this study unexpectedly shows that 2'OMe-modified siRNA are rendered non-immunostimulatory despite retaining up to 95% of their native ribonucleotides, including those comprising defined immunostimulatory regions of the RNA. 2'OMe is considered to be a relatively bulky chemical group at the 2' position that sits within the minor groove of an RNA duplex without significantly distorting its A-form helical structure (Chiu et al., *RNA*, 9:1034-1048 (2003); Cummins et al., *Nucl. Acids Res.*, 23:2019-2024 (1995)). This may be sufficient to disrupt interactions between the double-stranded RNA duplex and its putative immune receptor or accessory molecules. The trans-inhibitory effect of 2'-O-methylation, whereby 2'OMe-modified ssRNA annealed to unmodified immunostimulatory ssRNA generates a non-immunostimulatory duplex, is consistent with such a hypothesis that involves recognition of the siRNA as a double-stranded molecule.

A number of other stabilization chemistries are routinely used in synthetic siRNA design in an effort to confer nuclease resistance that may also influence immune recognition and RNAi. Locked nucleic acids (LNA) that contain a 2'-O, 4'-C methylene bridge in the sugar ring have been shown to partially reduce the immunostimulatory activity of an siRNA (Hornung et al., *Nat. Med.*, 11:263-270 (2005)). siRNA containing inverted deoxy abasic end caps have been found to retain immunostimulatory activity (Morrissey et al., *Nat. Biotechnol.*, 23:1002-1007 (2005)). No evidence of a trans-inhibitory effect was observed with LNA modified duplexes. These observations indicate that immune stimulation by siRNA is particularly sensitive to inhibition by 2'OMe modifications versus other, well characterized, stabilization chemistries.

This study demonstrates that both unmodified and 2'OMe-modified synthetic siRNA can mediate potent silencing of the endogenous gene target ApoB when encapsulated in lipid particles and administered systemically. Intravenous administration of encapsulated unmodified or modified ApoB siRNA resulted in significant reductions in ApoB mRNA levels in the liver and concomitant reductions in ApoB protein in the blood. Importantly, given the interest in ApoB as a therapeutic target for hypercholesterolemia, ApoB silencing resulted in a significant reduction in serum cholesterol. Lipid encapsulation confers excellent resistance to degradation by serum nucleases, enabling the in vivo use of minimally modified siRNA duplexes. By preventing the induction of interferons and inflammatory cytokines, the potential for non-specific effects on gene expression is limited while the tolerability of siRNA formulations is improved. Specifically, intravenous administration of encapsulated 2'OMe-modified siRNA is efficacious and well tolerated. These findings advance the use of synthetic siRNA in a broad range of in vivo and therapeutic applications.

Methods siRNA: All siRNA used in these studies were chemically synthesized by Dharmacon (Lafayette, Colo.) and received as desalted, deprotected polynucleotides. Duplexes were annealed by standard procedures. Complementary strands at equimolar concentrations were heated to 90° C. for 2 min and then cooled slowly at 37° C. for 60 min. Formation of annealed duplexes was confirmed by non-denaturing PAGE analysis. All native and 2'OMe-modified sequences used in this study are listed in Tables 1 and 2.

Lipid encapsulation of RNA: siRNA or ssRNA were encapsulated into liposomes by a process of spontaneous vesicle formation followed by stepwise ethanol dilution as described for pDNA by Jeffs et al., *Pharm. Res.*, 22:362-372 (2005). Liposomes were composed of the following lipids: synthetic cholesterol (Sigma; St. Louis, Mo.), the phospholipid DSPC (1,2-distearoyl-sn-glycero-3-phosphocholine; Avanti Polar Lipids; Alabaster, Ala.), the PEG-lipid PEG-cDMA (3-N-[(methoxy poly(ethylene glycol)2000)carbamoyl]-1,2-dimyrestyloxypropylamine), and the cationic lipid DLinDMA (1,2-dilinoleyloxy-3-(N,N-dimethyl)aminopropane) in the molar ratio 48:20:2:30. The lipids PEG-cDMA and DLinDMA (Heyes et al., *J. Control Release*, 107:276-287 (2005)) were synthesized at Protiva Biotherapeutics. The resulting stabilized lipid particles were dialyzed in PBS and filter sterilized through a 0.2 µm filter prior to use. Particle sizes of each liposome preparation ranged from 100-130 nm and typically contained 90-95% of siRNA encapsulated within the liposome. Concentration and percent encapsulation of formulated siRNA were determined using the membrane-impermeable fluorescent dye, RiboGreen® (Molecular Probes; Eugene, Oreg.) before and after the addition of detergent to disrupt the lipid bilayers (Jeffs et al., supra).

Serum nuclease protection assay: Unmodified naked or lipid-encapsulated siRNA (0.25 mg/ml) were incubated in 50% mouse serum at 37° C. At the times indicated, aliquots were taken directly into gel loading buffer containing 0.1% SDS and frozen in liquid nitrogen. After the final timepoint, siRNA samples were run on a non-denaturing 20% polyacrylamide TBE gel and visualized by ethidium bromide staining. To confirm that nuclease protection of siRNA was conferred by lipid encapsulation, 0.1% Triton-X100 was added to disrupt lipid bilayer integrity immediately prior to incubation with serum.

Cell isolation and culture: Human PBMC were isolated from whole blood from healthy donors by a standard Ficoll-Hypaque density centrifugation technique. For immune stimulation assays, $3 \times 10^5$ freshly isolated PBMC were seeded in triplicate in 96-well plates and cultured in RPMI 1640 medium with 10% FBS, 2 mM glutamine, 100 U/ml penicillin, and 100 µg/ml streptomycin. Liposome-encapsulated siRNA were added to cells at the indicated final nucleic acid concentration and culture supernatants were collected after 16-20 hours and assayed for IFN-α, IL-6, and TNF-α by sandwich ELISA.

In vitro RNA interference assay: HepG2 cells were seeded into 24-well plates at 20,000 cells/well. To determine in vitro RNAi activity of 2'OMe-modified ApoB siRNA, HepG2 cultures were treated, in triplicate, with encapsulated siRNA at nucleic acid concentrations between 0.6 nM and 45 nM. Media was changed 24 hours after addition of siRNA and then incubated for an additional 48 hours. Human ApoB protein levels were determined in culture supernatants by sandwich ELISA, as detailed in Soutschek et al., *Nature*, 432:173 (2004), using polyclonal goat anti-human ApoB capture antibody (Chemicon International) and horseradish peroxidase-conjugated goat anti-human ApoB-100 antibody (Academy Bio-medical) to detect bound ApoB. ELISA plates were developed using TMB substrate, stopped with 2N sulfuric acid, and absorbance read at 450 nm to 570 nm. $A_{450}$ values were normalized against a standard curve generated from untreated HepG2 conditioned media to define the linear range of the ELISA. Mean, residual ApoB protein levels in siRNA-treated culture supernatants were calculated as a percentage of PBS-treated controls.

In vivo cytokine induction: Animal studies were completed in accordance with the Canadian Council on Animal Care guidelines following approval by the local Animal Care and Use Committee at Protiva Biotherapeutics. 6-8 week old CD1 ICR mice (Harlan; Indianapolis, Ind.) were subjected to a three week quarantine and acclimation period prior to use. Encapsulated siRNA formulations were administered by standard intravenous injection in the lateral tail vein in 0.2 ml PBS. Blood was collected by cardiac puncture 6 hours after administration and processed as plasma for cytokine analysis. In RNAi efficacy experiments, plasma was collected from 50 µl test bleeds 6 hours after initial siRNA administration.

Cytokine ELISA: All cytokines were quantified using sandwich ELISA kits according to the manufacturer's instructions. These included mouse and human IFN-α (PBL Biomedical; Piscataway, N.J.), human IL-6 and TNF-α (eBioscience; San Diego, Calif.), and mouse IL-6, TNF-α, and IFN-γ (BD Biosciences; San Diego, Calif.).

In vivo RNA interference: Groups of 5 Balb/C mice were treated once a day for 3 consecutive days with lipid-encapsulated siRNA (native, 2'OMe U(S), 2'OMe, or GU(AS) ApoB and native or 2'OMe U(S) mismatch) at 5 mg/kg by standard intravenous injection via the lateral tail vein. Body weights and general observations were recorded throughout the duration of the studies. 48 hours after the final siRNA treatment, mice were sacrificed. Blood was collected by cardiac puncture for serum analysis of ApoB protein and cholesterol. Livers were weighed and collected into 6 ml RNALater (Sigma) for ApoB mRNA analysis by QuantiGene assay (Genospectra; Fremont, Calif.).

Serum cholesterol was measured using a commercial cholesterol detection kit according to the manufacturer's instructions (Thermo electron Corp; Melbourne, Australia). ApoB-100 was detected in serum from individual animals by sandwich ELISA using monoclonal mouse ApoB-100 capture antibody LF3 (Zlot et al., *J. Lipid Res.*, 40:76-84 (1999)). Bound ApoB-100 was detected with polyclonal rabbit anti-mouse ApoB (Biodesign International; Saco, Me.) and horseradish peroxidase-conjugated goat anti-rabbit Ig's (Jackson Immunoresearch; West Grove, Pa.). Serum ApoB levels were determined from $A_{450}$ values using a standard curve generated with normal mouse serum to define the linear range of the ELISA and expressed as a percentage of the PBS-treated control group.

The QuantiGene assay (Genospectra) was used to quantify the reduction of mouse ApoB mRNA in liver tissue after siRNA treatment. Small uniform tissue samples were taken from livers that had been collected 48 hours after final injection and stored in RNAlater (Sigma). Lysates were directly used for ApoB and GAPDH mRNA quantification, and the ratio of ApoB and GAPDH mRNA was calculated and expressed as a group average relative to the PBS control group. Specific probe sets used for detection of mRNA were designed by Genospectra to target the following regions: for the ApoB mRNA, positions 5183-5811 of accession XM_137955; for GAPDH mRNA, positions 9-319 of accession NM_008084.

Example 2

Design of ApoB siRNA with Selective Chemical Modifications

This example illustrates that minimal 2'OMe modifications at selective positions in the sense and antisense strands of the ApoB siRNA duplex are sufficient to decrease the immunostimulatory properties of ApoB siRNA while retaining RNAi activity. In particular, selective 2'OMe-uridine and/or 2'OMe-guanosine modifications at less than about 30% of the nucleotide positions in both strands provide ApoB siRNA with a desirable combination of silencing and non-immunostimulatory properties.

Results

A female BALB/c mouse model was used to determine the efficacy and toxicity profiles of SNALP formulations comprising ApoB siRNA with selective chemical modifications in the sense and antisense strands. The ApoB siRNA duplexes used in this study are provided in Table 3.

TABLE 3 siRNA duplexes comprising sense and antisense ApoB RNA polynucleotides.

| Position | Modification | ApoB siRNA sequence | SEQ ID NO: | % 2'OMe-Modified | % Modified in DS Region |
|---|---|---|---|---|---|
| 10048 | 0/0 | 5'-AGUGUCAUCACACUGAAUACC-3' | 46 | 0/42 = 0% | 0/38 = 0% |
| | | 3'-GUUCACAGUAGUGUGACUUAU-5' | 47 | | |
| 10048 | U2/4 G1/0 | 5'-AGUGUCAUCACACU<u>G</u>AAUACC-3' | 48 | 7/42 = 16.7% | 7/38 = 18.4% |
| | | 3'-GUUCACAGUAGUGUGACUUAU-5' | 49 | | |
| 10048 | U2/2 G1/2 | 5'-AGUGUCAUCACACUGAAUACC-3' | 50 | 7/42 = 16.7% | 7/38 = 18.4% |
| | | 3'-GUUCACAGUAGUGUGACUUAU-5' | 51 | | |
| 10048 | U5/3 | 5'-AGUGUCAUCACACUGAAUACC-3' | 52 | 8/42 = 19% | 8/38 = 21% |
| | | 3'-GUUCACAGUTGUGUGACUUAU-5' | 53 | | |
| 10048 | U5/5 | 5'-AGUGUCAUCACACUGAAUACC-3' | 52 | 10/42 = 23.8% | 10/38 = 26.3% |
| | | 3'-GUUCACAGUAGUGUGACUUAU-5' | 54 | | |
| 10048 | U2/2 G3/3 | 5'-AGUGUCAUCACACU<u>G</u>AAUACC-3' | 55 | 10/42 = 23.8% | 10/38 = 26.3% |
| | | 3'-GUUCACAGUAGUGUGACUUAU-5' | 56 | | |
| 10048 | U5/4 G2/4 | 5'-AGUGUCAUCACACUGAAUACC-3' | 57 | 15/42 = 35.7% | 15/38 = 39.5% |
| | | 3'-GUUCACAGUAGUGUGACUUAU-5' | 58 | | |
| 10048 | U5/7 G1/2 | 5'-AGUGUCAUCACACUGAAUACC-3' | 59 | 15/42 = 35.7% | 15/38 = 39.5% |
| | | 3'-GUUCACAGUAGUGUGACUUAU-5' | 60 | | |
| 10086 | 0/0 | 5'-ACACUAAGAACCAGAAGAUCA-3' | 61 | 0/42 = 0% | 0/38 = 0% |
| | | 3'-AUUGUGAUUCUUGGUCUUCUA-5' | 62 | | |
| 10086 | U1/3 G2/1 | 5'-ACACUAAGAACCAGAAGAUCA-3' | 63 | 7/42 = 16.7% | 7/38 = 18.4% |
| | | 3'-AUUGUGAUUCUUGGUCUUCUA-5' | 64 | | |
| 10346 | 0/0 | 5'-AUGGAAAUACCAAGUCAAAAC-3' | 65 | 0/42 = 0% | 0/38 = 0% |
| | | 3'-AUUACCUUUAUGGUUCAGUUU-5' | 66 | | |
| 10346 | U3/4 | 5'-AUGGAAAUACCAAGUCAAAAC-3' | 67 | 7/42 = 16.7% | 7/38 = 18.4% |
| | | 3'-AUUACCUUUAUGGUUCAGUUU-5' | 68 | | |

Column 1: The number refers to the nucleotide position of the 5' base of the sense strand relative to the mouse ApoB mRNA sequence XM_137955.
Column 2: The numbers refer to the distribution of 2'OMe chemical modifications in each strand. For example, "U2/4" indicates 2 uridine 2'OMe modifications in the sense strand and 4 uridine 2'OMe modifications in the antisense strand.
Column 3: 2'OMe-modified nucleotides are indicated in bold and underlined.
Column 4: The number and percentage of 2'OMe-modified nucleotides in the siRNA duplex are provided.
Column 5: The number and percentage of modified nucleotides in the double-stranded (DS) region of the siRNA duplex are provided.

Figure 11:
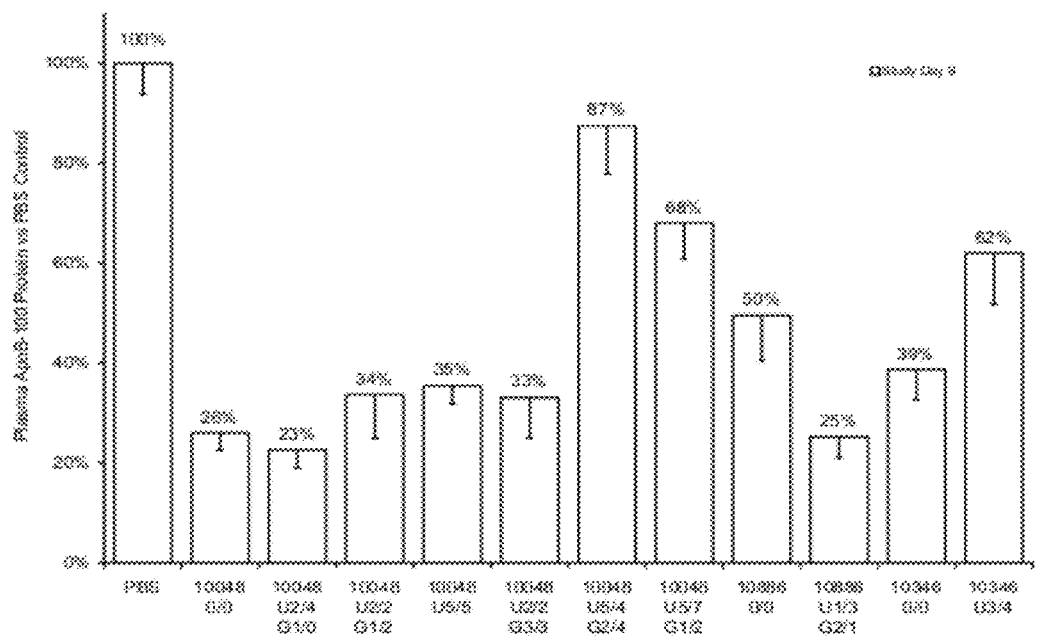
FIG. 11 illustrates data demonstrating the silencing activity of various unmodified and chemically modified ApoB siRNA. SNALP-formulated siRNA silencing potency was measured 7 days after the end of an IV treatment at a daily siRNA dosage of 2 mg/kg for three consecutive days. ApoB silencing activity was measured in terms of a reduction in plasma ApoB-100 protein levels compared to a PBS-treated control. Each bar represents the group mean (n=5)±standard deviation (SD).

For the ApoB 10048 siRNA family of sequences, 2'OMe modifications at 16.7% or 23.8% of the nucleotide positions in the siRNA duplex produced similar silencing activity as the unmodified siRNA (FIG. 11, lanes 2-6). Similar results were obtained for the ApoB 10048 siRNA sequence with 2'OMe modifications at 19% of the nucleotide positions. However, 2'OMe modifications at 35.7% of the nucleotide positions in the siRNA duplex resulted in reduced activity (FIG. 11, lanes 7-8). For the ApoB 10886 siRNA sequences, 2'OMe modifications at 16.7% of the nucleotide positions in the siRNA duplex caused increased activity as compared to the unmodified siRNA (FIG. 11, lanes 9-10). For the ApoB 10346 siRNA sequences, 2'OMe modifications at 16.7% of the nucleotide positions in the siRNA duplex caused decreased activity as compared to the unmodified siRNA (FIG. 11, lanes 11-12).

Figure 12:
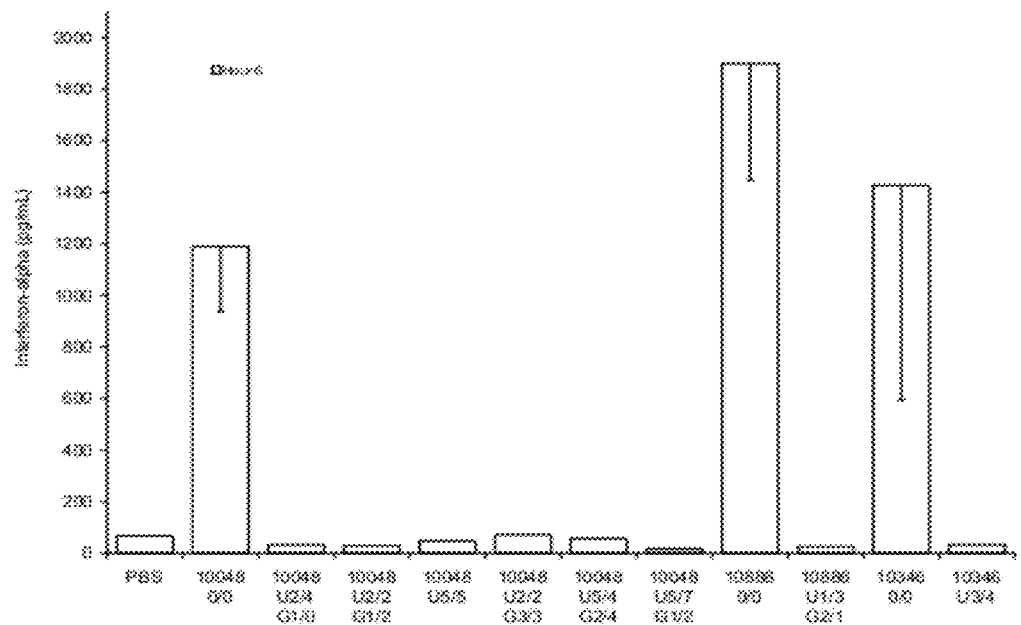
FIG. 12 illustrates data demonstrating the immunostimulatory properties of various unmodified and chemically modified ApoB siRNA. The immunostimulatory property of each siRNA, as characterized by cytokine release, was measured 6 hours after the initial IV dose of SNALP-formulated siRNA. Plasma concentrations of the cytokine interferon-alpha were measured using ELISA. For treatments causing a significant response (values over 200 pg/mL), plasma samples were diluted 10-fold and each animal was analyzed separately such that the bar in the figure represents the group mean (n=5) ±standard deviation (SD). For treatments causing very little response (values under 200 pg/mL), samples were pooled and assayed at a 4-fold dilution.

Chemical modification of siRNA using 2'OMe substitutions improved the toxicity profile of in vivo siRNA treatment by abrogating the cytokine response. As shown in FIG. 12, none the modified ApoB siRNA tested in this panel stimulated the release of interferon-alpha, whereas treatment with any of the three unmodified siRNA counterparts resulted in considerable concentrations of interferon-alpha in plasma at Hour 6.

siRNA sense strand corresponds to nucleotides 10164-10184 of human ApoB mRNA sequence NM_000384. The ApoB 10886 siRNA sense strand corresponds to nucleotides 11002-11022 of human ApoB mRNA sequence NM_000384. The ApoB 10346 siRNA sense strand corresponds to nucleotides 10462-10482 of human ApoB mRNA sequence NM_000384.

Lipid encapsulation of RNA: A "2:40:10" DSPC:cholesterol:PEG-C-DMA:DLinDMA (10:48:2:40 molar ratio) SNALP formulation was prepared using a direct dilution process at a targeted nucleic acid to lipid ratio of 0.04.

In vivo treatment regime: BALB/c mice (female, 4 weeks old) were obtained from Harlan Labs. After an acclimation period of at least 7 days, animals were administered the SNALP formulations shown in Table 4 by intravenous (IV) injection in the lateral tail vein once daily on Study Days 0, 1, and 2 (3 doses total per animal). Dosage was 2 mg siRNA per kg body weight, corresponding to 10 ml/kg (rounded to the nearest 10 µl). As a negative control, one group of animals was given an IV injection of PBS vehicle. Body weights and cage-side observations of animal behavior and/or appearance were recorded on Study Days 0-3, 9, and 16. Tails nicks were performed to collect small amounts (50 µl) of whole blood which was processed for plasma. On Study Day 16, animals were euthanized with a lethal dose of ketamine/xylazine and blood was collected via cardiac puncture prior to cervical dislocation. Blood was collected in a lavendar EDTA microtainer and processed for plasma.

TABLE 4

The in vivo treatment regime and SNALP formulations used in this study.

| Group | # Mice | Test Article | | Day 0, 1, 2 IV Dose | Sample Collections |
|---|---|---|---|---|---|
| 1 | 5 | PBS vehicle pH 7.4 | | 10 ml/kg | Hour 6, Day 9 |
| 2 | female | 2:40:10 | 10048 0/0 | 3 daily | tail nicks; |
| 3 | BALB/c | SNALP | 10048 U2/4 G1/0 | doses at | Day 16 |
| 4 | 5-6 wk | | 10048 U2/2 G1/2 | 2 mg/kg | sacrifice |
| 5 | | | 10048 U5/5 | each | |
| 6 | | | 10048 U2/2 G3/3 | | |
| 7 | | | 10048 U5/4 G2/4 | | |
| 8 | | | 10048 U5/7 G1/2 | | |
| 9 | | | 10886 0/0 | | |
| 10 | | | 10886 U1/3 G2/1 | | |
| 11 | | | 10346 0/0 | | |
| 12 | | | 10346 U3/4 | | |

Discussion

This example demonstrates that SNALP-formulated ApoB-targeting siRNA comprising minimal 2'OMe modifications at selective positions within the sense and antisense strands are capable of silencing up to 77% plasma ApoB protein levels relative to a PBS control at an extended timepoint of seven days post IV treatment. In fact, selective 2'OMe-uridine and/or 2'OMe-guanosine modifications at less than about 30% (e.g., 16.7%, 19%, or 23.8%) of the nucleotide positions of both strands of the siRNA duplex typically produced similar silencing activity as the unmodified siRNA sequence. In addition, such 2'OMe modifications improved the toxicity profile of in vivo treatment by decreasing the immunostimulatory properties of ApoB siRNA.

Methods siRNA: siRNA duplexes were prepared by annealing two deprotected and desalted RNA polynucleotides. Each polynucleotide was designed to be 21 bases in length and each duplex was designed to contain a 19-base double-stranded region with two 3' overhangs on each side of the double-stranded region. All duplexes were designed to be cross-reactive against mouse and human ApoB. The ApoB 10048

Analysis methods. ApoB protein levels in plasma were measured using an ELISA method essentially as described in Zlot et al., *J. Lipid Res.*, 40:76-84 (1999). Interferon-α levels in plasma were measured using a sandwich ELISA method according to the manufacturer's instructions (PBL Biomedical; Piscataway, N.J.).

Example 3

Design of Eg5 siRNA with Selective Chemical Modifications

This example illustrates that minimal 2'OMe modifications at selective positions in the sense and/or antisense strands of the Eg5 siRNA duplex are sufficient to decrease the immunostimulatory properties of Eg5 siRNA while retaining RNAi activity. In particular, selective 2'OMe-uridine and/or 2'OMe-guanosine modifications at less than about 20% of the nucleotide positions in one or both strands provide Eg5 siRNA with a desirable combination of silencing and non-immunostimulatory properties.

Results

Figure 13:
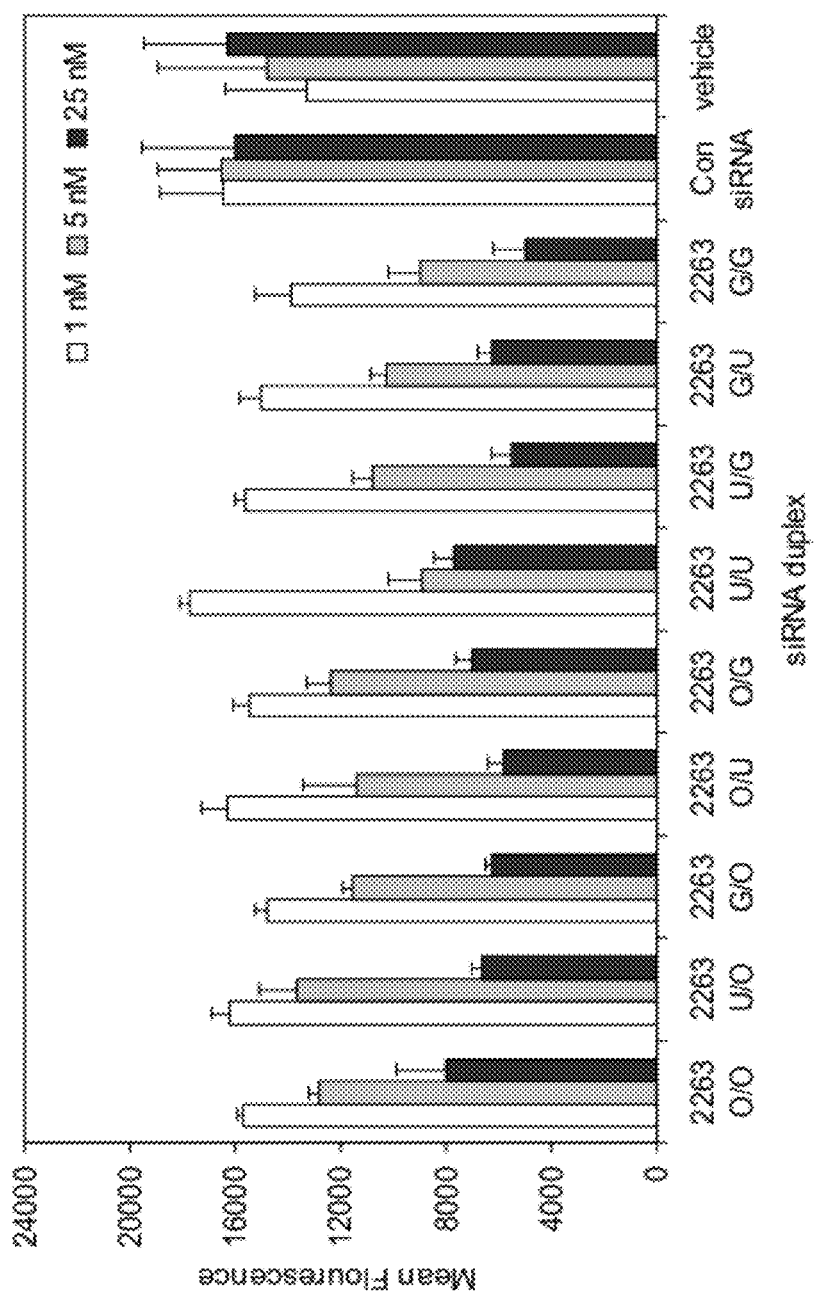
FIG. 13 illustrates data demonstrating that selective 2'OMe modifications to Eg5 2263 siRNA retains RNAi activity in human HeLa cells.
Figure 14:
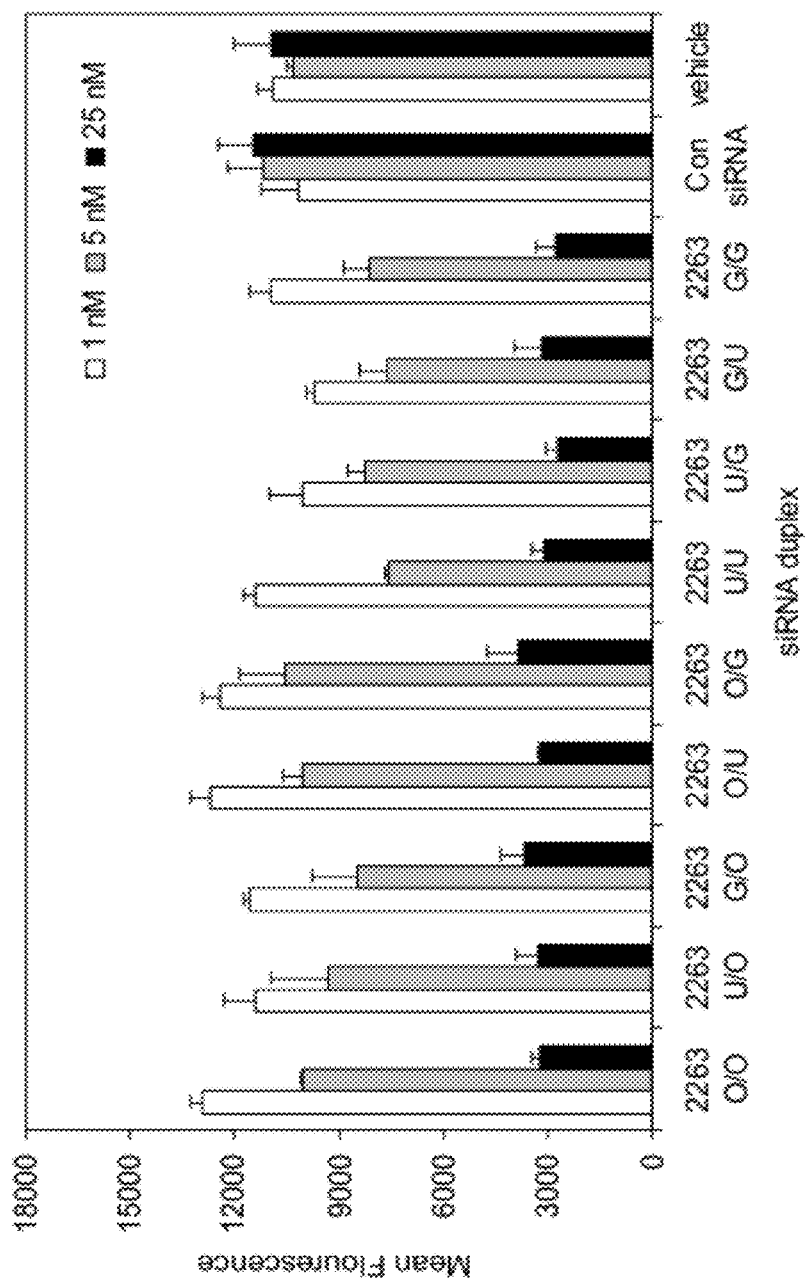
FIG. 14 illustrates data demonstrating that selective 2'OMe modifications to Eg5 2263 siRNA retains RNAi activity in mouse Neuro2A cells.
Figure 15:
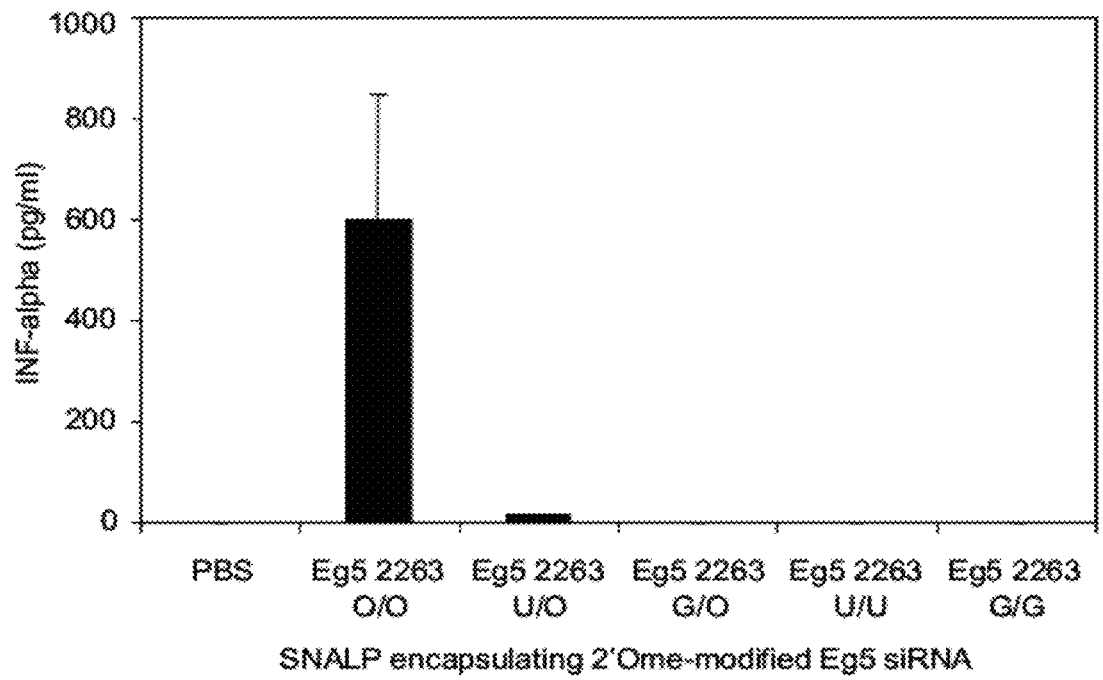
FIG. 15 illustrates data demonstrating the selective 2'OMe modifications to Eg5 2263 siRNA abrogates the interferon induction associated with systemic administration of the native duplex.

Selective modifications to Eg5 siRNA retain anti-proliferative activity. A panel of 2'OMe-modified Eg5 siRNA molecules was prepared and their RNAi activity evaluated in human HeLa cells and mouse Neuro2A cells. The Eg5 siRNA duplexes used in this study are provided in Table 5. The modifications involved introducing 2'OMe-uridine and/or 2'OMe-guanosine at selected positions in the sense and/or antisense strand of the Eg5 2263 siRNA sequence, in which the siRNA duplex contained less than about 20% 2'OMe-modified nucleotides. Anti-proliferative activity was evaluated in a cell viability bioassay. In particular, cell viability of cell cultures was measured 48 hours after treatment with SNALP formulations comprising Eg5 2263 siRNA and was expressed as mean fluorescence units. FIG. 13 shows that selective chemical modifications to the Eg5 2263 siRNA duplex retained RNAi activity in human HeLa cells. Similarly, FIG. 14 shows that selective chemical modifications to the Eg5 2263 siRNA duplex retained RNAi activity in mouse Neuro2A cells.

immune response, e.g., cytokine induction. BALB/c mice (n=3 per treatment group) were injected with 40 µg of the SNALP formulation comprising Eg5 2263 siRNA. Samples were collected 6 hours post-treatment and tested for interferon-α levels by an ELISA assay. FIG. 15 shows that selective 2'OMe modifications to Eg5 2263 siRNA abrogated the interferon induction associated with systemic administration of the native (i.e., unmodified) duplex.

Selective modifications to Eg5 siRNA abrogate the antibody response against the delivery vehicle. Unmodified Eg5 2263 siRNA (i.e., 0/0) and certain 2'OMe-modified variants thereof (i.e., U/O and U/U) were encapsulated into SNALPs having 2 mol % PEG-cDMA, 40 mol % DLinDMA, 10 mol % DSPC, and 48 mol % cholesterol. These SNALP-formulated Eg5-targeting siRNA were tested in vivo in mice to look for the induction of an immune response against components of the delivery vehicle such as PEG. In particular, mice (n=4)

TABLE 5 siRNA duplexes comprising sense and antisense Eg5 RNA polynucleotides.

| Modification | Eg5 2263 siRNA sequence | SEC. ID NO: | % 2'OMe-Modified | % Modified in DS Region |
|---|---|---|---|---|
| 0/0 | 5'-CUGAAGACCUGAAGACAAUdTdT-3' | 69 | 0/42 = 0% | 0/38 = 0% |
| | 3'-dTdTGACUUCUGGACUUCUGUUA-5' | 70 | | |
| U/0 | 5'-CU<u>G</u>AAGACCU<u>G</u>AAGACAA<u>U</u>dTdT-3' | 71 | 3/42 = 7.1% | 3/38 = 7.9% |
| | 3'-dTdTGACUUCUGGACUUCUGUUA-5' | 70 | | |
| G/0 | 5'-CU<u>G</u>AA<u>G</u>ACCU<u>G</u>AA<u>G</u>ACAAUdTdT-3' | 72 | 4/42 = 9.5% | 4/38 = 10.5% |
| | 3'-dTdTGACUUCUGGACUUCUGUUA-5' | 70 | | |
| 0/U | 5'-CUGAAGACCUGAAGACAAUdTdT-3' | 69 | 3/42 = 7.1% | 3/38 = 7.9% |
| | 3'-dTdTGAC<u>U</u>UC<u>U</u>GGAC<u>UU</u>CUGUUA-5' | 73 | | |
| 0/G | 5'-CUGAAGACCUGAAGACAAUdTdT-3' | 69 | 3/42 = 7.1% | 3/38 = 7.9% |
| | 3'-dTdT<u>G</u>ACUUCU<u>GG</u>ACUUCU<u>G</u>UUA-5' | 74 | | |
| U/U | 5'-CU<u>G</u>AAGACCU<u>G</u>AAGACAA<u>U</u>dTdT-3' | 71 | 6/42 = 14.3% | 6/38 = 15.8% |
| | 3'-dTdTGAC<u>U</u>UC<u>U</u>GGAC<u>UU</u>CUGUUA-5' | 73 | | |
| U/G | 5'-CU<u>G</u>AAGACCU<u>G</u>AAGACAA<u>U</u>dTdT-3' | 71 | 6/42 = 14.3% | 6/38 = 15.8% |
| | 3'-dTdT<u>G</u>ACUUCU<u>GG</u>ACUUCU<u>G</u>UUA-5' | 74 | | |
| G/G | 5'-CU<u>G</u>AA<u>G</u>ACCU<u>G</u>AA<u>G</u>ACAAUdTdT-3' | 72 | 7/42 = 16.7% | 7/38 = 18.4% |
| | 3'-dTdT<u>G</u>ACUUCU<u>GG</u>ACUUCU<u>G</u>UUA-5' | 74 | | |
| G/U | 5'-CU<u>G</u>AA<u>G</u>ACCU<u>G</u>AA<u>G</u>ACAAUdTdT-3' | 72 | 7/42 = 16.7% | 7/38 = 18.4% |
| | 3'-dTdTGAC<u>U</u>UC<u>U</u>GGAC<u>UU</u>CUGUUA-5' | 73 | | |

Column 1: "0/0" = Unmodified siRNA duplex; "U/0" = 2'OMe-uridine modified sense strand (SS); "G/0" = 2'OMe-guanosine modified SS; "0/U" = 2'OMe-uridine modified antisense strand (AS); "0/G" = 2'OMe-guanosine modified AS; "U/U" = 2'OMe-uridine modified siRNA duplex; "U/G" = 2'OMe-uridine modified SS and 2'OMe-guanosine modified AS; "G/G" = 2'OMe-guanosine modified siRNA duplex; and "G/U" = 2'OMe-guanosine modified SS and 2'OMe-uridine modified AS.
Column 2: 2'OMe-modified nucleotides are indicated in bold and underlined;, "dT" = deoxythymidine.
Column 3: The number and percentage of 2'OMe-modified nucleotides in the siRNA duplex are provided.
Column 4: The number and percentage of modified nucleotides in the double-stranded (DS) region of the siRNA duplex are provided.

Figure 16:
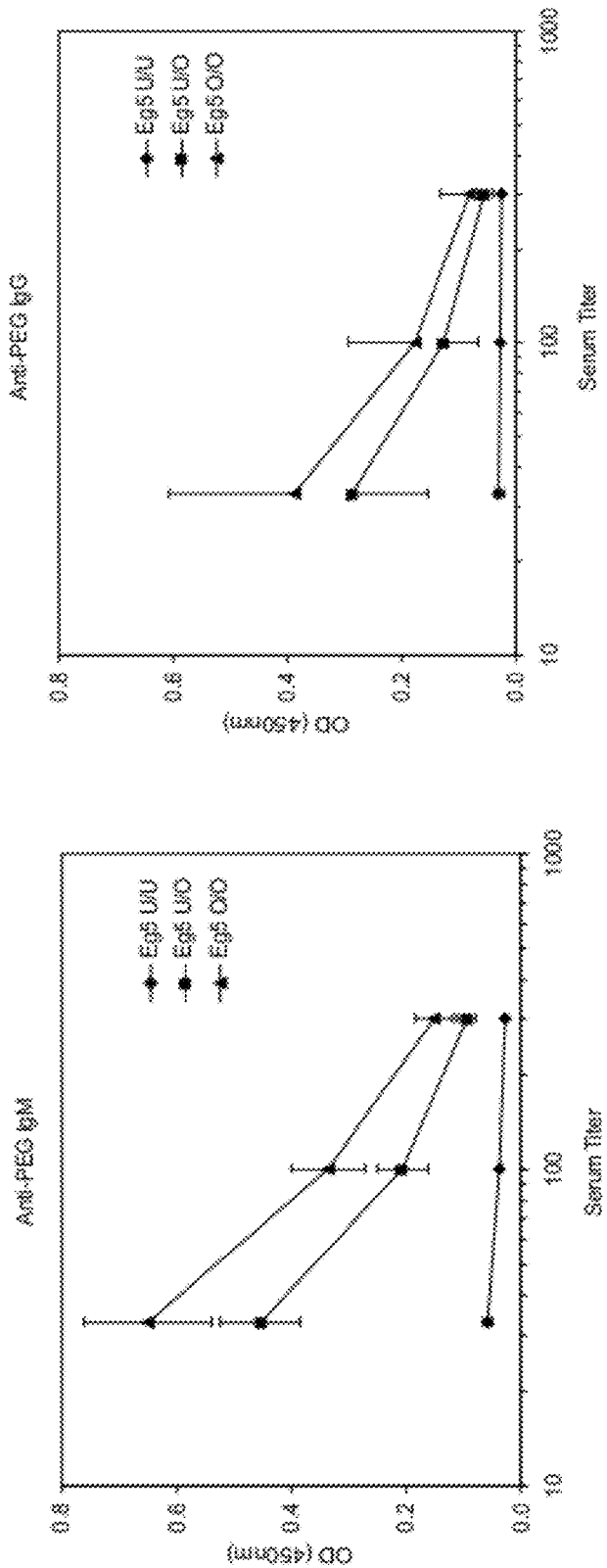
FIG. 16 illustrates data demonstrating that selective 2'OMe modifications to both strands of Eg5 2263 siRNA is required to fully abrogate the antibody response against the PEG component of the SNALP delivery vehicle.

Selective modifications to Eg5 siRNA abrogate in vivo cytokine induction. Unmodified Eg5 2263 siRNA (i.e., 0/0) and certain 2'OMe-modified variants thereof (i.e., U/O, G/0, U/U, and G/G) were encapsulated into SNALPs having 2 mol % PEG-cDMA, 40 mol % DLinDMA, 10 mol % DSPC, and 48 mol % cholesterol. These SNALP-formulated Eg5-targeting siRNA were tested in vivo to look for the induction of an were treated 3×2 mg/kg daily with the SNALP formulation comprising Eg5 2263 siRNA and serum levels of anti-PEG IgM and IgG antibodies were assayed on day 10. FIG. 16 shows that selective 2'OMe modifications to both strands of the Eg5 2263 siRNA duplex (i.e., U/U) was required to fully abrogate the antibody response against the PEG component of the SNALP delivery vehicle associated with systemic administration of the native (i.e., unmodified) duplex.

Methods siRNA: All siRNA used in these studies were chemically synthesized by Protiva Biotherapeutics (Burnaby, BC), University of Calgary (Calgary, AB), or Dharmacon Inc. (Lafayette, Colo.). siRNA were desalted and annealed using standard procedures. The Eg5 2263 siRNA sense strand corresponds to nucleotides 2263-2281 of human Eg5 mRNA sequence NM_004523.

Lipid encapsulation of siRNA: Unless otherwise indicated, siRNAs were encapsulated into liposomes composed of the following lipids; synthetic cholesterol (Sigma; St. Louis, Mo.), the phospholipid DSPC (1,2-distearoyl-sn-glycero-3-phosphocholine; Avanti Polar Lipids; Alabaster, Ala.), the PEG-lipid PEG-cDMA (3-N-[(-Methoxy poly(ethylene glycol)2000)carbamoyl]-1,2-dimyrestyloxy-propylamine), and the cationic lipid DLinDMA (1,2-Dilinoleyloxy-3-(N,N-dimethyl)aminopropane) in the molar ratio 48:10:2:40. In other words, unless otherwise indicated, siRNAs were encapsulated into liposomes of the following SNALP formulation: 2 mol % PEG-cDMA, 40 mol % DLinDMA, 10 mol % DSPC, and 48 mol % cholesterol. For vehicle controls, empty liposomes with identical lipid composition were formed in the absence of siRNA.

In vivo cytokine induction: Animal studies were completed in accordance with the Canadian Council on Animal Care guidelines following approval by the local Animal Care and Use Committee at Protiva Biotherapeutics. 6-8 week old CD1 ICR mice (Harlan; Indianapolis, Ind.) were subjected to a three week quarantine and acclimation period prior to use. Encapsulated siRNA formulations were administered by standard intravenous injection in the lateral tail vein in 0.2 ml PBS. Blood was collected by cardiac puncture 6 h after administration and processed as plasma for cytokine analysis. In RNAi efficacy experiments, plasma was collected from 50 µl test bleeds 6 h after initial siRNA administration. Interferon-α levels in plasma were measured using a sandwich ELISA method according to the manufacturer's instructions (PBL Biomedical; Piscataway, N.J.).

Cell viability assay: Cell viability of in vitro cell cultures was assessed using the commercial reagent CellTiter-Blue™ (Promega Corp.; Madison, Wis.), a resazurin dye that is reduced by metabolically active cells to the fluorogenic product resorufin. Various cancer cell lines were cultured in vitro using standard tissue culture techniques. 48-72 hours after treatment with siRNA formulations or small molecule drugs, CellTiter-Blue™ reagent was added to the culture to quantify the metabolic activity of the cells, a measure of cell viability.

Antibody assay: An ELISA was developed to detect IgM and IgG antibodies against the PEG-lipid and other lipid components of SNALP. Briefly, 10 µg of PEG-cDSA was added in 20 µl 100% ethanol to 96 well plates containing PVDF membranes (Millipore Corp.; Bedford, Mass.). PEG-cDSA-coated membranes were allowed to completely air dry for 2 hours before blocking for 1 hour with 10% FBS in PBS. 100 µl of serially diluted serum samples in blocking buffer was then applied in duplicate wells for 1 hour and washed 4 times with 1% FBS in PBS. Plate-bound antibodies were detected with HRP-conjugated goat anti-IgM Fcµ or IgG Fcγ. Bound enzyme was developed with TMB substrate, stopped with 2 N sulfuric acid, and then read in a spectrophotometer at 450 nm to 570 nm.

Example 4

Design of Anti-Influenza siRNA with Selective Chemical Modifications

This example illustrates that minimal 2'OMe modifications at selective positions in the sense strand of the influenza nucleocapsid protein (NP) siRNA duplex are sufficient to decrease the immunostimulatory properties of NP siRNA while retaining RNAi activity. In particular, selective 2'OMe-uridine modifications at less than about 20% of the nucleotide positions in the sense strand provide NP siRNA with a desirable combination of silencing and non-immunostimulatory properties.

Results

Selective modifications to NP siRNA retain viral knockdown activity. A panel of 2'OMe-modified NP siRNA was prepared and their RNAi activity evaluated in Madin-Darby Canine Kidney (MDCK) cells. The NP siRNA duplexes used in this study are provided in Table 6. The modifications involved introducing 2'OMe-uridine at selected positions in the sense strand of the NP siRNA sequence, in which the siRNA duplex contained less than about 20% 2'OMe-modified nucleotides. The NP siRNA molecules were formulated as lipoplexes and tested for their ability to significantly reduce the cytopathic effect (CPE) produced by influenza virus at about 48 hours after infection. The NP siRNA molecules were also tested for the amount of HA produced (i.e., HA units/well) and the percentage of HA produced relative to a virus only control (i.e., percent knockdown).

TABLE 6 siRNA duplexes comprising sense and antisense NP RNA polynucleotides.

| Position | Modification | NP siRNA sequence | SEQ ID NO: | % 2'OMe-Modified | % Modified in DS Region |
|---|---|---|---|---|---|
| 411 | 0/0 | 5'-AGCUAAUAAUGGUGACGAUdTdT-3' | 75 | 0/42 = 0% | 0/38 = 0% |
| | | 3'-dTdTUCGAUUAUUACCACUGCUA-5' | 76 | | |
| 411 | U5/0 | 5'-AGC<u>U</u>AA<u>U</u>AA<u>U</u>GG<u>U</u>GACGA<u>U</u>dTdT-3' | 77 | 5/42 = 11.9% | 5/38 = 13.2% |
| | | 3'-dTdTUCGAUUAUUACCACUGCUA-5' | 76 | | |
| 929 | 0/0 | 5'-GAUACUCUCUAGUCGGAAUdTdT-3' | 78 | 0/42 = 0% | 0/38 = 0% |
| | | 3'-dTdTCUAUGAGAGAUCAGCCUUA-5' | 79 | | |
| 929 | U6/0 | 5'-GA<u>U</u>AC<u>U</u>C<u>U</u>C<u>U</u>AG<u>U</u>CGGAA<u>U</u>dTdT-3' | 80 | 6/42 = 14.3% | 6/38 = 15.8% |
| | | 3'-dTdTCUAUGAGAGAUCAGCCUUA-5' | 79 | | |

TABLE 6-continued siRNA duplexes comprising sense and antisense NP RNA polynucleotides.

| Position | Modification | NP siRNA sequence | SEQ ID NO: | % 2'OMe-Modified | % Modified in DS Region |
|---|---|---|---|---|---|
| 1116 | 0/0 | 5'-GCUUUCCACUAGAGGAGUUdTdT-3' | 81 | 0/42 = 0% | 0/38 = 0% |
| | | 3'-dTdTCGAAAGGUGAUCUCCUCAA-5' | 82 | | |
| 1116 | U5/0 | 5'-GCUUUCCACUAGAGGAGUUdTdT-3' | 83 | 5/42 = 11.9% | 5/38 = 13.2% |
| | | 3'-dTdTCGAAAGGUGAUCUCCUCAA-5' | 82 | | |
| 1496 | 0/0 | 5'-GGAUCUUAUUUCUUCGGAGdTdT-3' | 84 | 0/42 = 0% | 0/38 = 0% |
| | | 3'-dTdTCCUAGAAUAAAGAAGCCUC-5' | 85 | | |
| 1496 | U4/0 | 5'-GGAUCUUAUUCUUCGGAGdTdT-3' | 86 | 4/42 = 9.5% | 4/38 = 10.5% |
| | | 3'-dTdTCCUAGAAUAAAGAAGCCUC-5' | 85 | | |
| 1496 | U8/0 | 5'-GGAUCUUAUUUCUUCGGAGdTdT-3' | 87 | 8/42 = 19% | 8/38 = 21% |
| | | 3'-dTdTCCUAGAAUAAAGAAGCCUC-5' | 85 | | |

Column 1: The number refers to the nucleotide position of the 5' base of the sense strand relative to the Influenza A virus NP ssRNA sequence NC_004522.
Column 2: The numbers refer to the distribution of 2'OMe chemical modifications in each strand. For example, "U5/0" indicates 5 uridine 2'OMe modifications in the sense strand and no uridine 2'OMe modifications in the antisense strand.
Column 3: 2'OMe-modified nucleotides are indicated in bold and underlined; "dT" = deoxythymidine.
Column 4: The number and percentage of 2'OMe-modified nucleotides in the siRNA duplex are provided.
Column 5: The number and percentage of modified nucleotides in the double-stranded (DS) region of the siRNA duplex are provided.

Figure 17A:
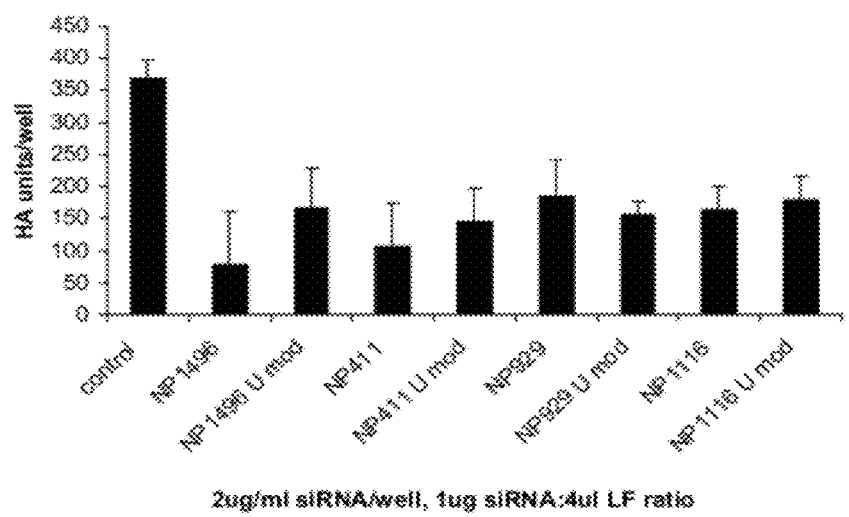
FIG. 17 illustrates data demonstrating that NP 411, NP 929, NP 1116, and NP 1496 siRNA comprising selective 2'OMe modifications to the sense strand maintain influenza knockdown activity in v TechNotes, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).
Figure 17B:
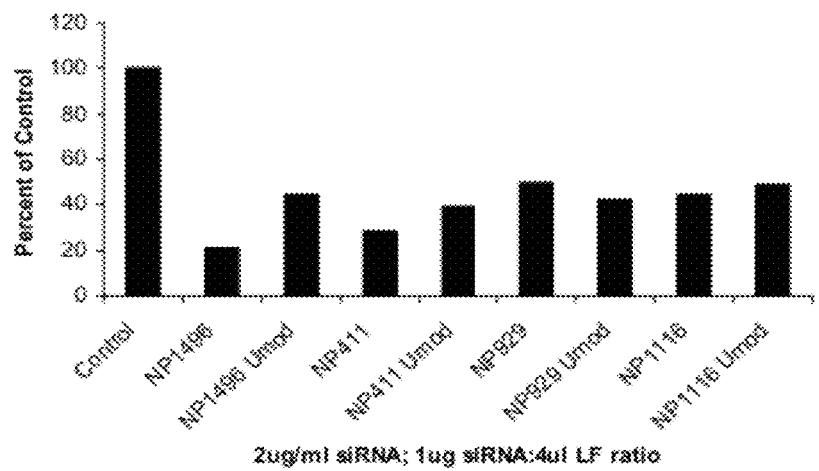
Figure 18:
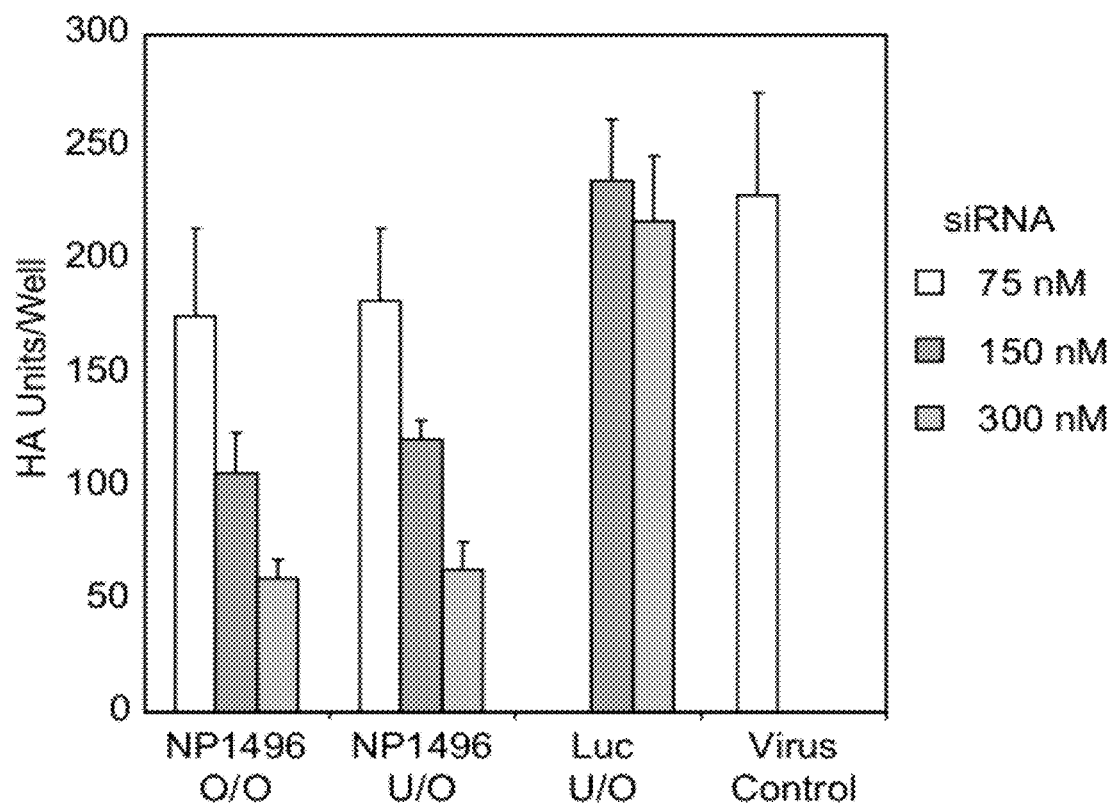
Figure 19A:
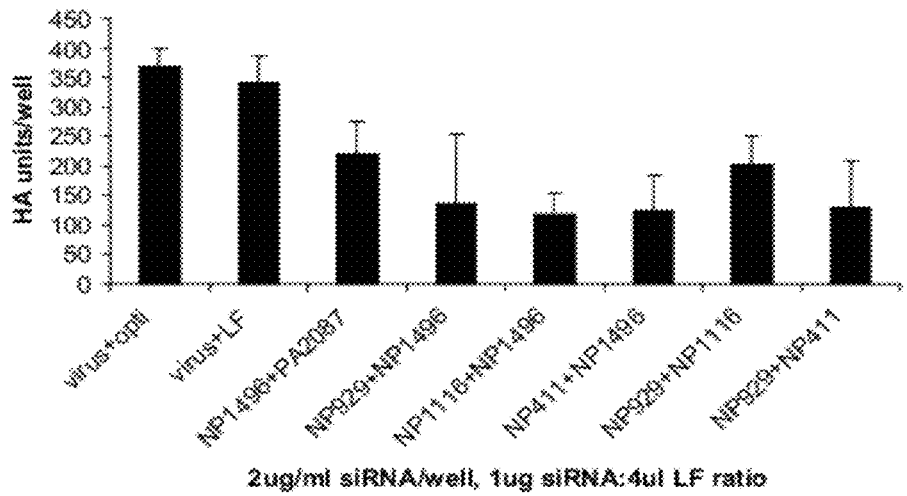
Figure 19B:
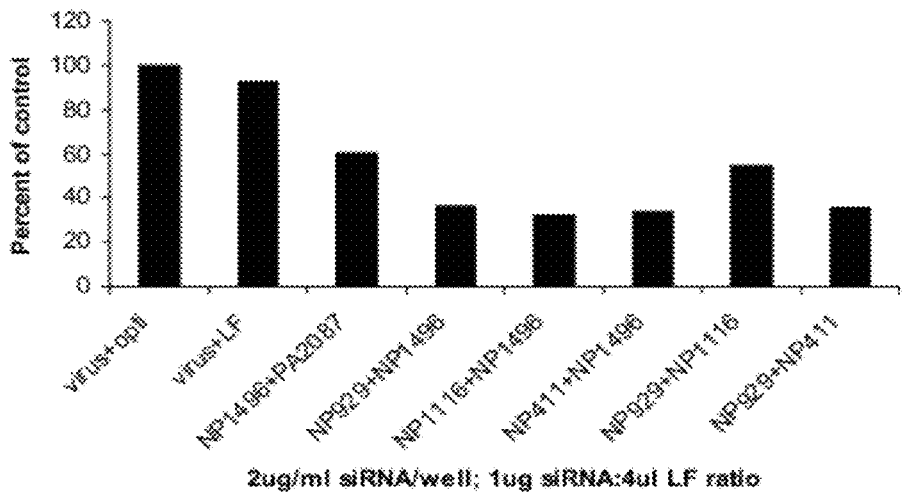

FIGS. 17 and 18 show that selective 2'OMe modifications to the sense strand of the NP siRNA duplex did not negatively affect influenza knockdown activity when compared to unmodified counterpart sequences or control sequences. FIG. 19 shows that various combinations of these 2'OMe-modified NP siRNA molecules provided enhanced knockdown of influenza virus in MDCK cells relative to controls.

Figure 20:
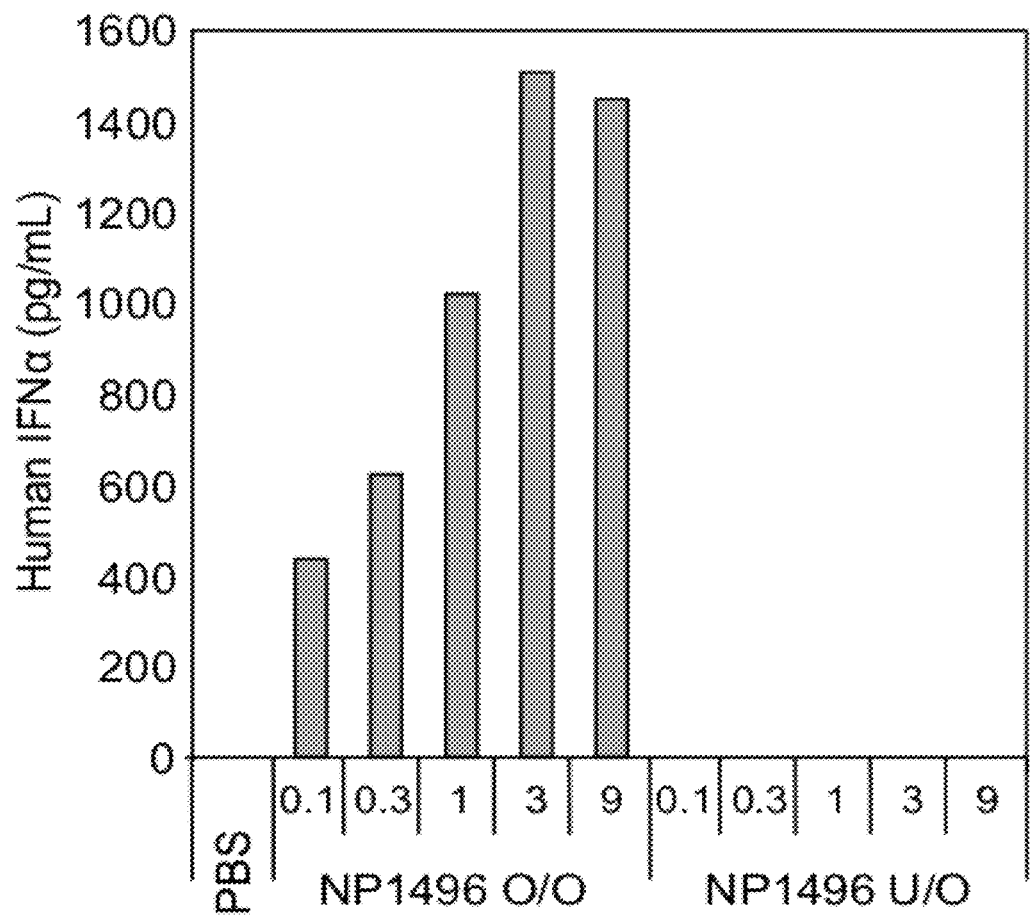
Figure 21:
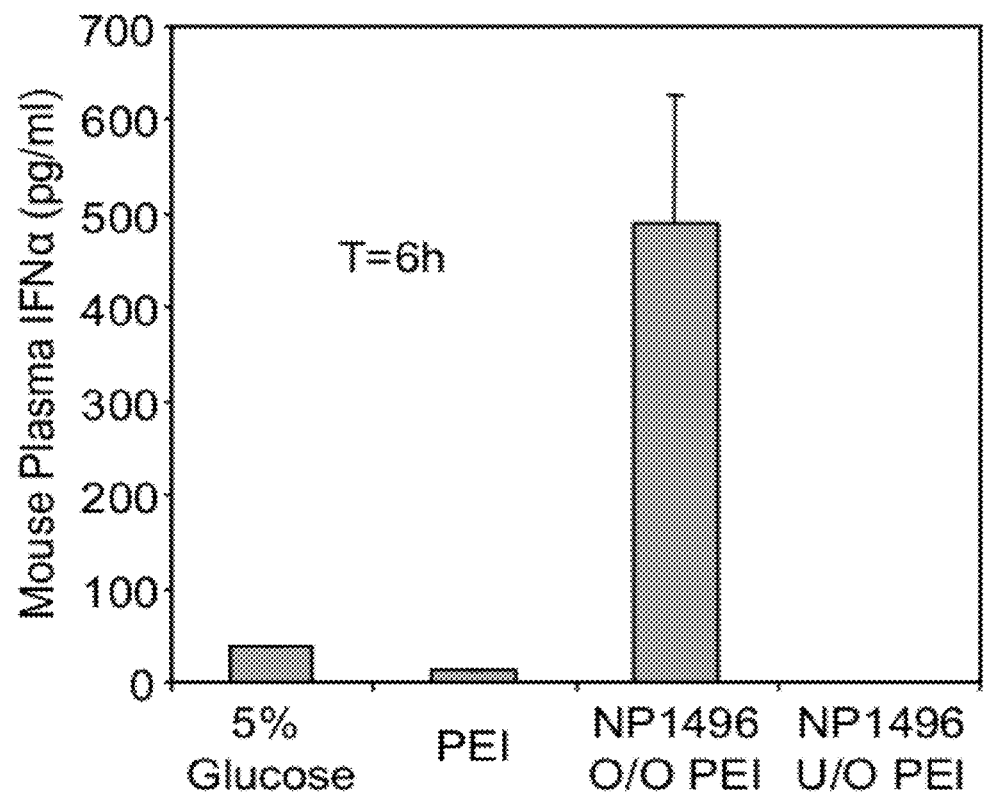

Selective modifications to NP siRNA abrogate in vitro and in vivo cytokine induction. Unmodified NP 1496 siRNA (i.e., 0/0) and a 2'OMe-modified variant thereof (i.e., U8/0) were either encapsulated into SNALPs having 2 mol % PEG-cDMA, 40 mol % DLinDMA, 10 mol % DSPC, and 48 mol % cholesterol or complexed with polyethylenimine (PEI) to form polyplexes. The SNALP-formulated NP-targeting siRNA were tested in vitro to look for the induction of an immune response, e.g., cytokine induction. Human peripheral blood mononuclear cells (PBMCs) were transfected with 40 µg of the SNALP formulation comprising NP 1496 siRNA and supernatants collected for cytokine analysis at 16 hours. The polyplex formulations were tested in vivo to look for the induction of an immune response, e.g., cytokine induction. Mice were intravenously injected with the polyplexes at 120 µg siRNA/mouse and plasma samples were collected 6 hours post-treatment and tested for interferon-α levels by an ELISA assay. FIG. 20 shows that selective 2'OMe modifications to NP 1496 siRNA abrogated interferon induction in an in vitro cell culture system. FIG. 21 shows that selective 2'OMe modifications to NP 1496 siRNA abrogated the interferon induction associated with systemic administration of the native (i.e., unmodified) duplex.

Methods siRNA: All siRNA used in these studies were chemically synthesized by Protiva Biotherapeutics (Burnaby, BC), University of Calgary (Calgary, AB), or Dharmacon Inc. (Lafayette, Colo.). siRNA were desalted and annealed using standard procedures.

Lipid encapsulation of siRNA: Unless otherwise indicated, siRNAs were encapsulated into liposomes composed of the following lipids; synthetic cholesterol (Sigma; St. Louis, Mo.), the phospholipid DSPC (1,2-distearoyl-sn-glycero-3-phosphocholine; Avanti Polar Lipids; Alabaster, Ala.), the PEG-lipid PEG-cDMA (3-N-[(-Methoxy poly(ethylene glycol)2000)carbamoyl]-1,2-dimyrestyloxy-propylamine), and the cationic lipid DLinDMA (1,2-Dilinoleyloxy-3-(N,N-dimethyl)aminopropane) in the molar ratio 48:10:2:40. In other words, unless otherwise indicated, siRNAs were encapsulated into liposomes of the following SNALP formulation: 2 mol % PEG-cDMA, 40 mol % DLinDMA, 10 mol % DSPC, and 48 mol % cholesterol.

Lipoplex treatment and in vitro influenza infection: The influenza virus (e.g., Influenza A/PR/8/34 H1N1) produces a cytopathic effect in MDCK cells upon infection in the presence of trypsin. The lipoplex treatment and in vitro influenza infection of MDCK cells was performed according to the following protocol:

1. MDCK cells were seeded in 96 well plates at about 8000 cells/well (about $4\times10^4$ cells/ml) so that the cells were at about 50% density 24 hours after seeding.
2. About 24 hours later, media was changed to fresh complete media (no antibiotics) and cells were transfected with a lipoplex comprising nucleic acid (e.g., NP siRNA) in Lipofectamine™ 2000 (LF2000) (Invitrogen Corp.; Camarillo, Calif.) at a 1:4 ratio of nucleic acid:LF2000.
3. About 4 hours later, complexes were removed, cells were washed with PBS, and cells were infected with various dilutions of influenza virus in virus infection media (DMEM, 0.3% BSA, 10 mM HEPES), adding about 50 μl diluted virus/well.
4. Virus was incubated on cells for about 1-2 hours at 37° C., followed by removal of virus and addition of about 200 μl of virus growth media (DMEM, 0.3% BSA, 10 mM HEPES, 0.25 μg/ml trypsin).

5. Cells were monitored for cytopathic effect at about 48 hours.
6. Influenza HA enzyme immunoassays (EIA) were performed on supernatants.

Polyplex treatment and in vivo cytokine induction: Animal studies were completed in accordance with the Canadian Council on Animal Care guidelines following approval by the local Animal Care and Use Committee at Protiva Biotherapeutics. 6-8 week old CD1 ICR mice (Harlan; Indianapolis, Ind.) were subjected to a three week quarantine and acclimation period prior to use. siRNAs were mixed with In vivo jetPEI™ (Qbiogene, Inc.; Carlsbad, Calif.) according to the manufacturer's instructions at an N/P ratio of 5 at room temperature for 20 min. Mice were administered the In vivo jetPEI™ polyplexes, corresponding to 120 μg siRNA/mouse, by standard intravenous injection in the lateral tail vein in 0.2 ml PBS. Blood was collected by cardiac puncture 6 hours after administration and processed as plasma for cytokine analysis. Interferon-α levels in plasma were measured using a sandwich ELISA method according to the manufacturer's instructions (PBL Biomedical; Piscataway, N.J.). Additional methods for PEI polyplex formation are provided in Judge et al., *Nat. Biotechnol.*, 23:457-462 (2005).

In vitro cytokine induction: PBMCs were transfected with 40 μg of SNALP-formulated siRNA and interferon-α levels were assayed in cell culture supernatants after 16 hours using a sandwich ELISA method according to the manufacturer's instructions (PBL Biomedical; Piscataway, N.J.).

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A modified siRNA comprising a double-stranded region of about 15 to about 30 nucleotides in length, wherein from 15% to about 30% of the nucleotides in the double-stranded region comprise 2'-O-methyl (2'OMe) nucleotides,
   wherein the modified siRNA comprises 2'OMe nucleotides in both strands of the modified siRNA,
   wherein the modified siRNA comprises 2'OMe nucleotides selected from the group consisting of 2'OMe-guanosine nucleotides, 2'OMe-uridine nucleotides, 2'OMe-adenosine nucleotides, and mixtures thereof,
   wherein the modified siRNA does not comprise 2'OMe-cytosine nucleotides in the double-stranded region,
   wherein the modified siRNA is less immunostimulatory than a corresponding unmodified siRNA sequence, and
   wherein the modified siRNA is capable of silencing expression of a target sequence.

2. The modified siRNA of claim 1, wherein the modified siRNA comprises a double-stranded region of about 19 to about 25 nucleotides in length.

3. The modified siRNA of claim 1, wherein from about 20% to about 30% of the nucleotides in the double-stranded region comprise 2'OMe nucleotides.

4. The modified siRNA of claim 1, wherein from about 25% to about 30% of the nucleotides in the double-stranded region comprise 2'OMe nucleotides.

5. The modified siRNA of claim 1, wherein the modified siRNA has an interferon-α (IFN-α) response that is about 80% or more lower than the IFN-α response detected for the corresponding unmodified siRNA sequence.

6. The modified siRNA of claim 1, wherein the modified siRNA comprises a 3' overhang in both strands of the modified siRNA.

7. The modified siRNA of claim 6, wherein the 3' overhang in one or both strands of the modified siRNA comprises unmodified nucleotides, modified nucleotides, and combinations thereof.

8. The modified siRNA of claim 1, wherein the modified siRNA comprises a sense strand sequence comprising nucleotides 1-19 of SEQ ID NO:59.

9. The modified siRNA of claim 8, wherein the sense strand sequence comprises a 3' overhang of two nucleotides.

10. The modified siRNA of claim 9, wherein the 3' overhang comprises unmodified nucleotides, modified nucleotides, and combinations thereof.

11. The modified siRNA of claim 1, wherein the modified siRNA comprises a sense strand sequence consisting of SEQ ID NO:59.

12. The modified siRNA of claim 1, wherein the modified siRNA comprises an antisense strand sequence comprising nucleotides 1-19 of SEQ ID NO:54.

13. The modified siRNA of claim 12, wherein the antisense strand sequence comprises a 3' overhang of two nucleotides.

14. The modified siRNA of claim 13, wherein the 3' overhang comprises unmodified nucleotides, modified nucleotides, and combinations thereof.

15. The modified siRNA of claim 1, wherein the modified siRNA comprises an antisense strand sequence consisting of SEQ ID NO:54.

16. The modified siRNA of claim 1, wherein the modified siRNA targets Apolipoprotein B (ApoB) and the corresponding unmodified siRNA sequence comprises the sequence:

5'-AGUGUCAUCACACUGAAUACC-3'   (SEQ ID NO: 46)
3'-GUUCACAGUAGUGUGACUUAU-5'   (SEQ ID NO: 47).

17. A pharmaceutical composition comprising a modified siRNA of claim 1 and a pharmaceutically acceptable carrier.

18. A nucleic acid-lipid particle comprising:
   (a) a modified siRNA of claim 1;
   (b) a cationic lipid; and
   (c) a non-cationic lipid.

19. The nucleic acid-lipid particle of claim 18, further comprising a conjugated lipid that inhibits aggregation of particles.

20. The nucleic acid-lipid particle of claim 19, wherein the conjugated lipid that inhibits aggregation of particles comprises a polyethyleneglycol (PEG)-lipid conjugate.

21. The nucleic acid-lipid particle of claim 20, wherein the PEG-lipid conjugate comprises a PEG-dialkyloxypropyl (PEG-DAA) conjugate.

22. The nucleic acid-lipid particle of claim 21, wherein the PEG-DAA conjugate is a PEG-dimyristyloxypropyl ($C_{14}$) conjugate.

23. The nucleic acid-lipid particle of claim 21, wherein the PEG-DAA conjugate comprises from 0.5 mol % to about 20 mol % of the total lipid present in the particle.

24. The nucleic acid-lipid particle of claim 18, wherein the cationic lipid comprises from about 2 mol % to about 60 mol % of the total lipid present in the particle.

25. The nucleic acid-lipid particle of claim 18, wherein the non-cationic lipid comprises from about 5 mol % to about 90 mol % of the total lipid present in the particle.

26. The nucleic acid-lipid particle of claim 18, wherein the non-cationic lipid comprises a phospholipid and cholesterol.

27. The nucleic acid-lipid particle of claim 18, wherein the modified siRNA is fully encapsulated in the nucleic acid-lipid particle.

28. A pharmaceutical composition comprising a nucleic acid-lipid particle of claim 18 and a pharmaceutically acceptable carrier.

* * * * *